US009920119B2

United States Patent
Taupin et al.

(10) Patent No.: US 9,920,119 B2
(45) Date of Patent: Mar. 20, 2018

(54) CHIMERIC MOLECULE INVOLVING OLIGOMERIZED FASL EXTRACELLULAR DOMAIN

(71) Applicant: CENTRE NATIONAL DE LA RECHERCHE SCIENTIFIQUE, Paris (FR)

(72) Inventors: Jean-Luc Taupin, Bordeaux (FR); Sophie Daburon, Tresses (FR); Jean-Francois Moreau, Merignac (FR); Myriam Capone, Le Bouscat (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 71 days.

(21) Appl. No.: 14/354,777

(22) PCT Filed: Oct. 26, 2012

(86) PCT No.: PCT/EP2012/071291
§ 371 (c)(1),
(2) Date: Apr. 28, 2014

(87) PCT Pub. No.: WO2013/060864
PCT Pub. Date: May 2, 2013

(65) Prior Publication Data
US 2015/0044237 A1 Feb. 12, 2015

(30) Foreign Application Priority Data
Oct. 27, 2011 (EP) ..................................... 11306395

(51) Int. Cl.
*C07K 14/475* (2006.01)
*C07K 14/715* (2006.01)
(Continued)

(52) U.S. Cl.
CPC ............ *C07K 16/24* (2013.01); *C07K 14/525* (2013.01); *C07K 14/70575* (2013.01);
(Continued)

(58) Field of Classification Search
None
See application file for complete search history.

(56) References Cited

U.S. PATENT DOCUMENTS 8,383,777 B2 * 2/2013 Afar ................... A61K 38/1709

FOREIGN PATENT DOCUMENTS

WO 2009007120 A2 1/2009

OTHER PUBLICATIONS

Phillips, AJ, The challenge of gene therapy and DNA delivery, J. Pharm. Pharmacol. 53(8):1169-1174, 2001.*
(Continued)

*Primary Examiner* — Claire Kaufman
(74) *Attorney, Agent, or Firm* — Young & Thompson

(57) ABSTRACT

New chimeric molecules involving in their structure, a combination of the extracellular domain (EC) of the FasL protein and a domain enabling oligomerisation of this Fas Ligand (FasL) EC domain, such as the Ig-like (so-called Ig in the following pages) domain of the gp190 receptor for the Leukemia Inhibitory Factor (LIF), or involving in their structure variants of the domains. Also, compositions including the chimeric molecule defined herein and the use of these chimeric molecules especially to trigger cytotoxic activity toward cells sensitive to FasL.

23 Claims, 18 Drawing Sheets

(51) Int. Cl.
| | |
|---|---|
| C07K 4/00 | (2006.01) |
| C07K 19/00 | (2006.01) |
| C12N 5/10 | (2006.01) |
| C12N 15/62 | (2006.01) |
| A61K 38/19 | (2006.01) |
| A61K 38/16 | (2006.01) |
| C07K 16/24 | (2006.01) |
| C07K 14/705 | (2006.01) |
| C07K 14/525 | (2006.01) |
| A61K 38/00 | (2006.01) |

(52) U.S. Cl.
CPC .......... *C07K 14/715* (2013.01); *A61K 38/00* (2013.01); *C07K 2319/01* (2013.01); *C07K 2319/32* (2013.01); *C07K 2319/75* (2013.01)

(56) References Cited

OTHER PUBLICATIONS

Jackson et al., Designing nonvirla vectors for efficient gene transfer and long-term gene expression, Mol. Ther. 14(5):613-626, Nov. 2006.*

Huyton et al., An unusual cytokine:Ig-domain interaction revealed in the crystal structure of leukemia inhibitory factor (LIF) in complex with the LIF receptor, Proc. Natl. Acad. Scie, USA, 104(:31):12737-12743, Jul. 21, 2007).*

GenBank Database, Accession NP_003990.1, Oncostatin-M-specific receptor subunit beta isoform 1 precurson [*Homo sapiens*], {{Retrieved online Sep. 22, 2016] <URL: http://www.ncbi.nlm.nih.gov/protein/NP_003990.1>, Apr. 22, 2016.*

Mosley et al., Dual oncostatin M (OSM) receptors, J. Biol. Chem. 271(50):32635-43, 1996.*

Prasad et al., Delivering multiple anticancer peptides as a single prodrug using lysl-lysine as a facile linker, J. Prot. Sci. 13:458-467, 2007.*

Bodmer et al., "The molecular architecture of the TNF superfamily", Trends in Biochemical Sciences, vol. 27, No. 1, 2002, pp. 19-26.

Gearing et al., "Leukemia inhibitory factor receptor is structurally related to the IL-6 signal transducer, gp130", The EMBO Journal, 1991, vol. 10, No. 10, abstract only.

Holler et al., "Two Adjacent Trimeric Fas Ligands Are Required for Fas Signaling and Formation of a Death-Inducing Signaling Complex", Molecular and Cellular Biology, 2003, vol. 23, No. 4, pp. 1428-1440.

Liu et al., "Involving of the cytoplasmic region of leukemia inhibitory factor receptor a subunit, IL-6 related signal transducer-gp130 or Fas death domain for MAPK p42/44 activation in HL-60 cell with LIF or anti-Fas IgG", Molecular and Cellular Biochemistry, 2001, vol. 217, pp. 113-120.

Legembre et al., "Cutting Edge: SDS—Stable Fas Microaggregates: An Early Event of Fas Activation Occurring with Agonistic Anti-Fas Antibody but Not with Fas Ligand", The Journal of Immunology, 2003, vol. 171, pp. 5659-5662.

Schneider et al., "Conversion of Membrane-bound Fas(CD95) Ligand to Its Soluble Form Is Associated with Downregulation of Its Proapoptotic Activity and Loss of Liver Toxicity", J. Exp. Med., 1998, vol. 187, No. 8, pp. 1205-1213.

Shiraishi et al., "Increased cytotoxicity of soluble Fas ligand by fusing isoleucine zipper motif", Biochemical and Biophysical Research Communications, 2004, vol. 322, pp. 197-202.

Suda et al., "Membrane Fas Ligand Kills Human Peripheral Blood T Lymphocytes, and Soluble Fas Blocks the Kiling", J. Exp. Med., 1997, vol. 186, No. 12, pp. 2045-2050.

Taupin et al., "Binding of Leukemia Inhibitory Factor (LIF) to Mutants of Its Low Affinity Receptor, gp190, Reveals a LIF Binding Site Outside and Interactions between the Two Cytokine Binding Domains", J. Biol. Chem., 1999, vol. 274, pp. 14482-14489.

Voisin et al., "Separate Functions for the Two Modules of the Membrane-proximal Cytokine Binding Domain of Glycoprotein 190, the Leukemia Inhibitory Factor Low Affinity Receptor, in Ligand Binding and Receptor Activation", J. Biol. Chem., 2002, vol. 277, pp. 13682-13692.

International Search Report, dated Jan. 7, 2013, from corresponding PCT application, WO 2013/060864.

\* cited by examiner

Figure 1
A
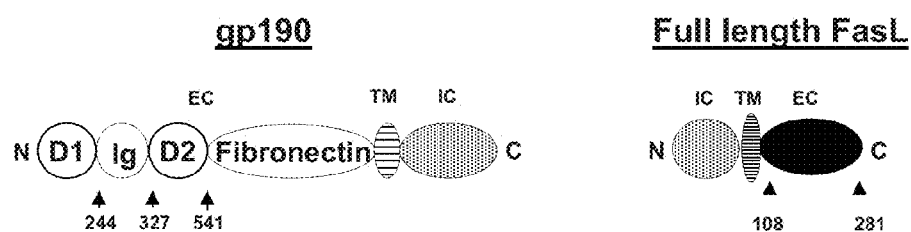
B
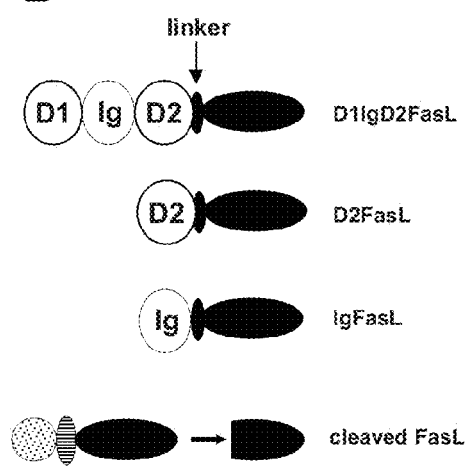
C
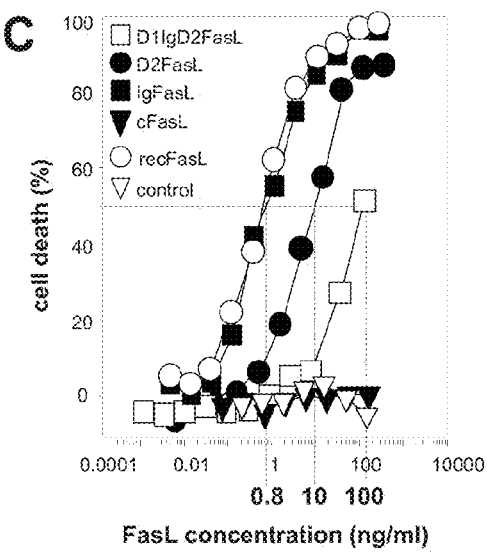

Figure 5 (1)

DNA sequences

SEQ ID No 9:
**ATGATGGATATTTACGTATGTTTGAAACGACCATCCTGGATGGTGG
ACAATAAAAGAATGAGGACTGCTTCAAATTTCCAGTGGCTGTTATC
AACATTTATTCTTCTATATCTAATGAATCAAGTAAATAGC**CAGAAAA
AGACTAGT

SEQ ID No 3:
ATACCTGATTCTCAGACTAAGGTTTTTCCTCAAGATAAAGTGATACTTGTA
GGCTCAGACATAACATTTTGTTGTGTGAGTCAAGAAAAAGTGTTATCAGC
ACTGATTGGCCATACAAACTGCCCCTTGATCCATCTTGATGGGGAAAATG
TTGCAATCAAGATTCGTAATATTTCTGTTTCTGCAAGTAGTGGAACAAAT
GTAGTTTTTACAACCGAAGATAACATATTTGGAACCGTTATT

SEQ ID No 5:
TCTAGAGCC

SEQ ID No 7:
CTACAGAAGGAGCTGGCAGAACTCCGAGAGTCTACCAGCCAGATGCAC
ACAGCATCATCTTTGGAGAAGCAAATAGGCCACCCCAGTCCACCCCCTG
AAAAAAAGGAGCTGAGGAAAGTGGCCCATTTAACAGGCAAGTCCAACTC
AAGGTCCATGCCTCTGGAATGGGAAGACACCTATGGAATTGTCCTGCTT
TCTGGAGTGAAGTATAAGAAGGGTGGCCTTGTGATCAATGAAACTGGGC
TGTACTTTGTATATTCCAAAGTATACTTCCGGGGTCAATCTTGCAACAAC
CTGCCCCTGAGCCACAAGGTCTACATGAGGAACTCTAAGTATCCCCAGG
ATCTGGTGATGATGGAGGGGAAGATGATGAGCTACTGCACTACTGGGC
AGATGTGGGCCCGCAGCAGCTACCTGGGGGCAGTGTTCAATCTTACCAG
TGCTGATCATTTATATGTCAACGTATCTGAGCTCTCTCTGGTCAATTTTGA
GGAATCTCAGACGTTTTTCGGCTTATATAAGCTC<u>TAA</u>

SEQ ID No 1:
ATGATGGATATTTACGTATGTTTGAAACGACCATCCTGGATGGTGGACAA
TAAAAGAATGAGGACTGCTTCAAATTTCCAGTGGCTGTTATCAACATTTA
TTCTTCTATATCTAATGAATCAAGTAAATAGCCAGAAAAGACTAGTATAC
CTGATTCTCAGACTAAGGTTTTTCCTCAAGATAAAGTGATACTTGTAGGC
TCAGACATAACATTTTGTTGTGTGAGTCAAGAAAAAGTGTTATCAGCACT
GATTGGCCATACAAACTGCCCCTTGATCCATCTTGATGGGGAAAATGTTG
CAATCAAGATTCGTAATATTTCTGTTTCTGCAAGTAGTGGAACAAATGTA
GTTTTTACAACCGAAGATAACATATTTGGAACCGTTATTTCTAGAGCCCT
ACAGAAGGAGCTGGCAGAACTCCGAGAGTCTACCAGCCAGATGCACAC
AGCATCATCTTTGGAGAAGCAAATAGGCCACCCCAGTCCACCCCCTGAA
AAAAAGGAGCTGAGGAAAGTGGCCCATTTAACAGGCAAGTCCAACTCAA
GGTCCATGCCTCTGGAATGGGAAGACACCTATGGAATTGTCCTGCTTTC
TGGAGTGAAGTATAAGAAGGGTGGCCTTGTGATCAATGAAACTGGGCTG
TACTTTGTATATTCCAAAGTATACTTCCGGGGTCAATCTTGCAACAACCT
GCCCCTGAGCCACAAGGTCTACATGAGGAACTCTAAGTATCCCCAGGAT
CTGGTGATGATGGAGGGGAAGATGATGAGCTACTGCACTACTGGGCAG
ATGTGGGCCCGCAGCAGCTACCTGGGGGCAGTGTTCAATCTTACCAGTG
CTGATCATTTATATGTCAACGTATCTGAGCTCTCTCTGGTCAATTTTGAG
GAATCTCAGACGTTTTTCGGCTTATATAAGCTC<u>TAA</u>

Figure 5 (2)

Protein sequences

SEQ ID No 10:

MMDIYVCLKRPSWMVDNKRMRTASNFQWLLSTFILLYLMNQVNSQKK<u>T</u>
<u>S</u>

SEQ ID No 4:

IPDSQTKVFPQDKVILVGSDITFCCVSQEKVLSALIGHTNCPLIHLDGENVAIKIRNI
SVSASSGTNVVFTTEDNIFGTVI

SEQ ID No 6:

SRA

Seq ID No 8:

LQKELAELRESTSQMHTASSLEKQIGHPSPPPEKKELRKVAHLTGKSNSRSMPLE
WEDTYGIVLLSGVKYKKGGLVINETGLYFVYSKVYFRGQSCNNLPLSHKVYMRNS
KYPQDLVMMEGKMMSYCTTGQMWARSSYLGAVFNLTSADHLYVNVSELSLVNFE
ESQTFFGLYKL

SEQ ID no 2:

MMDIYVCLKRPSWMVDNKRMRTASNFQWLLSTFILLYLMNQVNSQKKTSIPDSQ
TKVFPQDKVILVGSDITFCCVSQEKVLSALIGHTNCPLIHLDGENVAIKIRNISVSA
SSGTNVVFTTEDNIFGTVISRALQKELAELRESTSQMHTASSLEKQIGHPSPPPEK
KELRKVAHLTGKSNSRSMPLEWEDTYGIVLLSGVKYKKGGLVINETGLYFVYSKVY
FRGQSCNNLPLSHKVYMRNSKYPQDLVMMEGKMMSYCTTGQMWARSSYLGAVF
NLTSADHLYVNVSELSLVNFEESQTFFGLYKL

Figure 6(1)

SEQ ID N° 15 : human CD80 cDNA, extracellular region

ATGGGCCACACACGGAGGCAGGGAACATCACCATCCAAGTGTCCATACCTCAATTTCTTTCAGCTCTTGGTGC
TGGCTGGTCTTTCTCACTTCTGTTCAGGTGTTATCCACGTGACCAAGGAAGTGAAAGAAGTGGCAACGCTGTC
CTGTGGTCACAATGTTTCTGTTGAAGAGCTGGCACAAACTCGCATCTACTGGCAAAAGGAGAAGAAAATGGTG
CTGACTATGATGTCTGGGGACATGAATATATGGCCCGAGTACAAGAACCGGACCATCTTTGATATCACTAATAA
CCTCTCCATTGTGATCCTGGCTCTGCGCCCATCTGACGAGGGCACATACGAGTGTGTTGTTCTGAAGTATGAA
AAAGACGCTTTCAAGCGGGAACACCTGGCTGAAGTGACGTTATCAGTCAAAGCTGACTTCCCTACACCTAGTA
TATCTGACTTTGAAATTCCAACTTCTAATATTAGAAGGATAATTTGCTCAACCTCTGGAGGTTTTCCAGAGCCTC
ACCTCTCCTGGTTGGAAAATGGAGAAGAATTAAATGCCATCAACACAACAGTTTCCCAAGATCCTGAAACTGAG
CTCTATGCTGTTAGCAGCAAACTGGATTTCAATATGACAACCAACCACAGCTTCATGTGTCTCATCAAGTATGG
ACATTTAAGAGTGAATCAGACCTTCAACTGGAATACAACCAAGCAAGAGCATTTTCCTTCTAGA

SEQ ID N° 16 : human CD80 protein, extracellular region

MGHTRRQGTSPSKCPYLNFFQLLVLAGLSHFCSGVIHVTKEVKEVATLSCGHNVSVEELAQTRIYWQKEKKMV
LTMMSGDMNIWPEYKNRTIFDITNNLSIVILALRPSDEGTYECVVLKYEKDAFKREHLAEVTLSVKADFPTPSIS
DFEIPTSNIRRIICSTSGGFPEPHLSWLENGEELNAINTTVSQDPETELYAVSSKLDFNMTTNHSFMCLIKYGHL
RVNQTFNWNTTKQEHFPSR

Figure 6 (2)

SEQ ID N° 17 : complete DNA sequence for CD80IgFasL

ATGGGCCACACACGGAGGCAGGGAACATCACCATCCAAGTGTCCATACCTCAATTTCTTTCAGCTCT
TGGTGCTGGCTGGTCTTTCTCACTTCTGTTCAGGTGTTATCCACGTGACCAAGGAAGTGAAAGAAGT
GGCAACGCTGTCCTGTGGTCACAATGTTTCTGTTGAAGAGCTGGCACAAACTCGCATCTACTGGCAA
AAGGAGAAGAAAATGGTGCTGACTATGATGTCTGGGGACATGAATATATGGCCCGAGTACAAGAAC
CGGACCATCTTTGATATCACTAATAACCTCTCCATTGTGATCCTGGCTCTGCGCCCATCTGACGAGG
GCACATACGAGTGTGTTGTTCTGAAGTATGAAAAGACGCTTTCAAGCGGGAACACCTGGCTGAAG
TGACGTTATCAGTCAAAGCTGACTTCCCTACACCTAGTATATCTGACTTTGAAATTCCAACTTCTAATA
TTAGAAGGATAATTTGCTCAACCTCTGGAGGTTTTCCAGAGCCTCACCTCTCCTGGTTGGAAAATGG
AGAAGAATTAAATGCCATCAACACAACAGTTTCCCAAGATCCTGAAACTGAGCTCTATGCTGTTAGC
AGCAAACTGGATTTCAATATGACAACCAACCACAGCTTCATGTGTCTCATCAAGTATGGACATTTAAG
AGTGAATCAGACCTTCAACTGGAATACAACCAAGCAAGAGCATTTTCCTTCTAGTATACCTGATTCT
CAGACTAAGGTTTTTCCTCAAGATAAAGTGATACTTGTAGGCTCAGACATAACATTTTGTTGTGTGAG
TCAAGAAAAAGTGTTATCAGCACTGATTGGCCATACAAACTGCCCCTTGATCCATCTTGATGGGGAA
AATGTTGCAATCAAGATTCGTAATATTTCTGTTTCTGCAAGTAGTGGAACAAATGTAGTTTTTACAAC
CGAAGATAACATATTTGGAACCGTTATTTCTAGAGCCTACAGAAGGAGCTGGCAGAACTCCGAGA
GTCTACCAGCCAGATGCACACAGCATCATCTTTGGAGAAGCAAATAGGCCACCCCAGTCCACCCCCT
GAAAAAAAGGAGCTGAGGAAAGTGGCCCATTTAACAGGCAAGTCCAACTCAAGGTCCATGCCTCTG
GAATGGGAAGACACCTATGGAATTGTCCTGCTTTCTGGAGTGAAGTATAAGAAGGGTGGCCTTGTG
ATCAATGAAACTGGGCTGTACTTTGTATATTCCAAAGTATACTTCCGGGGTCAATCTTGCAACAACCT
GCCCCTGAGCCACAAGGTCTACATGAGGAACTCTAAGTATCCCCAGGATCTGGTGATGATGGAGGG
GAAGATGATGAGCTACTGCACTACTGGGCAGATGTGGGCCCGCAGCAGCTACCTGGGGGCAGTGT
TCAATCTTACCAGTGCTGATCATTTATATGTCAACGTATCTGAGCTCTCTCTGGTCAATTTTGAGGAA
TCTCAGACGTTTTTCGGCTTATATAAGCTCTAA

SEQ ID N° 18 : complete polypeptidic sequence for CD80IgFasL

MGHTRRQGTSPSKCPYLNFFQLLVLAGLSHFCSGVIHVTKEVKEVATLSCGHNVSV
EELAQTRIYWQKEKKMVLTMMSGDMNIWPEYKNRTIFDITNNLSIVILALRPSDEGT
YECVVLKYEKDAFKREHLAEVTLSVKADFPTPSISDFEIPTSNIRRIICSTSGGFPEPH
LSWLENGEELNAINTTVSQDPETELYAVSSKLDFNMTTNHSFMCLIKYGHLRVNQTF
NWNTTKQEHFPSSIPDSQTKVFPQDKVILVGSDITFCCVSQEKVLSALIGHTNCPLI
HLDGENVAIKIRNISVSASSGTNVVFTTEDNIFGTVISRALQKELAELRESTSQMHT
ASSLEKQIGHPSPPPEKKELRKVAHLTGKSNSRSMPLEWEDTYGIVLLSGVKYKKG
GLVINETGLYFVYSKVYFRGQSCNNLPLSHKVYMRNSKYPQDLVMMEGKMMSYCTT
GQMWARSSYLGAVFNLTSADHLYVNVSELSLVNFEESQTFFGLYKL

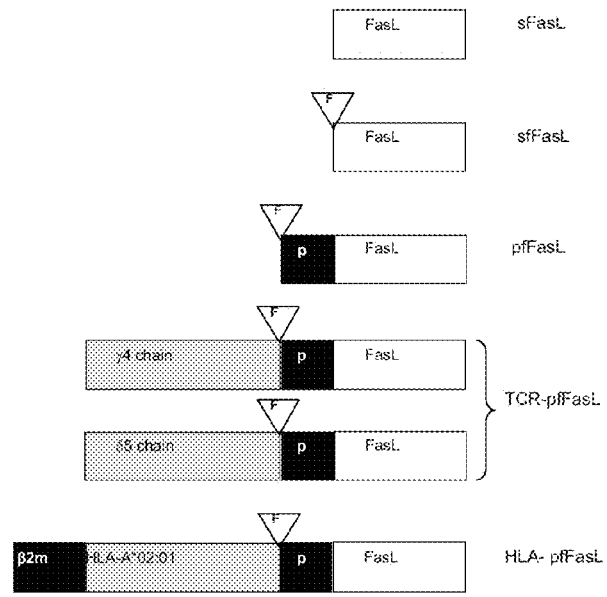
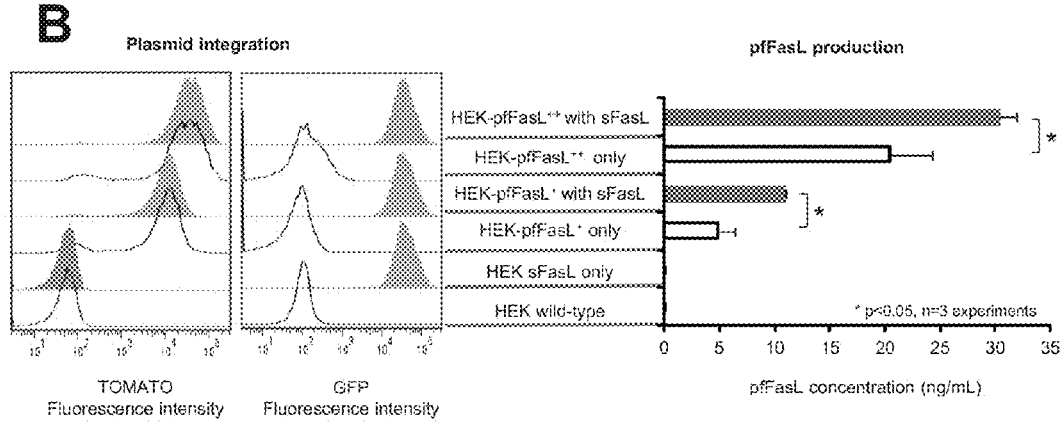
Figure 7

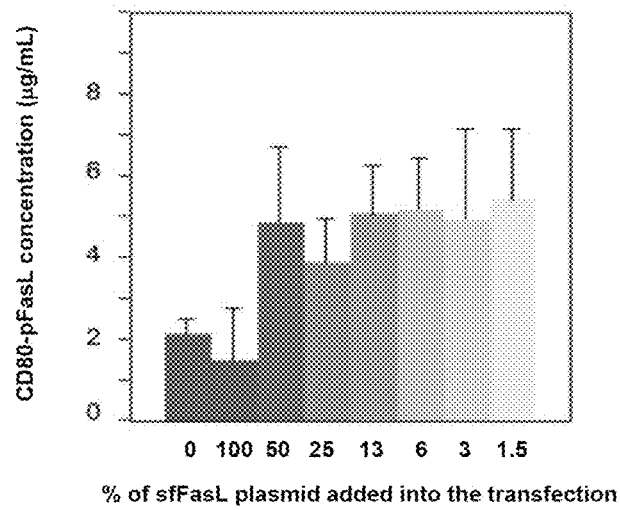
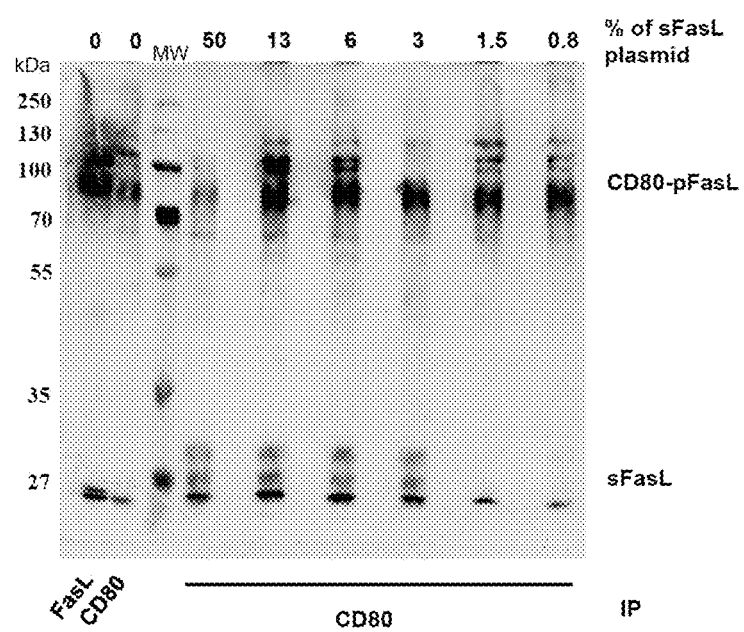
Figure 16

SEQUENCE LISTING

<160> NUMBER OF SEQ ID NOS: 25

<210> SEQ ID NO 1
<211> LENGTH: 927
<212> TYPE: DNA
<213> ORGANISM: Artificial
<220> FEATURE:
<223> OTHER INFORMATION: IgFasL chimeric gene (including signal peptide)
<220> FEATURE:
<221> NAME/KEY: CDS
<222> LOCATION: (1)..(927)

<400> SEQUENCE: 1

```
atg atg gat att tac gta tgt ttg aaa cga cca tcc tgg atg gtg gac      48
Met Met Asp Ile Tyr Val Cys Leu Lys Arg Pro Ser Trp Met Val Asp
1               5                   10                  15 aat aaa aga atg agg act gct tca aat ttc cag tgg ctg tta tca aca      96
Asn Lys Arg Met Arg Thr Ala Ser Asn Phe Gln Trp Leu Leu Ser Thr
            20                  25                  30 ttt att ctt cta tat cta atg aat caa gta aat agc cag aaa aag act     144
Phe Ile Leu Leu Tyr Leu Met Asn Gln Val Asn Ser Gln Lys Lys Thr
        35                  40                  45 agt ata cct gat tct cag act aag gtt ttt cct caa gat aaa gtg ata     192
Ser Ile Pro Asp Ser Gln Thr Lys Val Phe Pro Gln Asp Lys Val Ile
    50                  55                  60 ctt gta ggc tca gac ata aca ttt tgt tgt gtg agt caa gaa aaa gtg     240
Leu Val Gly Ser Asp Ile Thr Phe Cys Cys Val Ser Gln Glu Lys Val
65                  70                  75                  80 tta tca gca ctg att ggc cat aca aac tgc ccc ttg atc cat ctt gat     288
Leu Ser Ala Leu Ile Gly His Thr Asn Cys Pro Leu Ile His Leu Asp
                85                  90                  95 ggg gaa aat gtt gca atc aag att cgt aat att tct gtt tct gca agt     336
Gly Glu Asn Val Ala Ile Lys Ile Arg Asn Ile Ser Val Ser Ala Ser
            100                 105                 110 agt gga aca aat gta gtt ttt aca acc gaa gat aac ata ttt gga acc     384
Ser Gly Thr Asn Val Val Phe Thr Thr Glu Asp Asn Ile Phe Gly Thr
        115                 120                 125 gtt att tct aga gcc cta cag aag gag ctg gca gaa ctc cga gag tct     432
Val Ile Ser Arg Ala Leu Gln Lys Glu Leu Ala Glu Leu Arg Glu Ser
    130                 135                 140
```

```
acc agc cag atg cac aca gca tca tct ttg gag aag caa ata ggc cac      480
Thr Ser Gln Met His Thr Ala Ser Ser Leu Glu Lys Gln Ile Gly His
145                 150                 155                 160 ccc agt cca ccc cct gaa aaa aag gag ctg agg aaa gtg gcc cat tta      528
Pro Ser Pro Pro Pro Glu Lys Lys Glu Leu Arg Lys Val Ala His Leu
                165                 170                 175 aca ggc aag tcc aac tca agg tcc atg cct ctg gaa tgg gaa gac acc      576
Thr Gly Lys Ser Asn Ser Arg Ser Met Pro Leu Glu Trp Glu Asp Thr
            180                 185                 190 tat gga att gtc ctg ctt tct gga gtg aag tat aag aag ggt ggc ctt      624
Tyr Gly Ile Val Leu Leu Ser Gly Val Lys Tyr Lys Lys Gly Gly Leu
        195                 200                 205 gtg atc aat gaa act ggg ctg tac ttt gta tat tcc aaa gta tac ttc      672
Val Ile Asn Glu Thr Gly Leu Tyr Phe Val Tyr Ser Lys Val Tyr Phe
    210                 215                 220 cgg ggt caa tct tgc aac aac ctg ccc ctg agc cac aag gtc tac atg      720
Arg Gly Gln Ser Cys Asn Asn Leu Pro Leu Ser His Lys Val Tyr Met
225                 230                 235                 240 agg aac tct aag tat ccc cag gat ctg gtg atg atg gag ggg aag atg      768
Arg Asn Ser Lys Tyr Pro Gln Asp Leu Val Met Met Glu Gly Lys Met
                245                 250                 255 atg agc tac tgc act act ggg cag atg tgg gcc cgc agc agc tac ctg      816
Met Ser Tyr Cys Thr Thr Gly Gln Met Trp Ala Arg Ser Ser Tyr Leu
            260                 265                 270 ggg gca gtg ttc aat ctt acc agt gct gat cat tta tat gtc aac gta      864
Gly Ala Val Phe Asn Leu Thr Ser Ala Asp His Leu Tyr Val Asn Val
        275                 280                 285 tct gag ctc tct ctg gtc aat ttt gag gaa tct cag acg ttt ttc ggc      912
Ser Glu Leu Ser Leu Val Asn Phe Glu Glu Ser Gln Thr Phe Phe Gly
    290                 295                 300 tta tat aag ctc taa                                                  927
Leu Tyr Lys Leu
305

<210> SEQ ID NO 2
<211> LENGTH: 308
<212> TYPE: PRT
<213> ORGANISM: Artificial
<220> FEATURE:
<223> OTHER INFORMATION: Synthetic Construct

<400> SEQUENCE: 2

Met Met Asp Ile Tyr Val Cys Leu Lys Arg Pro Ser Trp Met Val Asp
1               5                   10                  15

Asn Lys Arg Met Arg Thr Ala Ser Asn Phe Gln Trp Leu Leu Ser Thr
            20                  25                  30

Phe Ile Leu Leu Tyr Leu Met Asn Gln Val Asn Ser Gln Lys Lys Thr
        35                  40                  45

Ser Ile Pro Asp Ser Gln Thr Lys Val Phe Pro Gln Asp Lys Val Ile
    50                  55                  60

Leu Val Gly Ser Asp Ile Thr Phe Cys Cys Val Ser Gln Glu Lys Val
65                  70                  75                  80

Leu Ser Ala Leu Ile Gly His Thr Asn Cys Pro Leu Ile His Leu Asp
                85                  90                  95

Gly Glu Asn Val Ala Ile Lys Ile Arg Asn Ile Ser Val Ser Ala Ser
            100                 105                 110

Ser Gly Thr Asn Val Val Phe Thr Thr Glu Asp Asn Ile Phe Gly Thr
        115                 120                 125
```

```
Val Ile Ser Arg Ala Leu Gln Lys Glu Leu Ala Glu Leu Arg Glu Ser
    130                 135                 140

Thr Ser Gln Met His Thr Ala Ser Ser Leu Glu Lys Gln Ile Gly His
145                 150                 155                 160

Pro Ser Pro Pro Glu Lys Lys Glu Leu Arg Lys Val Ala His Leu
                165                 170                 175

Thr Gly Lys Ser Asn Ser Arg Ser Met Pro Leu Glu Trp Glu Asp Thr
            180                 185                 190

Tyr Gly Ile Val Leu Leu Ser Gly Val Lys Tyr Lys Lys Gly Gly Leu
                195                 200                 205

Val Ile Asn Glu Thr Gly Leu Tyr Phe Val Tyr Ser Lys Val Tyr Phe
    210                 215                 220

Arg Gly Gln Ser Cys Asn Asn Leu Pro Leu Ser His Lys Val Tyr Met
225                 230                 235                 240

Arg Asn Ser Lys Tyr Pro Gln Asp Leu Val Met Met Glu Gly Lys Met
                245                 250                 255

Met Ser Tyr Cys Thr Thr Gly Gln Met Trp Ala Arg Ser Ser Tyr Leu
            260                 265                 270

Gly Ala Val Phe Asn Leu Thr Ser Ala Asp His Leu Tyr Val Asn Val
                275                 280                 285

Ser Glu Leu Ser Leu Val Asn Phe Glu Glu Ser Gln Thr Phe Phe Gly
    290                 295                 300

Leu Tyr Lys Leu
305

<210> SEQ ID NO 3
<211> LENGTH: 243
<212> TYPE: DNA
<213> ORGANISM: Artificial
<220> FEATURE:
<223> OTHER INFORMATION: Ig-like module of human gp190
<220> FEATURE:
<221> NAME/KEY: CDS
<222> LOCATION: (1)..(243)

<400> SEQUENCE: 3 ata cct gat tct cag act aag gtt ttt cct caa gat aaa gtg ata ctt      48
Ile Pro Asp Ser Gln Thr Lys Val Phe Pro Gln Asp Lys Val Ile Leu
1               5                   10                  15 gta ggc tca gac ata aca ttt tgt tgt gtg agt caa gaa aaa gtg tta      96
Val Gly Ser Asp Ile Thr Phe Cys Cys Val Ser Gln Glu Lys Val Leu
            20                  25                  30 tca gca ctg att ggc cat aca aac tgc ccc ttg atc cat ctt gat ggg     144
Ser Ala Leu Ile Gly His Thr Asn Cys Pro Leu Ile His Leu Asp Gly
        35                  40                  45 gaa aat gtt gca atc aag att cgt aat att tct gtt tct gca agt agt     192
Glu Asn Val Ala Ile Lys Ile Arg Asn Ile Ser Val Ser Ala Ser Ser
    50                  55                  60 gga aca aat gta gtt ttt aca acc gaa gat aac ata ttt gga acc gtt     240
Gly Thr Asn Val Val Phe Thr Thr Glu Asp Asn Ile Phe Gly Thr Val
65                  70                  75                  80 att                                                                 243
Ile

<210> SEQ ID NO 4
<211> LENGTH: 81
<212> TYPE: PRT
<213> ORGANISM: Artificial
<220> FEATURE:
<223> OTHER INFORMATION: Synthetic Construct
```

-continued

<400> SEQUENCE: 4

Ile Pro Asp Ser Gln Thr Lys Val Phe Pro Gln Asp Lys Val Ile Leu
1               5                   10                  15

Val Gly Ser Asp Ile Thr Phe Cys Cys Val Ser Gln Glu Lys Val Leu
            20                  25                  30

Ser Ala Leu Ile Gly His Thr Asn Cys Pro Leu Ile His Leu Asp Gly
        35                  40                  45

Glu Asn Val Ala Ile Lys Ile Arg Asn Ile Ser Val Ser Ala Ser Ser
    50                  55                  60

Gly Thr Asn Val Val Phe Thr Thr Glu Asp Asn Ile Phe Gly Thr Val
65                  70                  75                  80

Ile

<210> SEQ ID NO 5
<211> LENGTH: 9
<212> TYPE: DNA
<213> ORGANISM: Artificial
<220> FEATURE:
<223> OTHER INFORMATION: Linker

<400> SEQUENCE: 5 tctagagcc                                                                 9

<210> SEQ ID NO 6
<211> LENGTH: 3
<212> TYPE: PRT
<213> ORGANISM: Artificial
<220> FEATURE:
<223> OTHER INFORMATION: Linker

<400> SEQUENCE: 6

Ser Arg Ala
1

<210> SEQ ID NO 7
<211> LENGTH: 528
<212> TYPE: DNA
<213> ORGANISM: Artificial
<220> FEATURE:
<223> OTHER INFORMATION: sFasL
<220> FEATURE:
<221> NAME/KEY: CDS
<222> LOCATION: (1)..(528)

<400> SEQUENCE: 7 cta cag aag gag ctg gca gaa ctc cga gag tct acc agc cag atg cac     48
Leu Gln Lys Glu Leu Ala Glu Leu Arg Glu Ser Thr Ser Gln Met His
1               5                   10                  15 aca gca tca tct ttg gag aag caa ata ggc cac ccc agt cca ccc cct     96
Thr Ala Ser Ser Leu Glu Lys Gln Ile Gly His Pro Ser Pro Pro Pro
            20                  25                  30 gaa aaa aag gag ctg agg aaa gtg gcc cat tta aca ggc aag tcc aac    144
Glu Lys Lys Glu Leu Arg Lys Val Ala His Leu Thr Gly Lys Ser Asn
        35                  40                  45 tca agg tcc atg cct ctg gaa tgg gaa gac acc tat gga att gtc ctg    192
Ser Arg Ser Met Pro Leu Glu Trp Glu Asp Thr Tyr Gly Ile Val Leu
    50                  55                  60 ctt tct gga gtg aag tat aag aag ggt ggc ctt gtg atc aat gaa act    240
Leu Ser Gly Val Lys Tyr Lys Lys Gly Gly Leu Val Ile Asn Glu Thr
65                  70                  75                  80 ggg ctg tac ttt gta tat tcc aaa gta tac ttc cgg ggt caa tct tgc    288

```
Gly Leu Tyr Phe Val Tyr Ser Lys Val Tyr Phe Arg Gly Gln Ser Cys
                    85                  90                  95 aac aac ctg ccc ctg agc cac aag gtc tac atg agg aac tct aag tat     336
Asn Asn Leu Pro Leu Ser His Lys Val Tyr Met Arg Asn Ser Lys Tyr
            100                 105                 110 ccc cag gat ctg gtg atg atg gag ggg aag atg atg agc tac tgc act     384
Pro Gln Asp Leu Val Met Met Glu Gly Lys Met Met Ser Tyr Cys Thr
            115                 120                 125 act ggg cag atg tgg gcc cgc agc agc tac ctg ggg gca gtg ttc aat     432
Thr Gly Gln Met Trp Ala Arg Ser Ser Tyr Leu Gly Ala Val Phe Asn
        130                 135                 140 ctt acc agt gct gat cat tta tat gtc aac gta tct gag ctc tct ctg     480
Leu Thr Ser Ala Asp His Leu Tyr Val Asn Val Ser Glu Leu Ser Leu
145                 150                 155                 160 gtc aat ttt gag gaa tct cag acg ttt ttc ggc tta tat aag ctc taa     528
Val Asn Phe Glu Glu Ser Gln Thr Phe Phe Gly Leu Tyr Lys Leu
                165                 170                 175
```

<210> SEQ ID NO 8
<211> LENGTH: 175
<212> TYPE: PRT
<213> ORGANISM: Artificial
<220> FEATURE:
<223> OTHER INFORMATION: Synthetic Construct

<400> SEQUENCE: 8

```
Leu Gln Lys Glu Leu Ala Glu Leu Arg Glu Ser Thr Ser Gln Met His
1               5                   10                  15

Thr Ala Ser Ser Leu Glu Lys Gln Ile Gly His Pro Ser Pro Pro Pro
            20                  25                  30

Glu Lys Lys Glu Leu Arg Lys Val Ala His Leu Thr Gly Lys Ser Asn
        35                  40                  45

Ser Arg Ser Met Pro Leu Glu Trp Glu Asp Thr Tyr Gly Ile Val Leu
    50                  55                  60

Leu Ser Gly Val Lys Tyr Lys Lys Gly Gly Leu Val Ile Asn Glu Thr
65                  70                  75                  80

Gly Leu Tyr Phe Val Tyr Ser Lys Val Tyr Phe Arg Gly Gln Ser Cys
                85                  90                  95

Asn Asn Leu Pro Leu Ser His Lys Val Tyr Met Arg Asn Ser Lys Tyr
            100                 105                 110

Pro Gln Asp Leu Val Met Met Glu Gly Lys Met Met Ser Tyr Cys Thr
        115                 120                 125

Thr Gly Gln Met Trp Ala Arg Ser Ser Tyr Leu Gly Ala Val Phe Asn
    130                 135                 140

Leu Thr Ser Ala Asp His Leu Tyr Val Asn Val Ser Glu Leu Ser Leu
145                 150                 155                 160

Val Asn Phe Glu Glu Ser Gln Thr Phe Phe Gly Leu Tyr Lys Leu
                165                 170                 175
```

<210> SEQ ID NO 9
<211> LENGTH: 147
<212> TYPE: DNA
<213> ORGANISM: Artificial
<220> FEATURE:
<223> OTHER INFORMATION: Secretion signal peptide
<220> FEATURE:
<221> NAME/KEY: CDS
<222> LOCATION: (1)..(147)

<400> SEQUENCE: 9

```
atg atg gat att tac gta tgt ttg aaa cga cca tcc tgg atg gtg gac      48
Met Met Asp Ile Tyr Val Cys Leu Lys Arg Pro Ser Trp Met Val Asp
1               5                   10                  15 aat aaa aga atg agg act gct tca aat ttc cag tgg ctg tta tca aca      96
Asn Lys Arg Met Arg Thr Ala Ser Asn Phe Gln Trp Leu Leu Ser Thr
                20                  25                  30 ttt att ctt cta tat cta atg aat caa gta aat agc cag aaa aag act     144
Phe Ile Leu Leu Tyr Leu Met Asn Gln Val Asn Ser Gln Lys Lys Thr
            35                  40                  45 agt                                                                  147
Ser

<210> SEQ ID NO 10
<211> LENGTH: 49
<212> TYPE: PRT
<213> ORGANISM: Artificial
<220> FEATURE:
<223> OTHER INFORMATION: Synthetic Construct

<400> SEQUENCE: 10

Met Met Asp Ile Tyr Val Cys Leu Lys Arg Pro Ser Trp Met Val Asp
1               5                   10                  15

Asn Lys Arg Met Arg Thr Ala Ser Asn Phe Gln Trp Leu Leu Ser Thr
                20                  25                  30

Phe Ile Leu Leu Tyr Leu Met Asn Gln Val Asn Ser Gln Lys Lys Thr
            35                  40                  45

Ser

<210> SEQ ID NO 11
<211> LENGTH: 780
<212> TYPE: DNA
<213> ORGANISM: Artificial
<220> FEATURE:
<223> OTHER INFORMATION: IgFasL chimeric gene (without signal peptide)
<220> FEATURE:
<221> NAME/KEY: CDS
<222> LOCATION: (1)..(780)

<400> SEQUENCE: 11 ata cct gat tct cag act aag gtt ttt cct caa gat aaa gtg ata ctt      48
Ile Pro Asp Ser Gln Thr Lys Val Phe Pro Gln Asp Lys Val Ile Leu
1               5                   10                  15 gta ggc tca gac ata aca ttt tgt tgt gtg agt caa gaa aaa gtg tta      96
Val Gly Ser Asp Ile Thr Phe Cys Cys Val Ser Gln Glu Lys Val Leu
                20                  25                  30 tca gca ctg att ggc cat aca aac tgc ccc ttg atc cat ctt gat ggg     144
Ser Ala Leu Ile Gly His Thr Asn Cys Pro Leu Ile His Leu Asp Gly
            35                  40                  45 gaa aat gtt gca atc aag att cgt aat att tct gtt tct gca agt agt     192
Glu Asn Val Ala Ile Lys Ile Arg Asn Ile Ser Val Ser Ala Ser Ser
        50                  55                  60 gga aca aat gta gtt ttt aca acc gaa gat aac ata ttt gga acc gtt     240
Gly Thr Asn Val Val Phe Thr Thr Glu Asp Asn Ile Phe Gly Thr Val
65                  70                  75                  80 att tct aga gcc cta cag aag gag ctg gca gaa ctc cga gag tct acc     288
Ile Ser Arg Ala Leu Gln Lys Glu Leu Ala Glu Leu Arg Glu Ser Thr
                85                  90                  95 agc cag atg cac aca gca tca tct ttg gag aag caa ata ggc cac ccc     336
Ser Gln Met His Thr Ala Ser Ser Leu Glu Lys Gln Ile Gly His Pro
            100                 105                 110 agt cca ccc cct gaa aaa aag gag ctg agg aaa gtg gcc cat tta aca     384
Ser Pro Pro Pro Glu Lys Lys Glu Leu Arg Lys Val Ala His Leu Thr
```

```
            115                 120                 125
ggc aag tcc aac tca agg tcc atg cct ctg gaa tgg gaa gac acc tat     432
Gly Lys Ser Asn Ser Arg Ser Met Pro Leu Glu Trp Glu Asp Thr Tyr
        130                 135                 140 gga att gtc ctg ctt tct gga gtg aag tat aag aag ggt ggc ctt gtg     480
Gly Ile Val Leu Leu Ser Gly Val Lys Tyr Lys Lys Gly Gly Leu Val
145                 150                 155                 160 atc aat gaa act ggg ctg tac ttt gta tat tcc aaa gta tac ttc cgg     528
Ile Asn Glu Thr Gly Leu Tyr Phe Val Tyr Ser Lys Val Tyr Phe Arg
                165                 170                 175 ggt caa tct tgc aac aac ctg ccc ctg agc cac aag gtc tac atg agg     576
Gly Gln Ser Cys Asn Asn Leu Pro Leu Ser His Lys Val Tyr Met Arg
            180                 185                 190 aac tct aag tat ccc cag gat ctg gtg atg atg gag ggg aag atg atg     624
Asn Ser Lys Tyr Pro Gln Asp Leu Val Met Met Glu Gly Lys Met Met
        195                 200                 205 agc tac tgc act act ggg cag atg tgg gcc cgc agc agc tac ctg ggg     672
Ser Tyr Cys Thr Thr Gly Gln Met Trp Ala Arg Ser Ser Tyr Leu Gly
    210                 215                 220 gca gtg ttc aat ctt acc agt gct gat cat tta tat gtc aac gta tct     720
Ala Val Phe Asn Leu Thr Ser Ala Asp His Leu Tyr Val Asn Val Ser
225                 230                 235                 240 gag ctc tct ctg gtc aat ttt gag gaa tct cag acg ttt ttc ggc tta     768
Glu Leu Ser Leu Val Asn Phe Glu Glu Ser Gln Thr Phe Phe Gly Leu
                245                 250                 255 tat aag ctc taa                                                     780
Tyr Lys Leu <210> SEQ ID NO 12
<211> LENGTH: 259
<212> TYPE: PRT
<213> ORGANISM: Artificial
<220> FEATURE:
<223> OTHER INFORMATION: Synthetic Construct

<400> SEQUENCE: 12

Ile Pro Asp Ser Gln Thr Lys Val Phe Pro Gln Asp Lys Val Ile Leu
1               5                   10                  15

Val Gly Ser Asp Ile Thr Phe Cys Cys Val Ser Gln Glu Lys Val Leu
                20                  25                  30

Ser Ala Leu Ile Gly His Thr Asn Cys Pro Leu Ile His Leu Asp Gly
            35                  40                  45

Glu Asn Val Ala Ile Lys Ile Arg Asn Ile Ser Val Ser Ala Ser Ser
        50                  55                  60

Gly Thr Asn Val Val Phe Thr Thr Glu Asp Asn Ile Phe Gly Thr Val
65                  70                  75                  80

Ile Ser Arg Ala Leu Gln Lys Glu Leu Ala Glu Leu Arg Glu Ser Thr
                85                  90                  95

Ser Gln Met His Thr Ala Ser Ser Leu Glu Lys Gln Ile Gly His Pro
            100                 105                 110

Ser Pro Pro Pro Glu Lys Lys Glu Leu Arg Lys Val Ala His Leu Thr
        115                 120                 125

Gly Lys Ser Asn Ser Arg Ser Met Pro Leu Glu Trp Glu Asp Thr Tyr
    130                 135                 140

Gly Ile Val Leu Leu Ser Gly Val Lys Tyr Lys Lys Gly Gly Leu Val
145                 150                 155                 160

Ile Asn Glu Thr Gly Leu Tyr Phe Val Tyr Ser Lys Val Tyr Phe Arg
                165                 170                 175
```

-continued

```
Gly Gln Ser Cys Asn Asn Leu Pro Leu Ser His Lys Val Tyr Met Arg
            180                 185                 190

Asn Ser Lys Tyr Pro Gln Asp Leu Val Met Met Glu Gly Lys Met Met
        195                 200                 205

Ser Tyr Cys Thr Thr Gly Gln Met Trp Ala Arg Ser Ser Tyr Leu Gly
    210                 215                 220

Ala Val Phe Asn Leu Thr Ser Ala Asp His Leu Tyr Val Asn Val Ser
225                 230                 235                 240

Glu Leu Ser Leu Val Asn Phe Glu Glu Ser Gln Thr Phe Phe Gly Leu
                245                 250                 255

Tyr Lys Leu

<210> SEQ ID NO 13
<211> LENGTH: 972
<212> TYPE: DNA
<213> ORGANISM: Homo sapiens
<220> FEATURE:
<221> NAME/KEY: mRNA - Human Fas Ligand (FasL)
<222> LOCATION: (1)..(972)
<220> FEATURE:
<221> NAME/KEY: CDS
<222> LOCATION: (65)..(910)

<400> SEQUENCE: 13
tctagactca ggactgagaa gaagtaaaac cgtttgctgg ggctggcctg actcaccagc       60 tgcc atg cag cag ccc ttc aat tac cca tat ccc cag atc tac tgg gtg      109
     Met Gln Gln Pro Phe Asn Tyr Pro Tyr Pro Gln Ile Tyr Trp Val
     1               5                   10                  15 gac agc agt gcc agc tct ccc tgg gcc cct cca ggc aca gtt ctt ccc      157
Asp Ser Ser Ala Ser Ser Pro Trp Ala Pro Pro Gly Thr Val Leu Pro
                20                  25                  30 tgt cca acc tct gtg ccc aga agg cct ggt caa agg agg cca cca cca      205
Cys Pro Thr Ser Val Pro Arg Arg Pro Gly Gln Arg Arg Pro Pro Pro
            35                  40                  45 cca ccg cca ccg cca cca cta cca cct ccg ccg ccg cca cca ctg          253
Pro Pro Pro Pro Pro Pro Leu Pro Pro Pro Pro Pro Pro Pro Leu
        50                  55                  60 cct cca cta ccg ctg cca ccc ctg aag aag aga ggg aac cac agc aca      301
Pro Pro Leu Pro Leu Pro Pro Leu Lys Lys Arg Gly Asn His Ser Thr
65                  70                  75 ggc ctg tgt ctc ctt gtg atg ttt ttc atg gtt ctg gtt gcc ttg gta      349
Gly Leu Cys Leu Leu Val Met Phe Phe Met Val Leu Val Ala Leu Val
80                  85                  90                  95 gga ttg ggc ctg ggg atg ttt cag ctc ttc cac cta cag aag gag ctg      397
Gly Leu Gly Leu Gly Met Phe Gln Leu Phe His Leu Gln Lys Glu Leu
                100                 105                 110 gca gaa ctc cga gag tct acc agc cag atg cac aca gca tca tct ttg      445
Ala Glu Leu Arg Glu Ser Thr Ser Gln Met His Thr Ala Ser Ser Leu
            115                 120                 125 gag aag caa ata ggc cac ccc agt cca ccc cct gaa aaa aag gag ctg      493
Glu Lys Gln Ile Gly His Pro Ser Pro Pro Pro Glu Lys Lys Glu Leu
        130                 135                 140 agg aaa gtg gcc cat tta aca ggc aag tcc aac tca agg tcc atg cct      541
Arg Lys Val Ala His Leu Thr Gly Lys Ser Asn Ser Arg Ser Met Pro
145                 150                 155 ctg gaa tgg gaa gac acc tat gga att gtc ctg ctt tct gga gtg aag      589
Leu Glu Trp Glu Asp Thr Tyr Gly Ile Val Leu Leu Ser Gly Val Lys
160                 165                 170                 175 tat aag aag ggt ggc ctt gtg atc aat gaa act ggg ctg tac ttt gta      637
```

|  |  |  |  |  |  |  |  |  |  |  |  |  |  |  |
|---|---|---|---|---|---|---|---|---|---|---|---|---|---|---|
| Tyr | Lys | Lys | Gly | Gly | Leu | Val | Ile | Asn | Glu | Thr | Gly | Leu | Tyr | Phe | Val |
|  |  |  |  | 180 |  |  |  | 185 |  |  |  | 190 |  |  |

```
tat tcc aaa gta tac ttc cgg ggt caa tct tgc aac aac ctg ccc ctg       685
Tyr Ser Lys Val Tyr Phe Arg Gly Gln Ser Cys Asn Asn Leu Pro Leu
        195                 200                 205 agc cac aag gtc tac atg agg aac tct aag tat ccc cag gat ctg gtg       733
Ser His Lys Val Tyr Met Arg Asn Ser Lys Tyr Pro Gln Asp Leu Val
        210                 215                 220 atg atg gag ggg aag atg atg agc tac tgc act act ggg cag atg tgg       781
Met Met Glu Gly Lys Met Met Ser Tyr Cys Thr Thr Gly Gln Met Trp
225                 230                 235 gcc cgc agc agc tac ctg ggg gca gtg ttc aat ctt acc agt gct gat       829
Ala Arg Ser Ser Tyr Leu Gly Ala Val Phe Asn Leu Thr Ser Ala Asp
240                 245                 250                 255 cat tta tat gtc aac gta tct gag ctc tct ctg gtc aat ttt gag gaa       877
His Leu Tyr Val Asn Val Ser Glu Leu Ser Leu Val Asn Phe Glu Glu
                260                 265                 270 tct cag acg ttt ttc ggc tta tat aag ctc taa gagaagcact ttgggattct     930
Ser Gln Thr Phe Phe Gly Leu Tyr Lys Leu
                275                 280 ttccattatg attctttgtt acaggcaccg agatgttcta ga                        972

<210> SEQ ID NO 14
<211> LENGTH: 281
<212> TYPE: PRT
<213> ORGANISM: Homo sapiens

<400> SEQUENCE: 14

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220
```

```
Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
            245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
            275                 280

<210> SEQ ID NO 15
<211> LENGTH: 726
<212> TYPE: DNA
<213> ORGANISM: Homo sapiens
<220> FEATURE:
<221> NAME/KEY: misc_feature
<222> LOCATION: (1)..(726)
<223> OTHER INFORMATION: human CD80 cDNA, extracellular region
<220> FEATURE:
<221> NAME/KEY: CDS
<222> LOCATION: (1)..(726)

<400> SEQUENCE: 15 atg ggc cac aca cgg agg cag gga aca tca cca tcc aag tgt cca tac      48
Met Gly His Thr Arg Arg Gln Gly Thr Ser Pro Ser Lys Cys Pro Tyr
1               5                   10                  15 ctc aat ttc ttt cag ctc ttg gtg ctg gct ggt ctt tct cac ttc tgt      96
Leu Asn Phe Phe Gln Leu Leu Val Leu Ala Gly Leu Ser His Phe Cys
            20                  25                  30 tca ggt gtt atc cac gtg acc aag gaa gtg aaa gaa gtg gca acg ctg     144
Ser Gly Val Ile His Val Thr Lys Glu Val Lys Glu Val Ala Thr Leu
        35                  40                  45 tcc tgt ggt cac aat gtt tct gtt gaa gag ctg gca caa act cgc atc     192
Ser Cys Gly His Asn Val Ser Val Glu Glu Leu Ala Gln Thr Arg Ile
    50                  55                  60 tac tgg caa aag gag aag aaa atg gtg ctg act atg atg tct ggg gac     240
Tyr Trp Gln Lys Glu Lys Lys Met Val Leu Thr Met Met Ser Gly Asp
65                  70                  75                  80 atg aat ata tgg ccc gag tac aag aac cgg acc atc ttt gat atc act     288
Met Asn Ile Trp Pro Glu Tyr Lys Asn Arg Thr Ile Phe Asp Ile Thr
                85                  90                  95 aat aac ctc tcc att gtg atc ctg gct ctg cgc cca tct gac gag ggc     336
Asn Asn Leu Ser Ile Val Ile Leu Ala Leu Arg Pro Ser Asp Glu Gly
            100                 105                 110 aca tac gag tgt gtt gtt ctg aag tat gaa aaa gac gct ttc aag cgg     384
Thr Tyr Glu Cys Val Val Leu Lys Tyr Glu Lys Asp Ala Phe Lys Arg
        115                 120                 125 gaa cac ctg gct gaa gtg acg tta tca gtc aaa gct gac ttc cct aca     432
Glu His Leu Ala Glu Val Thr Leu Ser Val Lys Ala Asp Phe Pro Thr
    130                 135                 140 cct agt ata tct gac ttt gaa att cca act tct aat att aga agg ata     480
Pro Ser Ile Ser Asp Phe Glu Ile Pro Thr Ser Asn Ile Arg Arg Ile
145                 150                 155                 160 att tgc tca acc tct gga ggt ttt cca gag cct cac ctc tcc tgg ttg     528
Ile Cys Ser Thr Ser Gly Gly Phe Pro Glu Pro His Leu Ser Trp Leu
                165                 170                 175 gaa aat gga gaa gaa tta aat gcc atc aac aca aca gtt tcc caa gat     576
Glu Asn Gly Glu Glu Leu Asn Ala Ile Asn Thr Thr Val Ser Gln Asp
            180                 185                 190 cct gaa act gag ctc tat gct gtt agc agc aaa ctg gat ttc aat atg     624
Pro Glu Thr Glu Leu Tyr Ala Val Ser Ser Lys Leu Asp Phe Asn Met
        195                 200                 205
```

```
aca acc aac cac agc ttc atg tgt ctc atc aag tat gga cat tta aga       672
Thr Thr Asn His Ser Phe Met Cys Leu Ile Lys Tyr Gly His Leu Arg
210             215                 220 gtg aat cag acc ttc aac tgg aat aca acc aag caa gag cat ttt cct       720
Val Asn Gln Thr Phe Asn Trp Asn Thr Thr Lys Gln Glu His Phe Pro
225             230                 235                 240 tct aga                                                               726
Ser Arg <210> SEQ ID NO 16
<211> LENGTH: 242
<212> TYPE: PRT
<213> ORGANISM: Homo sapiens

<400> SEQUENCE: 16

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Ser Arg

<210> SEQ ID NO 17
<211> LENGTH: 1506
<212> TYPE: DNA
<213> ORGANISM: Artificial Sequence
<220> FEATURE:
<223> OTHER INFORMATION: CD80 IgFasL
<220> FEATURE:
<221> NAME/KEY: CDS
<222> LOCATION: (1)..(1506)
<220> FEATURE:
<221> NAME/KEY: misc_feature
<222> LOCATION: (1)..(1506)
```

<223> OTHER INFORMATION: complete sequence

<400> SEQUENCE: 17

| | | | | | | | | | | | | | | | | |
|---|---|---|---|---|---|---|---|---|---|---|---|---|---|---|---|---|
| atg | ggc | cac | aca | cgg | agg | cag | gga | aca | tca | cca | tcc | aag | tgt | cca | tac | 48 |
| Met | Gly | His | Thr | Arg | Arg | Gln | Gly | Thr | Ser | Pro | Ser | Lys | Cys | Pro | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctc | aat | ttc | ttt | cag | ctc | ttg | gtg | ctg | gct | ggt | ctt | tct | cac | ttc | tgt | 96 |
| Leu | Asn | Phe | Phe | Gln | Leu | Leu | Val | Leu | Ala | Gly | Leu | Ser | His | Phe | Cys | |
| | | | 20 | | | | | 25 | | | | | 30 | | | |

| | | | | | | | | | | | | | | | | |
|---|---|---|---|---|---|---|---|---|---|---|---|---|---|---|---|---|
| tca | ggt | gtt | atc | cac | gtg | acc | aag | gaa | gtg | aaa | gaa | gtg | gca | acg | ctg | 144 |
| Ser | Gly | Val | Ile | His | Val | Thr | Lys | Glu | Val | Lys | Glu | Val | Ala | Thr | Leu | |
| | | | 35 | | | | | 40 | | | | | 45 | | | |

| | | | | | | | | | | | | | | | | |
|---|---|---|---|---|---|---|---|---|---|---|---|---|---|---|---|---|
| tcc | tgt | ggt | cac | aat | gtt | tct | gtt | gaa | gag | ctg | gca | caa | act | cgc | atc | 192 |
| Ser | Cys | Gly | His | Asn | Val | Ser | Val | Glu | Glu | Leu | Ala | Gln | Thr | Arg | Ile | |
| | | 50 | | | | | 55 | | | | | 60 | | | | |

| | | | | | | | | | | | | | | | | |
|---|---|---|---|---|---|---|---|---|---|---|---|---|---|---|---|---|
| tac | tgg | caa | aag | gag | aag | aaa | atg | gtg | ctg | act | atg | atg | tct | ggg | gac | 240 |
| Tyr | Trp | Gln | Lys | Glu | Lys | Lys | Met | Val | Leu | Thr | Met | Met | Ser | Gly | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | aat | ata | tgg | ccc | gag | tac | aag | aac | cgg | acc | atc | ttt | gat | atc | act | 288 |
| Met | Asn | Ile | Trp | Pro | Glu | Tyr | Lys | Asn | Arg | Thr | Ile | Phe | Asp | Ile | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | aac | ctc | tcc | att | gtg | atc | ctg | gct | ctg | cgc | cca | tct | gac | gag | ggc | 336 |
| Asn | Asn | Leu | Ser | Ile | Val | Ile | Leu | Ala | Leu | Arg | Pro | Ser | Asp | Glu | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| aca | tac | gag | tgt | gtt | gtt | ctg | aag | tat | gaa | aaa | gac | gct | ttc | aag | cgg | 384 |
| Thr | Tyr | Glu | Cys | Val | Val | Leu | Lys | Tyr | Glu | Lys | Asp | Ala | Phe | Lys | Arg | |
| | | | 115 | | | | | 120 | | | | | 125 | | | |

| | | | | | | | | | | | | | | | | |
|---|---|---|---|---|---|---|---|---|---|---|---|---|---|---|---|---|
| gaa | cac | ctg | gct | gaa | gtg | acg | tta | tca | gtc | aaa | gct | gac | ttc | cct | aca | 432 |
| Glu | His | Leu | Ala | Glu | Val | Thr | Leu | Ser | Val | Lys | Ala | Asp | Phe | Pro | Thr | |
| | | 130 | | | | | 135 | | | | | 140 | | | | |

| | | | | | | | | | | | | | | | | |
|---|---|---|---|---|---|---|---|---|---|---|---|---|---|---|---|---|
| cct | agt | ata | tct | gac | ttt | gaa | att | cca | act | tct | aat | att | aga | agg | ata | 480 |
| Pro | Ser | Ile | Ser | Asp | Phe | Glu | Ile | Pro | Thr | Ser | Asn | Ile | Arg | Arg | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| att | tgc | tca | acc | tct | gga | ggt | ttt | cca | gag | cct | cac | ctc | tcc | tgg | ttg | 528 |
| Ile | Cys | Ser | Thr | Ser | Gly | Gly | Phe | Pro | Glu | Pro | His | Leu | Ser | Trp | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | aat | gga | gaa | gaa | tta | aat | gcc | atc | aac | aca | aca | gtt | tcc | caa | gat | 576 |
| Glu | Asn | Gly | Glu | Glu | Leu | Asn | Ala | Ile | Asn | Thr | Thr | Val | Ser | Gln | Asp | |
| | | | | 180 | | | | | 185 | | | | | 190 | | |

| | | | | | | | | | | | | | | | | |
|---|---|---|---|---|---|---|---|---|---|---|---|---|---|---|---|---|
| cct | gaa | act | gag | ctc | tat | gct | gtt | agc | agc | aaa | ctg | gat | ttc | aat | atg | 624 |
| Pro | Glu | Thr | Glu | Leu | Tyr | Ala | Val | Ser | Ser | Lys | Leu | Asp | Phe | Asn | Met | |
| | | | 195 | | | | | 200 | | | | | 205 | | | |

| | | | | | | | | | | | | | | | | |
|---|---|---|---|---|---|---|---|---|---|---|---|---|---|---|---|---|
| aca | acc | aac | cac | agc | ttc | atg | tgt | ctc | atc | aag | tat | gga | cat | tta | aga | 672 |
| Thr | Thr | Asn | His | Ser | Phe | Met | Cys | Leu | Ile | Lys | Tyr | Gly | His | Leu | Arg | |
| | | 210 | | | | | 215 | | | | | 220 | | | | |

| | | | | | | | | | | | | | | | | |
|---|---|---|---|---|---|---|---|---|---|---|---|---|---|---|---|---|
| gtg | aat | cag | acc | ttc | aac | tgg | aat | aca | acc | aag | caa | gag | cat | ttt | cct | 720 |
| Val | Asn | Gln | Thr | Phe | Asn | Trp | Asn | Thr | Thr | Lys | Gln | Glu | His | Phe | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tct | agt | ata | cct | gat | tct | cag | act | aag | gtt | ttt | cct | caa | gat | aaa | gtg | 768 |
| Ser | Ser | Ile | Pro | Asp | Ser | Gln | Thr | Lys | Val | Phe | Pro | Gln | Asp | Lys | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| ata | ctt | gta | ggc | tca | gac | ata | aca | ttt | tgt | tgt | gtg | agt | caa | gaa | aaa | 816 |
| Ile | Leu | Val | Gly | Ser | Asp | Ile | Thr | Phe | Cys | Cys | Val | Ser | Gln | Glu | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| gtg | tta | tca | gca | ctg | att | ggc | cat | aca | aac | tgc | ccc | ttg | atc | cat | ctt | 864 |
| Val | Leu | Ser | Ala | Leu | Ile | Gly | His | Thr | Asn | Cys | Pro | Leu | Ile | His | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| gat | ggg | gaa | aat | gtt | gca | atc | aag | att | cgt | aat | att | tct | gtt | tct | gca | 912 |
| Asp | Gly | Glu | Asn | Val | Ala | Ile | Lys | Ile | Arg | Asn | Ile | Ser | Val | Ser | Ala | |
| | | 290 | | | | | 295 | | | | | 300 | | | | |

-continued

| | | |
|---|---|---|
| agt agt gga aca aat gta gtt ttt aca acc gaa gat aac ata ttt gga<br>Ser Ser Gly Thr Asn Val Val Phe Thr Thr Glu Asp Asn Ile Phe Gly<br>305                       310                       315                   320 | 960 |
| acc gtt att tct aga gcc cta cag aag gag ctg gca gaa ctc cga gag<br>Thr Val Ile Ser Arg Ala Leu Gln Lys Glu Leu Ala Glu Leu Arg Glu<br>                      325                       330                       335 | 1008 |
| tct acc agc cag atg cac aca gca tca tct ttg gag aag caa ata ggc<br>Ser Thr Ser Gln Met His Thr Ala Ser Ser Leu Glu Lys Gln Ile Gly<br>                      340                       345                       350 | 1056 |
| cac ccc agt cca ccc cct gaa aaa aag gag ctg agg aaa gtg gcc cat<br>His Pro Ser Pro Pro Pro Glu Lys Lys Glu Leu Arg Lys Val Ala His<br>                 355                       360                       365 | 1104 |
| tta aca ggc aag tcc aac tca agg tcc atg cct ctg gaa tgg gaa gac<br>Leu Thr Gly Lys Ser Asn Ser Arg Ser Met Pro Leu Glu Trp Glu Asp<br>370                       375                       380 | 1152 |
| acc tat gga att gtc ctg ctt tct gga gtg aag tat aag aag ggt ggc<br>Thr Tyr Gly Ile Val Leu Leu Ser Gly Val Lys Tyr Lys Lys Gly Gly<br>385                       390                       395                   400 | 1200 |
| ctt gtg atc aat gaa act ggg ctg tac ttt gta tat tcc aaa gta tac<br>Leu Val Ile Asn Glu Thr Gly Leu Tyr Phe Val Tyr Ser Lys Val Tyr<br>                                   405                       410                   415 | 1248 |
| ttc cgg ggt caa tct tgc aac aac ctg ccc ctg agc cac aag gtc tac<br>Phe Arg Gly Gln Ser Cys Asn Asn Leu Pro Leu Ser His Lys Val Tyr<br>                      420                       425                       430 | 1296 |
| atg agg aac tct aag tat ccc cag gat ctg gtg atg atg gag ggg aag<br>Met Arg Asn Ser Lys Tyr Pro Gln Asp Leu Val Met Met Glu Gly Lys<br>               435                       440                       445 | 1344 |
| atg atg agc tac tgc act act ggg cag atg tgg gcc cgc agc agc tac<br>Met Met Ser Tyr Cys Thr Thr Gly Gln Met Trp Ala Arg Ser Ser Tyr<br>450                       455                       460 | 1392 |
| ctg ggg gca gtg ttc aat ctt acc agt gct gat cat tta tat gtc aac<br>Leu Gly Ala Val Phe Asn Leu Thr Ser Ala Asp His Leu Tyr Val Asn<br>465                       470                       475                   480 | 1440 |
| gta tct gag ctc tct ctg gtc aat ttt gag gaa tct cag acg ttt ttc<br>Val Ser Glu Leu Ser Leu Val Asn Phe Glu Glu Ser Gln Thr Phe Phe<br>                                   485                       490                   495 | 1488 |
| ggc tta tat aag ctc taa<br>Gly Leu Tyr Lys Leu<br>               500 | 1506 |

```
<210> SEQ ID NO 18
<211> LENGTH: 501
<212> TYPE: PRT
<213> ORGANISM: Artificial Sequence
<220> FEATURE:
<223> OTHER INFORMATION: Synthetic Construct

<400> SEQUENCE: 18
```

Met Gly His Thr Arg Arg Gln Gly Thr Ser Pro Ser Lys Cys Pro Tyr
1               5                     10                     15

Leu Asn Phe Phe Gln Leu Leu Val Leu Ala Gly Leu Ser His Phe Cys
                   20                     25                     30

Ser Gly Val Ile His Val Thr Lys Glu Val Lys Glu Val Ala Thr Leu
               35                     40                     45

Ser Cys Gly His Asn Val Ser Val Glu Glu Leu Ala Gln Thr Arg Ile
        50                     55                     60

Tyr Trp Gln Lys Glu Lys Lys Met Val Leu Thr Met Met Ser Gly Asp
65                  70                     75                     80

Met Asn Ile Trp Pro Glu Tyr Lys Asn Arg Thr Ile Phe Asp Ile Thr

```
                       85                 90                  95
Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
                115                 120                 125

Glu His Leu Ala Glu Val Thr Leu Ser Val Lys Ala Asp Phe Pro Thr
                130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
                195                 200                 205

Thr Thr Asn His Ser Phe Met Cys Leu Ile Lys Tyr Gly His Leu Arg
                210                 215                 220

Val Asn Gln Thr Phe Asn Trp Asn Thr Thr Lys Gln Glu His Phe Pro
225                 230                 235                 240

Ser Ser Ile Pro Asp Ser Gln Thr Lys Val Phe Pro Gln Asp Lys Val
                245                 250                 255

Ile Leu Val Gly Ser Asp Ile Thr Phe Cys Cys Val Ser Gln Glu Lys
                260                 265                 270

Val Leu Ser Ala Leu Ile Gly His Thr Asn Cys Pro Leu Ile His Leu
                275                 280                 285

Asp Gly Glu Asn Val Ala Ile Lys Ile Arg Asn Ile Ser Val Ser Ala
                290                 295                 300

Ser Ser Gly Thr Asn Val Val Phe Thr Thr Glu Asp Asn Ile Phe Gly
305                 310                 315                 320

Thr Val Ile Ser Arg Ala Leu Gln Lys Glu Leu Ala Glu Leu Arg Glu
                325                 330                 335

Ser Thr Ser Gln Met His Thr Ala Ser Ser Leu Glu Lys Gln Ile Gly
                340                 345                 350

His Pro Ser Pro Pro Glu Lys Lys Glu Leu Arg Lys Val Ala His
                355                 360                 365

Leu Thr Gly Lys Ser Asn Ser Arg Ser Met Pro Leu Glu Trp Glu Asp
                370                 375                 380

Thr Tyr Gly Ile Val Leu Leu Ser Gly Val Lys Tyr Lys Lys Gly Gly
385                 390                 395                 400

Leu Val Ile Asn Glu Thr Gly Leu Tyr Phe Val Tyr Ser Lys Val Tyr
                405                 410                 415

Phe Arg Gly Gln Ser Cys Asn Asn Leu Pro Leu Ser His Lys Val Tyr
                420                 425                 430

Met Arg Asn Ser Lys Tyr Pro Gln Asp Leu Val Met Met Glu Gly Lys
                435                 440                 445

Met Met Ser Tyr Cys Thr Thr Gly Gln Met Trp Ala Arg Ser Ser Tyr
                450                 455                 460

Leu Gly Ala Val Phe Asn Leu Thr Ser Ala Asp His Leu Tyr Val Asn
465                 470                 475                 480

Val Ser Glu Leu Ser Leu Val Asn Phe Glu Glu Ser Gln Thr Phe Phe
                485                 490                 495

Gly Leu Tyr Lys Leu
                500
```

<210> SEQ ID NO 19
<211> LENGTH: 28
<212> TYPE: DNA
<213> ORGANISM: Artificial Sequence
<220> FEATURE:
<223> OTHER INFORMATION: Primer for the delta 5 chain of TCR

<400> SEQUENCE: 19
aatctagaca gcaagttaag caaaattc                                    28

<210> SEQ ID NO 20
<211> LENGTH: 27
<212> TYPE: DNA
<213> ORGANISM: Artificial Sequence
<220> FEATURE:
<223> OTHER INFORMATION: Primer for the delta 5 chain of TCR

<400> SEQUENCE: 20
aaactagttg tgagggacat catgttc                                     27

<210> SEQ ID NO 21
<211> LENGTH: 26
<212> TYPE: DNA
<213> ORGANISM: Artificial Sequence
<220> FEATURE:
<223> OTHER INFORMATION: Primer for the gamma 4 chain of TCR

<400> SEQUENCE: 21
aatctagaaa cttggaaggg agaacg                                      26

<210> SEQ ID NO 22
<211> LENGTH: 26
<212> TYPE: DNA
<213> ORGANISM: Artificial Sequence
<220> FEATURE:
<223> OTHER INFORMATION: Primer for the gamma 4 chain of TCR

<400> SEQUENCE: 22
aaactagtca ggaggaggta catgta                                      26

<210> SEQ ID NO 23
<211> LENGTH: 38
<212> TYPE: DNA
<213> ORGANISM: Artificial Sequence
<220> FEATURE:
<223> OTHER INFORMATION: Primer

<400> SEQUENCE: 23
agatctaagg agatatagat atgtctcgct ccgtggcc                         38

<210> SEQ ID NO 24
<211> LENGTH: 38
<212> TYPE: DNA
<213> ORGANISM: Artificial Sequence
<220> FEATURE:
<223> OTHER INFORMATION: Linker

<400> SEQUENCE: 24
actagtacta ccggcacctc ccaggggagg ggcttggg                         38

<210> SEQ ID NO 25
<211> LENGTH: 15
<212> TYPE: DNA
<213> ORGANISM: Artificial Sequence
<220> FEATURE:

-continued

<223> OTHER INFORMATION: Linker

<400> SEQUENCE: 25
ggaggtgccg gtagt                                                          15

CHIMERIC MOLECULE INVOLVING OLIGOMERIZED FASL EXTRACELLULAR DOMAIN

FIELD OF THE INVENTION

The invention relates to new chimeric molecules involving in their structure, a combination of the extracellular domain (EC) of the FasL protein and a domain enabling oligomerisation of this Fas Ligand (FasL) EC domain, such as the Ig-like (so-called Ig in the following pages) domain of the gp190 receptor for the Leukemia Inhibitory Factor (LIF), or involving in their structure variants of said domains.

The invention also relates to compositions comprising the chimeric molecule defined herein and relates to the use of these chimeric molecules especially to trigger cytotoxic activity toward cells sensitive to FasL. The invention also provides compositions or agents for use for therapeutic purposes that comprise the chimeric molecules.

The chimeric molecules of the invention can especially be used for various therapeutic purposes requiring cytotoxic activity in determined cells and in particular can be useful in the treatment of diseases characterised by the presence of transformed cells or infected cells or activated cells, such as cancers, infections, autoimmune diseases, transplantation rejection.

BACKGROUND OF THE INVENTION

FasL (CD95L) is a type II homotrimeric transmembrane protein of the TNF (Tumor Necrosis Factor) family of cytokines (1). FasL is the ligand of the extracellular receptor designated Fas. FasL is especially expressed on activated T lymphocytes and natural killer cells, as a weapon to eliminate transformed and infected cells expressing the transmembrane receptor Fas (CD95/APO-1) (2). Binding of ligand FasL to its cellular receptor Fas triggers apoptosis via the caspase cascade. FasL itself is homotrimeric, and a productive apoptotic signal requires that FasL be oligomerized beyond the trimeric state.

In view of the interactions observed between the FasL protein and its receptor Fas, targeting human Fas initially appeared as a promising approach to treat cancer. But assays performed with an agonistic anti-Fas antibody triggered fulminant lethal hepatitis upon injection in mice, precluding the use of Fas inducers for a therapeutical purpose in human (3).

Observation that cleavage of membrane-bound FasL by a metalloprotease (4, 5) generates soluble homotrimeric FasL (sFasL), which is weakly apoptotic, and competes with membrane FasL for cell killing (6, 7) were made. Interestingly, upon cross-linking with antibodies, sFasL recovers its pro-apoptotic activity, and a FasL hexamer appears as the smallest functional form (8). Similarly, agonistic anti-Fas monoclonal antibodies (mAb) are mostly of the IgM or the self-aggregating IgG3 isotypes. In an attempt to avoid the need for cross-linking reagent, the inventors prepared chimeric molecules as polymers of FasL extra cellular domain (FasL chimeras) which proved to be non toxic and harboured cytotoxic, especially apoptotic, properties.

SUMMARY OF THE INVENTION

The inventors accordingly generated a series of FasL chimeras by fusing FasL extracellular domain with a domain/module of the LIF receptor gp190 to obtain oligomers of the FasL EC domain and analysed the capacity of the generated chimera to trigger cell death.

The extracellular domain of FasL may be designated sFasL.

The invention thus relates to a chimeric molecule comprising a monomeric structure (designated IgFasL) which contains, from its N-terminal end to its C-terminal end, the following fused domains:
  a) an Ig-like domain (designated Ig) of the human Leukemia Inhibitory Factor (LIF) receptor gp190, or a functional variant thereof having the capacity to self-associate in the context of the chimeric molecule,
  b) a linker which acts as a spacer between domains a) and c) of the chimeric molecule;
  c) the extracellular domain of the human FasL protein or a functional variant thereof;

wherein the chimeric molecule is a polymer (pFasL), of at least 6 repeats of said monomeric structure, said polymer being able to bind and to activate a transmembrane receptor named Fas (Fas receptor) on Fas expressing cells and, in particular, as a result triggering a cytotoxic activity toward Fas expressing cells.

The polymeric chimeric molecule is in particular a homopolymer of IgFasL monomers or alternatively, in a particular embodiment where further domains such as soluble FasL (sFasL) are used in addition to the IgFasL, the polymer is an heteropolymer comprising IgFasL monomers and sFasL monomers.

DETAILED DESCRIPTION OF THE INVENTION

The invention thus concerns, in a particular embodiment, a polymeric chimeric molecule where a first category of monomers consists of or comprises IgFasL and a second category of monomers consists of or comprises sFasL. Unless otherwise stated in the present application, or technically not relevant, both types of polymers, i.e., homopolymers and heteropolymers, are encompassed by the designation pFasL.

The polymeric structure of the chimeric molecule of the invention is obtained as a result of the ability of the FasL extracellular domain to multimerize to form trimeric structures combined with the ability of the Ig-like module of the gp190 receptor (10) to self-associate, thereby enabling aggregation of the trimeric structures in said chimeric molecules. When variants of one or both domains among Ig-like and EC are used in the construction of the chimeric molecule, the variants are selected for their ability to keep substantially the properties of the original domain in polymerisation.

Chimeric molecules of the invention can have distinct polymerisation degrees.

Polymeric chimeric molecules of the invention obtained from polymerization of the three fused domains defined as a), b) and c) above and optionally additional FasL domains, in particular sFasL are also named pFasL for polymeric FasL.

In a particular embodiment, the invention relates to the monomeric structure of the chimeric molecule, composed of domains a) b) and c).

In a particular embodiment, the chimeric molecule of the invention comprises ahead from the Ig-like domain, a signal peptide necessary for expression of the chimeric molecule in cells or residual amino acid residues from such a signal peptide or from construction sequences such as restriction sites.

As stated above, the chimeric molecule of the invention can be built having recourse to the Ig-like domain of the human gp190 receptor or using a variant thereof. Such a variant includes polypeptidic variants derived by mutation (especially by point mutation of one or more amino acid residues to the extent that the original sequence is conserved at 90% or more, especially more than 95%) of the original Ig-like domain of the gp190.

In a particular embodiment a functional variant is the Ig-like domain of a different receptor having a similar amino acid sequence, such as the Ig-like domain of the OSMR (Oncostatin M Specific receptor Subunit beta—Mosley B. et al JBC 1996; 32635-32643) or the gp130 receptors (Hibi M. et al—1990, Cell 63, 1149-1157). Advantageously the tridimensional structure of globular type of the Ig-like domain is preserved.

In a particular embodiment, the Ig-like domain which is used for the preparation of the chimeric molecule of the invention has the amino acid sequence SEQ ID No 4 of the Ig-like domain (designated Ig) of the human Leukemia Inhibitory Factor (LIF) receptor gp190.

The linker which is present between domains a) and b) in the chimeric molecule can be described functionally as a spacer, useful or necessary to preserve the accessibility of the FasL moieties for the binding domain of the Fas receptor, in the chimeric molecule.

In a particular embodiment of the invention, the linker is a polypeptide or a peptide having an amino acid sequence that contains from 2 to 10 amino acid residues, especially 2, 3, 4, 5, 6, 7, 8, 9, or 10 amino acid residues.

In a particular embodiment the linker has the amino acid sequence of SEQ ID No 6.

In another embodiment, the linker has the structure of a dipeptide such as LG or a peptide comprising one or many lysine (K) residues.

The extracellular domain of the FasL protein, especially the extracellular domain of the human FasL protein is a polypeptide having a sequence (SEQ ID No 8 constituted by amino acid residues 108 to 281 of the polypeptidic chain of the full-length human FasL protein and available under accession number U11821.1 in EMBL.

A variant of the extracellular domain of FasL may be a polypeptidic variant derived by mutation (especially by point mutation of one or more amino acid residues to the extent that the original sequence is conserved at 90% or more, especially more than 95% or 99%) of the original extracellular domain.

The naturally cleaved FasL (cFasL) obtained by cleavage of the membrane-bound FasL by a metalloprotease can be one variant of interest for combination with the other domains in the chimeric molecule.

In particular, the extracellular domain of the FasL protein may be a variant having a modified amino acid sequence with respect to the sequence of SEQ ID No 8.

The amino acid sequences are disclosed by reference to the one-letter symbol for the designation of the amino acid residues.

The modification(s) defining the variant of the extracellular domain of FasL and/or the modifications defining the variant of the Ig-like domain of the gp190 protein can independently be deletion(s), including especially point deletion(s) of one or many amino acid residue(s) or can be substitution(s), especially conservative substitution(s) of one or many amino acid residue(s). Such conservative substitutions encompass a change of residues made in consideration of specific properties of amino acid residues as disclosed in the following groups of amino acid residues and the resulting substituted polypeptide should not be modified functionally:

Acidic: Asp, Glu;
Basic: Asn, Gln, His, Lys, Arg;
Aromatic: Trp, Tyr, Phe;
Uncharged Polar Side chains: Asn, Gly, Gln, Cys, Ser, Thr, Tyr;
Nonpolar Side chains: Ala, Val, Leu, Ileu, Pro, Phe, Met, Trp;
Hydrophobic: Ile, Val, Leu, Phe, Cys, Met, Nor;
Neutral Hydrophilic: Cys, Ser, Thr;
Residues impacting chain orientation: Gly, Pro
Small amino acid residues: Gly, Ala, Ser.

In another embodiment, depending on the property(ies) guiding the choice for substitution of amino acid residue(s), modification of residue(s) can alternatively be determined to modify the properties of the resulting polypeptide, and said substitution(s) are selected to be non conservative.

In a particular embodiment of the invention, the chimeric molecules are in a composition comprising a mixture of polymers having distinct degree of polymerisation. The composition may advantageously comprise more than 50% polymers having structures with a polymerisation degree higher than hexameric. In a particular embodiment it may be a composition of dodecameric and hexameric structures.

The chimeric molecule of the invention has the ability to bind and/or to activate a transmembrane receptor named Fas (Fas receptor) on Fas expressing cells. In doing so, said polymer triggers a cytotoxic activity toward Fas expressing cells, after binding to the Fas receptor. The ability to bind the Fas receptor can be determined especially by measuring the dissociation constant of the ligand/receptor complex. For the determination of the suitability of variants domains to be used in the preparation of the chimeric molecule of the invention, the Kd constant of the prepared molecule may be measured and compared to the values indicated in the examples. Alternatively, the affinity of a chimeric molecule for the Fas receptor may be tested by Surface Plasmon resonance especially in accordance with the Biacore® method.

In a particular embodiment the affinity of IgFasL for the membrane Fas receptor is essentially identical to the affinity of FasL for said receptor.

The cytotoxic activity generated when using the chimeric molecule of the invention can be determined using a colorimetric assay such as an MTT assay. The MTT assay consists in determining whether the tested cells are capable of reducing yellow substrate MTT (3-(4,5-Dimethylthiazol-2-yl)-2,5-diphenyltetrazolium bromide) to give rise to purple formazan which is solubilised by the addition of a solubilisation solution (such as a solution of detergent SDS in diluted hydrochloric acid). The reduction of MTT can be detected by absorbance measurement. Only living cells are able to cleave the MTT to reduce it, as said reduction occurs through the action of mitochondrial enzymes when the mitochondria are active. Thus, cytotoxicity is revealed as a consequence of the failure of the tested cells to produce purple formazan. Assays of this type are described in the Examples of the present invention, with respect to a MTT viability assay as disclosed in (14).

The cytotoxic activity may be the result of activation of an apoptotic pathway, especially involving the caspase signaling cascade triggered by the Fas receptor.

According to a particular embodiment, the chimeric molecule comprises a homohexameric structure of the extracellular domain of the FasL protein or of its variant or comprises a homododecameric structure of the extracellular domain of the FasL protein or of its variant. In a specific embodiment, it consists of such structures.

The inventors have observed that the increase in the number of monomeric units of the FasL protein (or its variant) improves the outcome of the interaction with the Fas receptor and the effects on the targeted cells, especially the elicited cytotoxic properties.

In a particular embodiment, the chimeric molecule of the invention is a chimeric polypeptide wherein the amino acid sequence of the Ig-like domain (designated Ig) of the human Leukemia Inhibitory Factor (LIF) receptor gp190 is SEQ ID No 4 and the amino acid sequence of the extracellular domain of the human FasL protein is SEQ ID No 8.

In a particular embodiment of the invention, the linker of the chimeric molecule has the amino acid sequence of SEQ ID No 6.

In another embodiment of the invention, the chimeric molecule is a polypeptide having the sequence of SEQ ID No 12 resulting from the fusion of the polypeptidic domains having amino acid sequences SEQ ID No 4 (Ig-like), SEQ ID No 6 (linker) and SEQ ID No 8 (FasL EC), present according to that order. It is encoded by the polynucleotide having the nucleic acid sequence of SEQ ID No 11. A polypeptide including the signal peptide expressed by the polynucleotide used for cell expression and secretion is represented with the sequence of SEQ ID No 2.

According to an embodiment of the invention, the chimeric molecule which binds the Fas receptor expressed on human cells triggers a conformational change of said Fas receptor. This conformational change may influence the signalling cascade and resulting cytotoxic activity. Conformational change may be assayed in accordance with the disclosed test described in the examples.

The invention relates also to a chimeric molecule which further comprises an additional polypeptidic domain suitable for targeting specific cells, especially for targeting tumor antigens on specific cells, or for targeting receptors on specific cells. The polypeptidic domain may be a ligand or a fraction of a ligand molecule for a receptor such as a receptor selectively expressed on determined cells, especially immune cells or tumor cells, an antibody or a functional fragment of an antibody directed against an antigen specifically expressed on determined cells, especially immune cells or tumor cells, a ligand or a fraction thereof of an infectious protein expressed on or in an infected cell or an antibody or a functional fragment thereof directed against such a protein, a ligand for an antigen receptor (T-cell receptor or B-cell receptor) involved in autoimmunity or in the immune response to a pathogenic agent, especially an infectious agent, or with an alloantigen.

In a particular embodiment, the invention relates to a chimeric pFasL molecule which comprises, as a fusion polypeptide with the monomeric structure IgFasL, an additional polypeptidic domain (so-called "X domain" or heterologous polypeptidic domain) thus forming a X-pFasL polymeric molecule. This "X" polypeptidic domain is in particular suitable for targeting specific cells (and is accordingly designated as a cell-targeting polypeptidic domain or molecule).

In a particular embodiment of the invention, the additional polypeptidic domain "X", in particular the cell-targeting polypeptidic domain is fused upstream from the 5' end of the IgFasL entity.

The obtained chimeric pFasL or its complex version X-pFasL molecule is a chimeric polymer having a degree of polymerization of six or more or a mixture of chimeric polymers at least 50% of which have a degree of polymerization of six or more than six, in particular a degree of polymerization of ten or twelve or more than ten or twelve, which exhibits an improved cytotoxic activity with respect to the polymeric pFas, i.e., the polymer devoid of the heterologous polypeptidic domain when assayed on the same cell type.

In an embodiment of the invention, in particular when the additional polypeptidic domain is complex (e.g. has a plurality of polypeptidic chains) or is a large molecule, the chimeric molecule of the invention is a recombinant protein resulting from the fusion of the IgFasL monomer with at least one domain or at least one chain of the additional polypeptidic "X" domain present in a cell-targeting polypeptidic domain or molecule.

In a particular embodiment, the complex X-pFasL thus obtained results from the cotransfection in a production cell of multiple vectors, in particular plasmids or viral vectors, especially lentiviral vectors, wherein one vector is recombined with a polynucleotide that encodes the IgFasL, optionally fused with the domain or chain of an additional polypeptidic domain, in particular with a cell-targeting polypeptidic domain or molecule and one further vector is recombined with a polynucleotide encoding sFasL.

The inventors have obtained results showing that coexpression of sFasL with the IgFasL molecule possibly fused with the heterologous polypeptidic domain, in particular the cell-targeting polypeptidic domain (or any other appropriate additional polypeptidic domain) may enhance the production rate of the chimeric pFasL or X-pFasL. Accordingly, the association of sFasL with the extracellular domain of FasL provides optimization of the production of the chimeric molecule, as sFasL incorporates into the polymer formed.

In a particular embodiment of the invention, the IgFasL monomer molecule or the pFasL or X-pFasL may further comprise a tag or a flag, especially introduced in the construct as a further polypeptidic moiety.

According to a particular embodiment, the chimeric molecule of the invention comprises a fraction of human ligand CD80, which is the ligand for human CD28 cell receptor, i.e., comprises the extracellular domain of human CD80 disclosed as SEQ ID No 16. The extracellular domain of CD80 (Freeman et al. J Exp Med 1991; 174: 625-31 or EMBL no ABK41933.1) is present at the N-terminal end of the Ig-like domain of the chimeric molecule. In the nucleic acid construct encoding this particular chimeric molecule, the nucleic acid sequence encoding the extracellular domain of human CD80 (disclosed as SEQ ID No 15) is inserted 5' from the nucleic acid sequence encoding the Ig-like domain. In particular it contains the nucleotide sequence of a signal peptide suitable for expression in production cells. This particular chimeric molecule designated CD80IgFasL is disclosed as SEQ ID No 18. A chimeric molecule comprising the extracellular domain of the CD80 ligand is capable of targeting cells that express the CD28 receptor.

In a particular embodiment of the chimeric molecule, the CD80 extracellular domain may be replaced by the corresponding domain of the human CD86 ligand for the CD28 receptor (CD86 is also designated T-lymphocyte activation antigen CD86) which appears to be functionally homologous with CD80.

In an embodiment of the invention, the chimeric molecule of the invention comprises a cell-targeting moiety which is a ligand or a binding fragment of a ligand recognizing a cellular receptor of a cell. The ligand or its binding fragment is in particular selected among ligands having a single polypeptidic chain or capable of being incorporated in the chimeric molecule as a unique chain. Such ligands may be the TCRγδ ligand or its extracellular portions Vγ4Vδ5, or a HLA molecule. The Examples below describe the preparation of such chimeric molecules. Among HLA molecules, HLA A are particular suitable molecules used in the context of the invention, illustrated with HLA A*02:01, which is disclosed as AJ575565.1 (*Homo sapiens* HLA-A gene for MHC class I antigen, HLA*0201 allele, exons 1-8).

In a particular embodiment, the invention relates to a chimeric heteropolymeric molecule comprising both extracellular domain of the human FasL protein or a variant thereof fused with the Ig-like domain as described herein, and comprises also soluble human FasL (sFasL), the thus obtained heteropolymer being characterized in that the proportion of sFasL monomers with respect to the IgFasL monomers or a variant thereof is less than 50%, advantageously is from 10% to 40%, in particular from 10% to 20%. The inventors have indeed shown (see in particular the examples) that combining the IgFasL monomers with a proportion of sFasL monomers in a range of less than 50% of sFasL or in particular in a range of 10% to 40% in particular in a range of 10% to 20% of FasL improves the level of production of the polymeric chimeric molecule and/or its activity.

Accordingly, the invention concerns a heteropolymeric pFasL molecule or a heteropolymeric X-pFasL molecule wherein the IgFasL monomers in at least part of the polymeric chain are substituted by sFasL. In particular, 10% to less than 50%, for example 10% to 40% or 10% to 20% of domains derived from FasL are sFasL monomers.

In a particular embodiment, polymeric chimeric molecules of the invention are glycosylated.

The invention also concerns a nucleic acid molecule which encodes a chimeric molecule as defined herein. Such a nucleic acid molecule may be obtained by synthesis, or by recombination of various nucleic acids in accordance with well known methods for the skilled person.

A nucleic acid molecule of the invention comprises or consists of the successive functional domains organized as follows from its 5' to its 3' end:

(i) optionally a nucleotide sequence encoding a signal peptide for production in cells and secretion;

(ii) optionally a nucleotide sequence encoding a heterologous polypeptidic domain ("X") in particular a polypeptidic domain suitable for targeting cells;

(iii) a nucleotide sequence encoding an Ig-like domain in the Leukemia Inhibitory Factor receptor gp190, or a functional variant thereof having the capacity to self-associate in the context of the chimeric molecule;

(iv) a nucleotide sequence encoding a linker acting a spacer between domains encoded by nucleic acid sequences (iii) and (v);

(v) a nucleotide sequence encoding the human FasL protein or a functional variant thereof.

A particular nucleic acid molecule of the invention encoding IgFasL has the nucleotidic sequence SEQ ID No 11 and reflects the coding sequence of IgFasL devoid of coding sequence for the signal peptide. Another particular nucleic acid sequence is a sequence resulting from fusion of SEQ ID No 3, SEQ ID No 5 and SEQ ID No 7 in this order, possibly supplemented by nucleotides required for fusion, especially nucleotides required to build restriction sites.

Another particular nucleic acid sequence is a sequence resulting from fusion of the nucleic acids having SEQ ID No 3, SEQ ID No 5 and SEQ ID No 7, in this order, possibly supplemented by the sequence encoding a signal peptide for secretion (SEQ ID No 10) and which has the sequence of SEQ ID No 1.

A further particular nucleic acid molecule of the invention comprises a nucleotide sequence disclosed above as sequence (ii) which, according to said embodiment, is a nucleotide sequence encoding the extracellular domain of the human CD80 ligand for the CD28 receptor or of the CD86 ligand for the CD28 receptor. Such a nucleic acid molecule may further encompass the signal peptide of the CD80 ligand or respectively the CD86 ligand.

Accordingly, the invention relates to a nucleic acid molecule having the nucleotide sequence disclosed as SEQ ID NO 17 and to its expression product designated CD80IgFasL having the amino acid sequence disclosed as SEQ ID NO 18. The inventors have prepared a chimeric molecule of the invention which is a polymer of CD80IgFasL monomers and has a number of monomers similar to that obtained when producing chimeric polymer IgFasL. They have shown in vitro on cells expressing the CD28 receptor that the CD80IgFasL chimeric molecule is correctly targeted to cells expressing this receptor and is active against them.

The invention is further directed to vectors, especially expression vectors, carrying the nucleic acid molecule of the invention. Vectors include in particular plasmids or viral vectors, in particular lentiviral vectors, which comprise sequences suitable for the control of expression of the nucleic acid of the invention, in cells.

The invention also relates to cells recombined, especially transfected, by the nucleic acid molecule or by the vector of the invention. Cells of interest are especially eukaryotic cells in particular insect cells, or cells of vertebrates, especially mammalian cells, including rodent or human cells, or are plant cells.

The invention also concerns compositions comprising a quantity of chimeric molecules of the invention wherein these molecules are polymers having the same structure and especially the same degree of polymerisation, or wherein polymers having different degrees of polymerisation are present in admixture, said polymers possibly having also different structures.

The invention also relates to a process for the preparation of a chimeric molecule of the invention which comprises the steps of:

a) transfecting or transducing host cells, in particular eukaryotic cells, and preferably mammalian cells or insect cells with a plasmid or a viral, in particular a lentiviral vector recombined with a nucleic acid molecule of the invention or a nucleic acid molecule having the sequence of SEQ ID NO: 17;

b) co-transfecting or transducing said host cells with a plasmid or a viral, in particular a lentiviral vector recombined with a nucleic acid molecule encoding sFasL, in particular a nucleic acid molecule having the sequence of SEQ ID NO: 7;

c) allowing the expression product of plasmids or vector under a) and b) to be formed;

d) recovering the chimeric heteropolymeric molecule.

The invention also relates to the use of the chimeric molecules of the invention in therapeutic compositions where said chimeric molecules are the active or one of a plurality of active ingredients. Therapeutic compositions further comprise excipients selected according to the administration route. They may also comprise agents improving delivery to the body, especially for immediate, controlled or sustained delivery.

In a particular embodiment the invention relates to an anti-tumor therapeutic composition which comprises, as an active ingredient against tumor development, a chimeric molecule as defined herein, or a nucleic acid or a vector of the invention, with pharmaceutical excipients suitable for administration by injection to a human patient diagnosed for a tumor.

According to another aspect of the invention, a chimeric molecule as defined herein, or a nucleic acid or a vector of the invention is used as an active ingredient in a therapeutic composition effective against infection by a pathogen, especially against viral infection, bacterial infection, parasite infection.

The invention thus also relates to the use of a chimeric molecule as defied herein, as a cytotoxic agent for the treatment of a human patient diagnosed for the presence of transformed cells or of uncontrolled proliferative cells or for the treatment of a human patient diagnosed for infection, wherein said proliferating or transformed cells or said infected cells express the cellular receptor designated Fas, Cytotoxicity can in particular be obtained as a result of apoptosis of cells.

The invention thus also concerns a method for the treatment of a patient diagnosed for the presence of transformed cells or of uncontrolled proliferative cells or for the treatment of a human patient diagnosed for infection, comprising administering chimeric molecules of the invention, or a composition comprising the same.

Hence the chimeric molecules of the invention can be used for treatment of pathologic condition in a human patient, where induction of apoptosis is required.

Among these pathologic conditions, cancers, infections, especially virus, bacterial or parasite infections, autoimmune diseases, response to allogenic transplantation of organ or tissue are targets for the treatment with chimeric molecules of the invention.

Among cancers, myeloma such as multiple myeloma (also designated Kahler disease) or lymphoma such as B or T cells lymphoma could be targeted for treatment when the chimeric molecule of the invention encompasses a fragment representing the extracellular domain of the human CD80 ligand of the CD28 receptor (or the corresponding domain of the CD86 ligand).

Cancers that may benefit from a treatment with chimeric molecules of the invention include lung, breast or oesophagus cancers, or lymphomas or melanomas or myeloma or leukemia.

Autoimmune diseases that may benefit from a treatment with chimeric molecules of the invention include Autoimmune Lymphoproliferative Syndrome (APLS).

By "treatment" it is meant that the steps performed result in improving the clinical condition of a human patient in need thereof, who suffers from tumor or cancer or has been diagnosed for an autoimmune disease or for rejection of organ or tissue transplant and/or has been diagnosed as being infected or being suspected to be infected by a pathogen, especially a virus a bacterium or a parasite. Such treatment aims at eliminating the transformed cells or the infected cells or at controlling the proliferative activity of cells. It may aim at eliminating excess of T lymphocytes in autoimmune diseases. Treatment encompasses improving the clinical status of the human patient, by eliminating or lowering the symptoms associated with the diagnosed pathological condition, and in a preferred embodiment restoring to health.

Further characteristics and properties of the invention are disclosed in the examples and drawings which follow.

BRIEF DESCRIPTION OF THE DRAWINGS

FIG. 1: Obtention and functional characteristics of the FasL/gp190 chimeras.

Panel A: Modules constituting gp190 and FasL are depicted as mature proteins. EC, TM and IC represent the extracellular, transmembrane and intracellular domains, respectively. N and C represent the N- and C-terminal regions. The numbers depict the domain boundaries used to create the chimeras. Cleaved FasL (cFasL) is spontaneously generated by a metalloprotease cleaving between aminoacids 126 and 127. Panel B: Representation of the cleaved FasL (cFasL) and the gp190/FasL chimeras. Panel C: Serial dilutions of supernatants from COS cells transfected with the FasL constructs or the empty vector (control) were incubated with Jurkat cells. Cell death was measured using the MTT assay. As a positive control, we used the commercially available antibody-cross-linked FasL (recFasL). Calculated C50 are indicated on the graph. Results from one representative experiment out of 5 are depicted.

Figure 2:
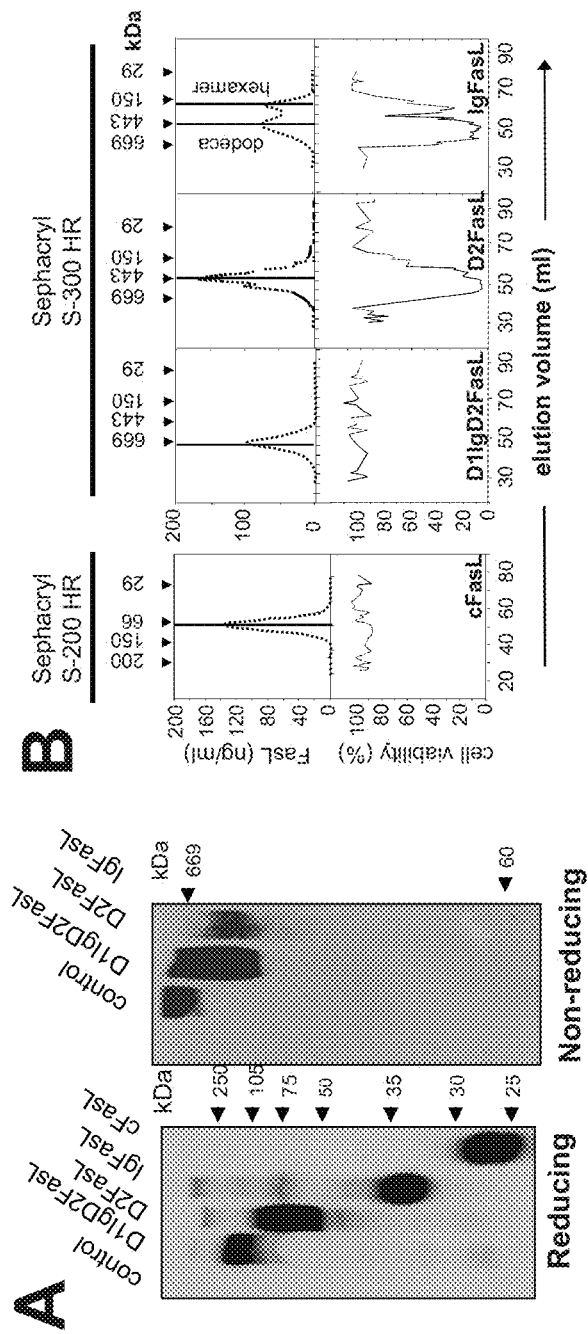
Figure 2:
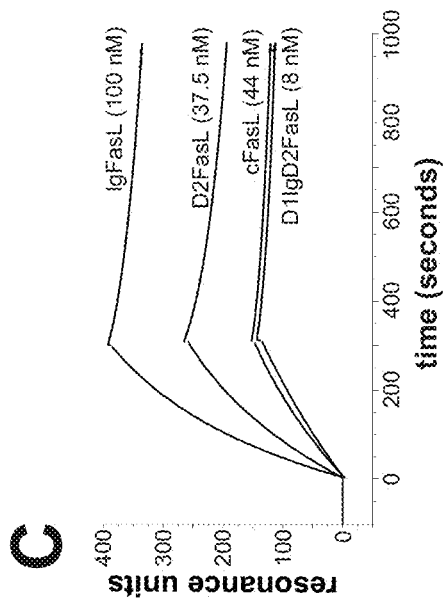

FIG. 2: Biochemical characterization of the FasL/gp190 chimeras.

Panel A: Supernatants from COS cells transfected with the FasL constructs were quantified by ELISA and 10 µg of FasL protein were loaded per lane. Migrations were performed under reducing (SDS-PAGE) or non-reducing (BN-PAGE) conditions. FasL was revealed by immunoblot. Panel B: 2 µg of FasL construct were loaded on the gel filtration column. FasL was quantified by ELISA in elution fractions, and cytotoxicity was measured using the MTT assay. Panel C: Affinity measurement using Biacore®. Fas-Fc was immobilized on the chip, before the indicated soluble FasL constructs were analyzed. A range of concentrations was tested for each analyte, but only the graph obtained with the highest concentration is displayed. Panel D: The apparent molecular weights and degree of oligo/polymerization of the FasL chimeras were estimated from the non denaturing gel electrophoresis and gel filtration experiments.

Figure 3:
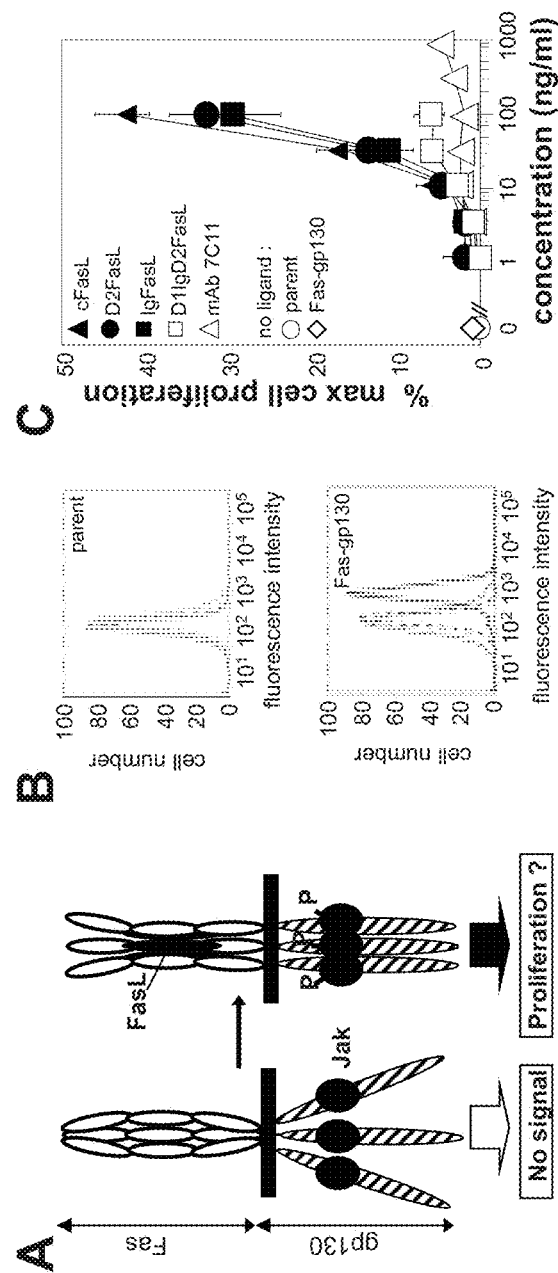

FIG. 3: FasL/gp190 chimeras and agonistic antibodies differentially act on Fas conformation.

Panel A: Description of the model used to analyze the requirement for a Fas conformational change during its activation. The Fas-gp130 hybrid receptor is stably expressed in the IL-3 dependent BA/F3 cell line. Panel B: Cell surface staining of parent BA/F3 cells (upper panel) and on a representative clone stably expressing the Fas-gp130 chimera (lower panel), with an isotype-matched control (dotted line), anti-murine Fas JO2 (dashed line) and anti-human Fas DX2 (continuous line). Panel C: Fas-gp130 BA/F3 cells were incubated with the indicated Fas triggers or controls, and proliferation was measured using a MTT assay. Results are expressed as percentages of the maximum proliferation obtained with a saturating IL-3 concentration. Proliferation of parent and transfected cells was also measured in the absence of any IL-3 or Fas trigger. Values are the mean±sd of 3 independent experiments.

Figure 4:
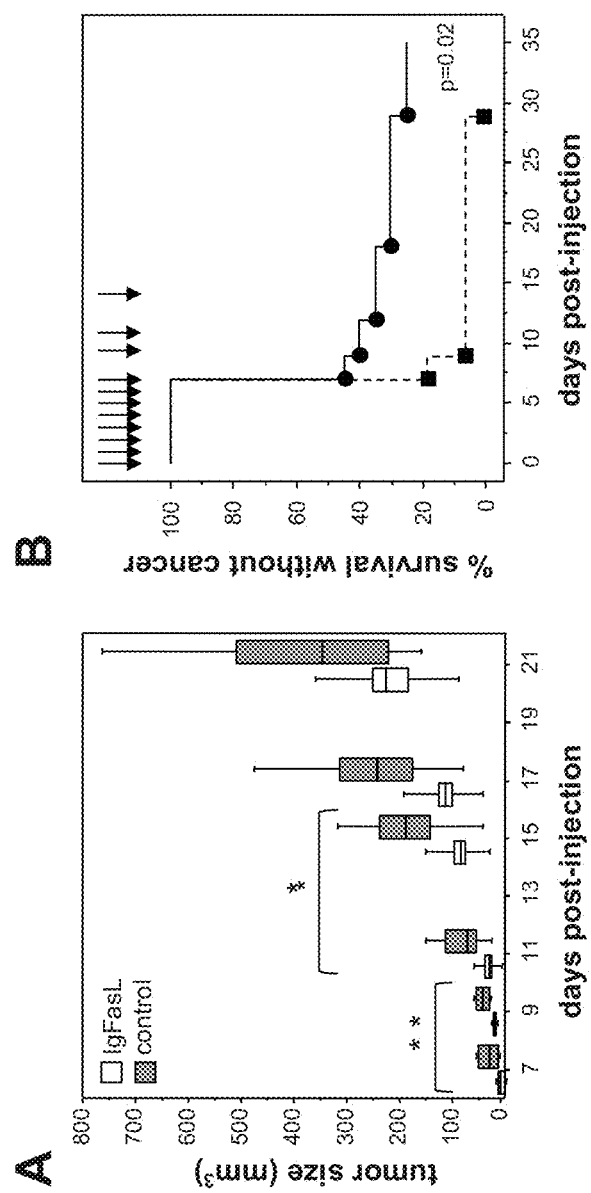

FIG. 4: Anti-tumor activity of IgFasL.

Panel A: Tumor growth in mice having received subcutaneously $10^5$ A431 cells at day 0, and 0.1 mL of concentrated IgFasL (white boxes) or IgFasL-free control (grey boxes) locally at days 2 and 7 (n=6 mice per group). Tumor volumes are expressed in $mm^3$. Values are presented as median, $25^{th}$ and $75^{th}$ percentiles (horizontal line, bottom and top of boxes), and $10^{th}$ and $90^{th}$ percentiles (bottom and top range bars) (**p=0.04, * p=0.05). Panel B: Kaplan-Meier analysis of cumulative survival without cancer of mice bearing A431 cells xenograft treated with IgFasL (black circles) or IgFasL-free control (black squares) (p=0.02). n=20 mice per group, from two experiments pooled.

FIG. 5: Nucleotide and amino acid sequences of IgFasL and its constitutive fragments SEQ ID No 9: cDNA sequence of the secretion signal peptide at the 5' end of the IgFasL chimeric gene: underlined: the SpeI enzyme restriction site used to build the chimeric gene; bold characters: the signal sequence of the gp190 protein SEQ ID No 3: cDNA sequence of "Ig", the Ig-like module of the IgFasL chimeric gene SEQ ID No 5: cDNA sequence of the linker stretch located between "Ig" and FasL in the IgFasL chimeric gene: underlined: the XbaI enzyme restriction site used to build the chimeric gene: bold characters: beginning of the EcoNI enzyme restriction site used to build the chimeric gene SEQ ID No 7: cDNA sequence of sFasL, the secreted portion of FasL in the IgFasL chimeric gene: bold characters: end of the EcoNI enzyme restriction site used to build the chimeric gene; underlined: stop codon SEQ ID No 1: complete cDNA sequence of the IgFasL chimeric gene:underligned: stop codon SEQ ID No 1 encompasses SEQ ID No 11, which starts with the codon at nucleotide 148 in SEQ ID No 1 and ends with the final codon of SEQ ID No 1.

SEQ ID No 10: Amino acid sequence of the secretion signal peptide at the 5' end of the IgFasL chimeric protein: underlined: the two amino acid residues added to the "Ig" sequence to generate the cDNA construct; bold characters: the signal sequence peptide (44 aa).

SEQ ID No 4: Amino acid sequence of "Ig", the Ig-like module of the IgFasL chimeric gene SEQ ID No 6: amino acid sequence of the linker stretch located between "Ig" and FasL in the IgFasL chimeric protein.

Seq ID No 8: amino acid sequence of sFasL, the secreted portion of FasL in the IgFasL chimeric protein.

SEQ ID No 2: complete amino acid sequence of the IgFasL chimeric protein (secretion signal sequence included).

SEQ ID No 2 encompasses SEQ ID No 12, which starts with amino acid residue Isoleucine (I) at position 50 in SEQ ID No 2 and ends with the final residue of SEQ ID No 2.

FIG. 6: CD80 and CD80IgFasL

DNA sequence of CD80 extracellular domain (Bold characters: start codon of human CD80 cDNA—Underlined: at the 5' end: sequence coding for the signal peptide; at the 3' end: XbaI restriction site used for cloning 5' to the IgFasL construct) and its corresponding amino acid sequence (Underlined: at the N-terminal end: signal peptide; at the C-terminal end: amino acid residues encoded by the XbaI restriction site used for cloning 5' to the IgFasL construct); DNA sequence of CD80IgFasL (Bold and underlined: the XbaI°/SpeI° joining sequence resulting from the fusion of CD80 extracellular region to IgFasL) and its corresponding amino acid sequence (Bold and underlined: amino acid residues encoded by the XbaI°/SpeI° restriction site used for cloning 5' to the IgFasL construct).

FIG. 7A: schematic description of the chimeric human FasL-derived constructs. Schematic representation of soluble FasL (sFasL), Flag-tagged sFasL (sfFasL), polymeric Flag-tagged soluble FasL (pfFasL), polymeric TCR γ4 and δ5 Flag-tagged soluble FasL generating the TCR-pfFasL upon cotransfection, and beta2-microglobulin-fused HLA-A*02:01 Flag-tagged soluble FasL (HLA-pfFasL). The f and p symbols represent the flag epitope and the LIF receptor-derived domain triggering the polymerisation of the FasL oligomers, respectively;

FIG. 7B: Effect of sFasL on pfFasL production by HEK cells upon lentiviral co-transduction.

HEK cells were transduced with a vector encoding sFasL and Green Fluorescent Protein. The resulting HEK-sFasL+ cell line and the wild-type HEK were transduced with a vector encoding pfFasL and Tomato. Cells were FACS-sorted for weak (HEK-pfFasL+) or strong (HEK-pfFasL++) Tomato expression. Secreted pfFasL was quantified with the Flag ELISA.

Figure 8:
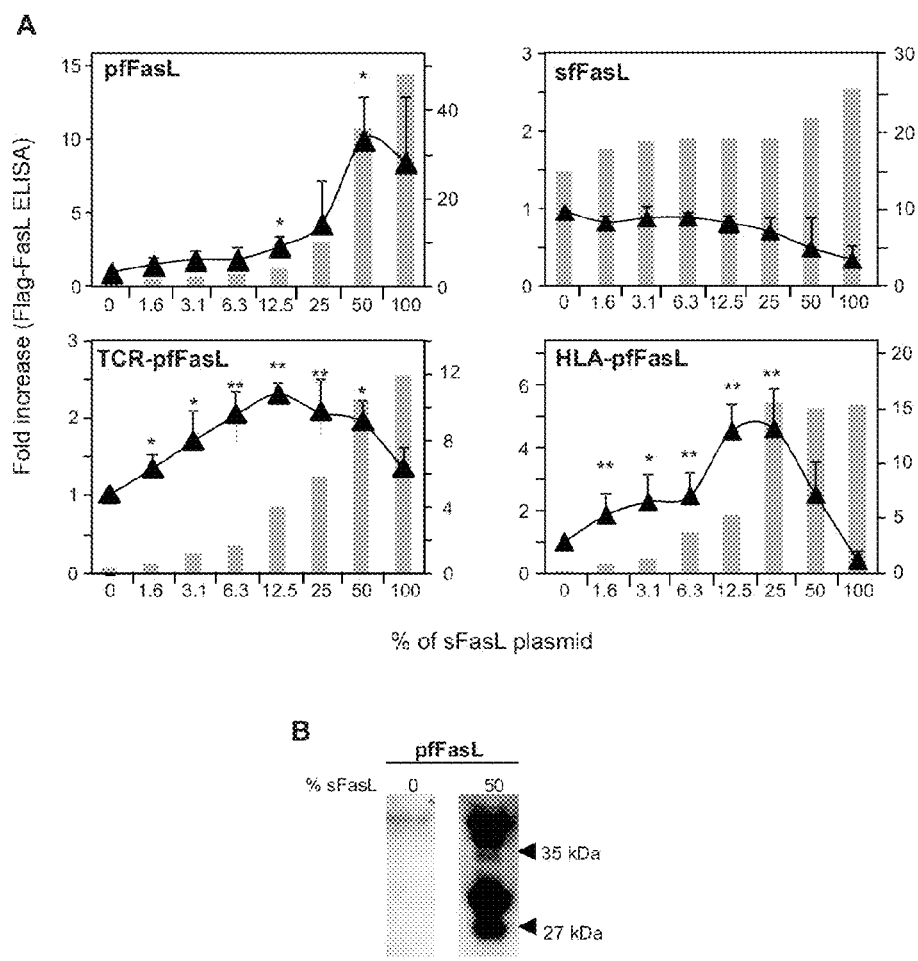

FIG. 8: Effect of sFasL on the supernatant production of the Flag-tagged FasL constructs. Panel A: an increasing amount expressed in percentage, of the sFasL encoding plasmid, was co-transfected with a fixed amount of the plasmids encoding pfFasL (upper left graph), sfFasL (upper right graph), TCR-pfFasL (lower left graph) and HLA-pfFasL (lower right graph). The excreted proteins were quantified in culture supernatants using an ELISA specific for FasL (shaded histograms, right-hand scale) and for Flag-tagged FasL (curves, left-hand scale). For the Flag ELISA, the measured concentrations were normalized according to the condition lacking sFasL. Are presented the mean+/−sd of four independent transfection experiments. * 0.02≤p≤0.05; ** p≤0.02. Panel B: direct anti-FasL immunoblot analysis of identical volumes of the cell culture supernatant containing pfFasL produced alone and with 50% of the sFasL plasmid, after SDS-PAGE separation under reducing conditions.

Figure 9:
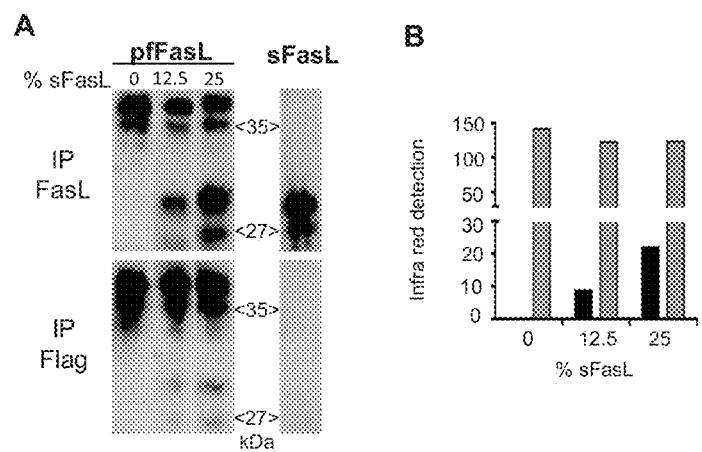

FIG. 9: Direct incorporation of sFasL in the polymeric aggregates containing the pfFasL protein. Panel A: Identical amounts of pfFasL (1 µg, according to the Flag ELISA) produced in the presence of the indicated ratios of added sFasL plasmid (left panels) was immunoprecipitated with the anti-FasL (upper panel) or anti-Flag (lower panel) antibodies, followed by a SDS-PAGE under reducing conditions and immunoblotting with an anti-FasL antibody. As a control, the same experiment was performed for the sFasL molecule (3 µg according to the FasL ELISA, right panel). Panel B: densitometric detection and quantification of the sFasL (grey bars) and pfFasL fractions (black bars).

Figure 10:
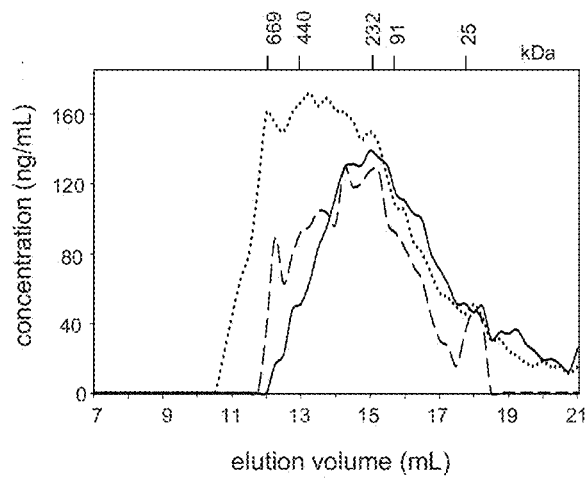

FIG. 10: gel filtration analysis of the pfFasL chimera produced in the presence or absence of sFasL. Gel-filtration separation on the Superose 6 column of the pfFasL chimera produced in the presence of 25% (dashed line), 50% (continuous line) or in the absence (dotted line) of added sFasL plasmid during the transfection. Elution fractions were measured by an ELISA specific for FasL.

Figure 11:
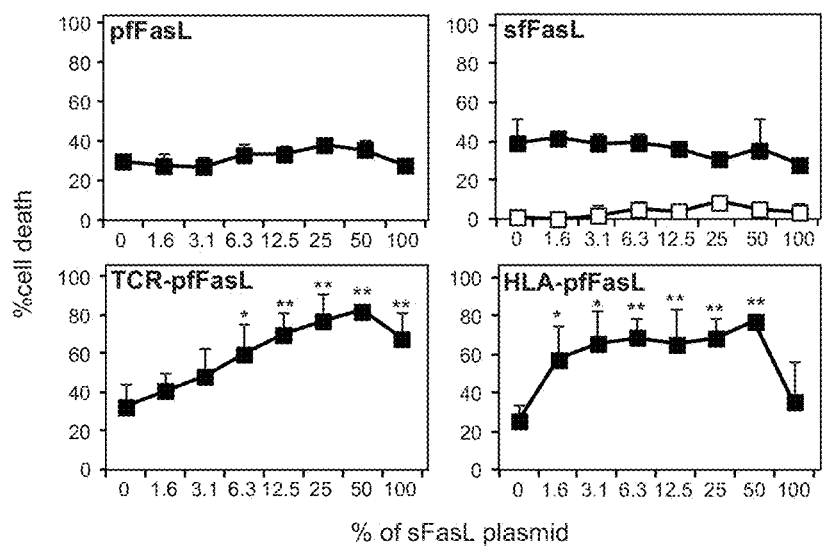

FIG. 11: Effect of sFasL on the cytotoxic activity of the Flag-tagged FasL constructs. The FasL-derived proteins pfFasL (upper left graph), sfFasL (upper right graph), TCR-pfFasL (lower left graph) and HLA-pfFasL (lower right graph) were expressed alone or upon co-transfection with the indicated percentage of the plasmid encoding sFasL. A fixed concentration triggering 25 to 40% of cell death, for the FasL-derived protein quantitated with the ELISA specific for Flag-tagged FasL, was incubated with the Fas-sensitive Jurkat cells. For the sfFasL construct, the filled squares and the empty squares depict the cytotoxicity of sfFasL in the presence and absence of the cross-linking anti-Flag antibody, respectively. Cytotoxicity was estimated by a measure of the remaining viable cells using the MTT assay. Are presented the mean+/−sd of four independent transfection experiments. * 0.01≤p≤0.05; ** p≤0.01.

Figure 12:
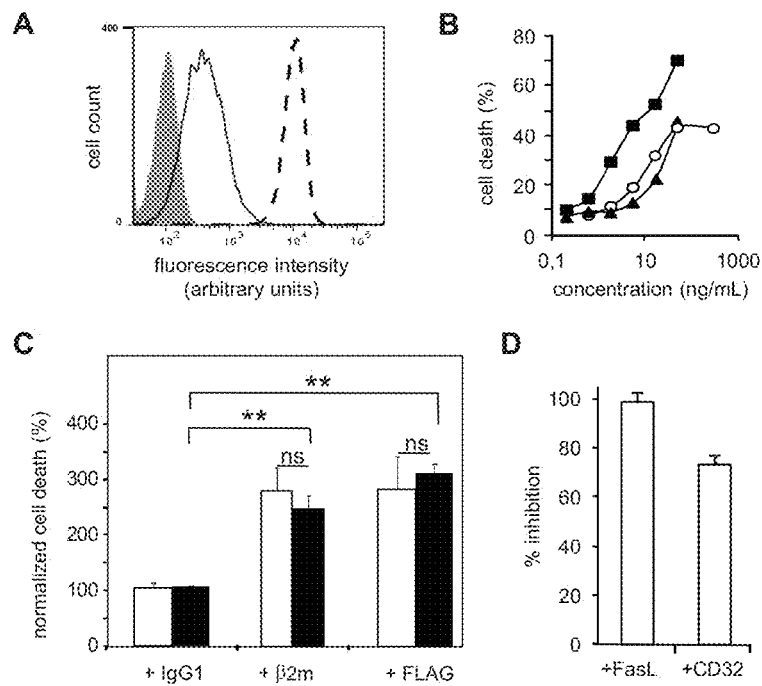

FIG. 12: Effect of sFasL on cell targeting of the FasL-containing chimeras. Panel A: murine Fas (continuous line), human CD32 (dashed line) and IgG1 isotype-matched control (shaded histogram) staining of the CD32+L-cell transfectant. Living cells were gated on the basis of the morphological parameters. Panel B: Fas sensitivity of the CD32+ L-cell transfectant to the indicated concentrations of the anti-Fas JO-2 antibody (circles), the HLA-pfFasL chimera expressed alone (triangle) or in the presence of 25% of the sFasL plasmid (squares), in the MTT viability assay. Panel C: The CD32+L-cells were incubated with the HLA-pfFasL chimera produced in the presence (black bars) or in the absence (white bars) of 25% of the sFasL plasmid, together with the indicated irrelevant IgG1 isotype-matched, anti-beta-2 microglobulin or anti-Flag antibodies. The concentrations of the chimera that triggered 20% of cell death and were at 15 and 0.3 ng/ml in the absence and presence of sFasL, as estimated using the ELISA specific for the Flag-tagged FasL. Cytotoxicity was measured with the propidium iodide assay and normalized to the effect of the chimera in the absence of antibody. Are presented the mean+/−sd of three independent experiments. Panel D: reversal in the presence of the blocking anti-FasL and anti-CD32 antibodies, of the cytotoxic effect of the immune complexes between the anti-Flag antibody and HLA-pfFasL co-expressed with sFasL. Are presented the mean+/−sd of three independent experiments. ns: non significant; ** p≤0.02.

Figure 13:
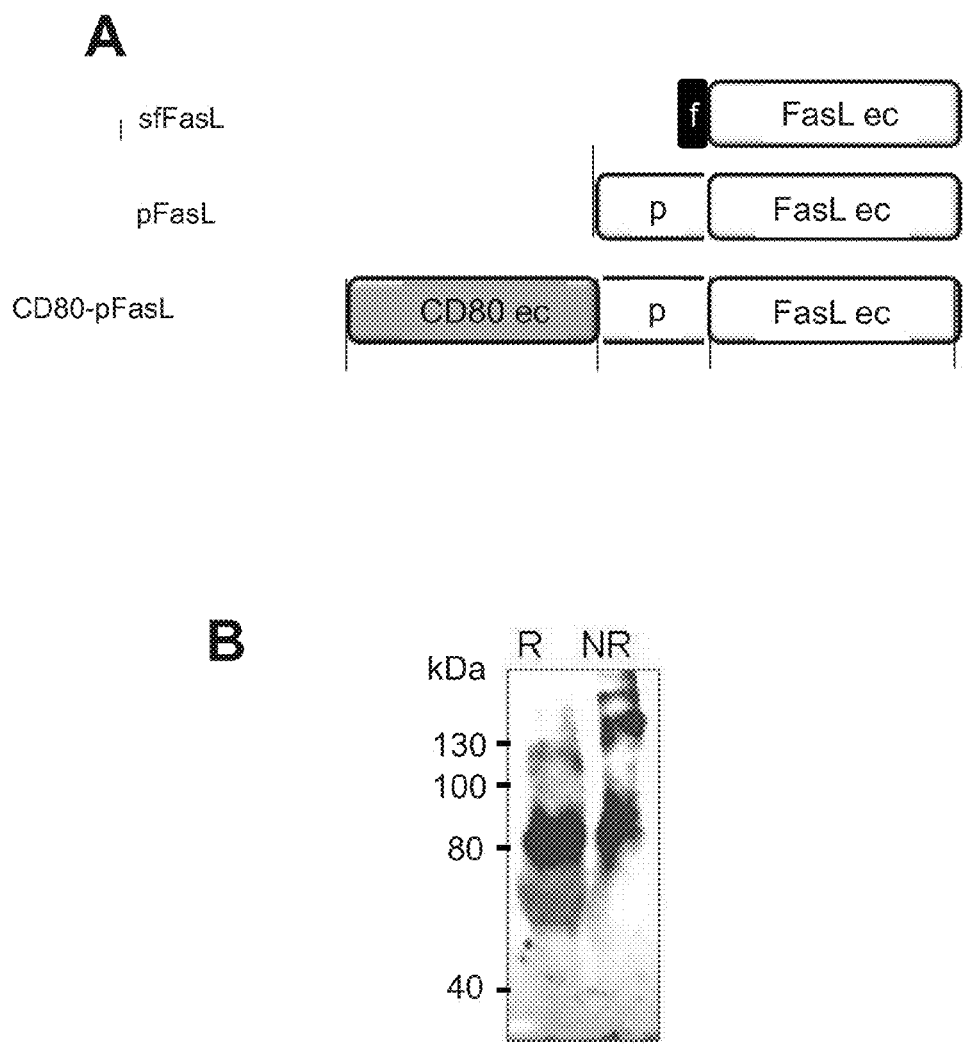

FIG. 13: Description of the recombinant FasL derived constructs. Panel A: The sfFasL module encompasses aa 108 to 281 from FasL as described in Example III, and the polymeric pFasL has been described in Example III. The CD80-pFasL contains the CD80 extracellular domain, i.e. aa 1 to 243 from full length human CD80. Panel B: anti-FasL immunoblot analysis of the CD80-pFasL chimeric protein, after SDS-PAGE separation under reducing (R) or non-reducing (NR) conditions.

Figure 14:
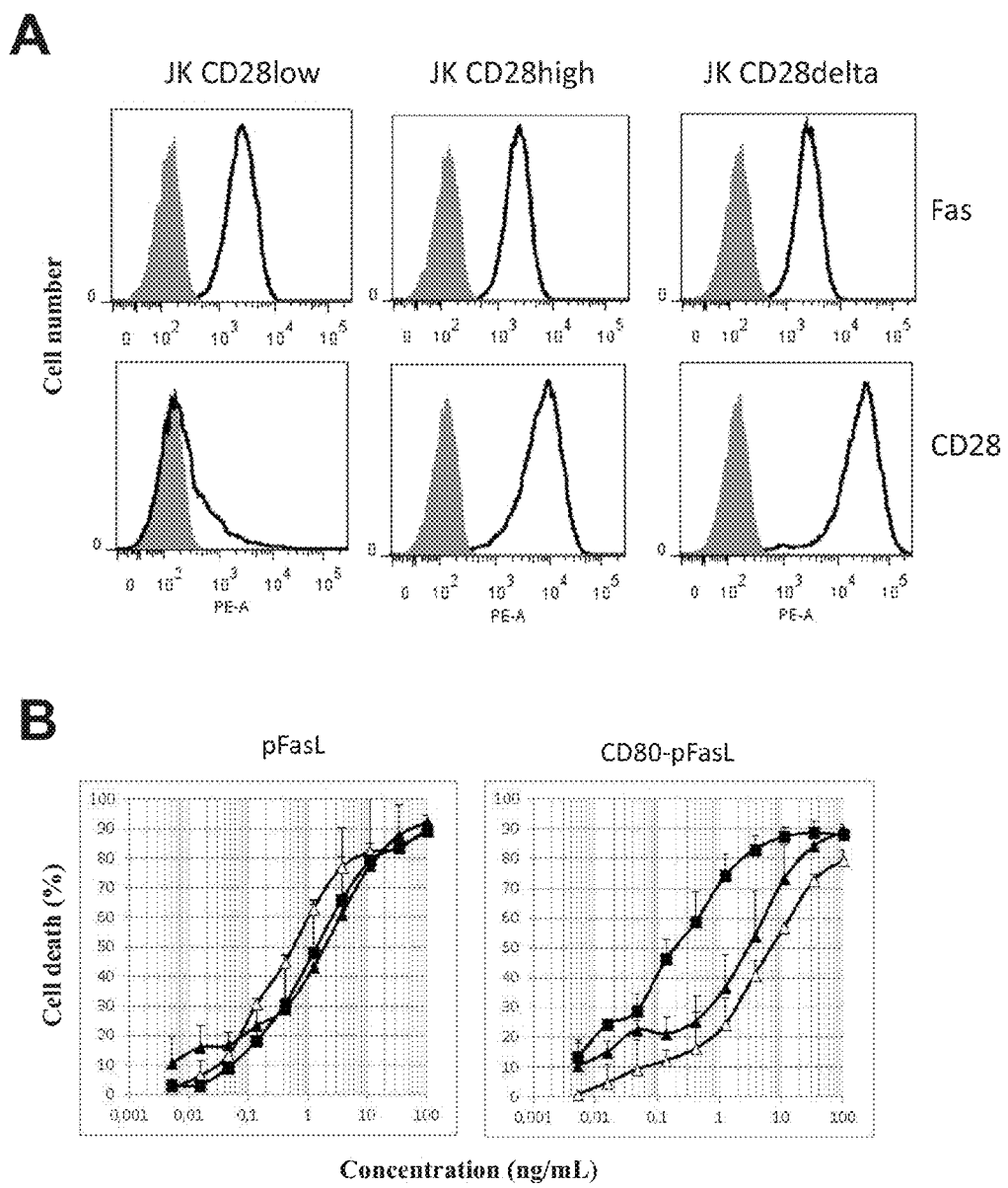
Figure 14:
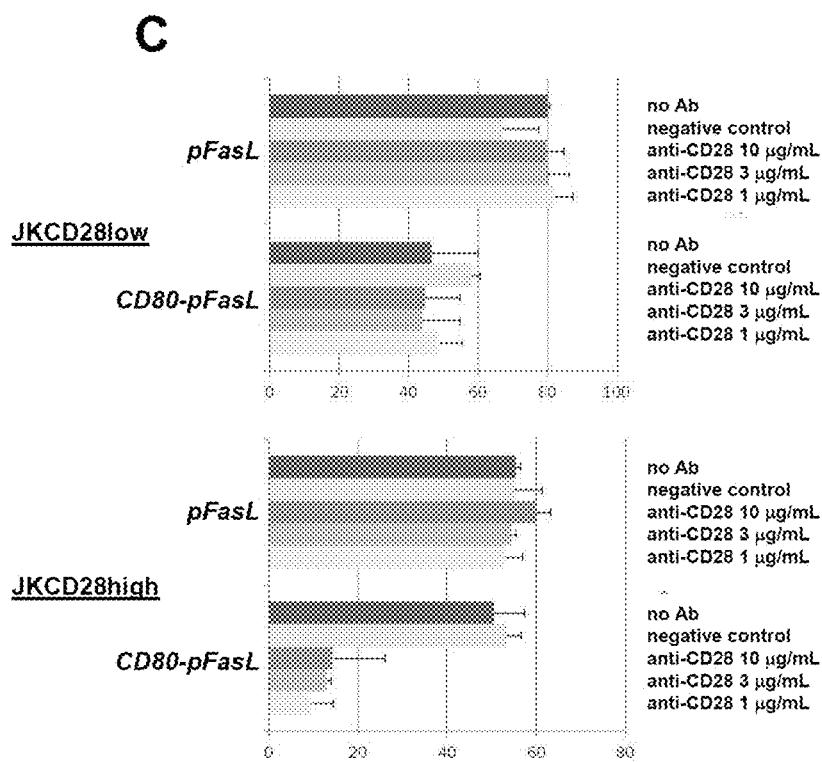

FIG. 14: Effect of the pFasL and CD80-pFasL chimeras on the JKCD28low, JKCD28high and JKCD28delta cell lines. Panel A: membrane expression of Fas and CD28 on the three cell lines. The cells were stained with the indicated antibodies, or with an isotype-matched negative control antibody (shaded histograms) then analysed by flow cytometry. Panel B: the apoptotic activity of the pFasL and CD80-pFasL chimeras was tested against the three cell lines (JKCD28 low: empty triangles; JKCD28high: filled triangles; JKCD28delta: squares) at a range of concentrations, measured in the FasL ELISA. Cell death was estimated by the MTT viability assay. Mean and sd from three distinct experiments. Panel C: the pFasL and CD80-pFasL chimeras were used at a non-saturating concentration that triggers a suboptimal cell death. The JKCD28low and JKCD28high cell lines were pre-incubated without (no antibody) or with an isotype-matched control antibody at 10 μg/mL or with the CD28.2 clone of anti-CD28 blocking antibody at 10, 3 or 1 μg/mL. Cell death was measured using the MTT cell viability assay. Mean and sd from three distinct experiments.

Figure 15:
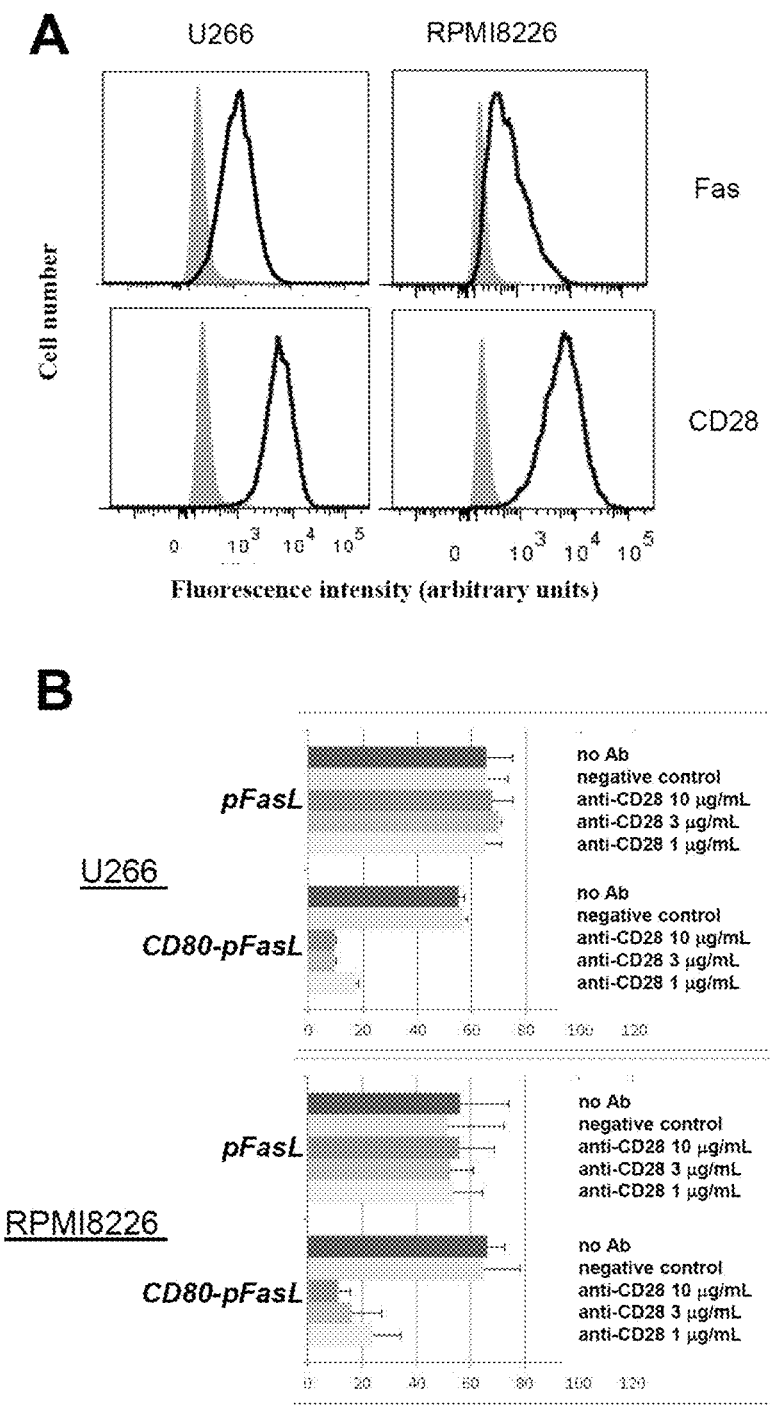

FIG. 15: Blocking CD28 on the myeloma cell lines U266 and RPMI8226 decreases the apoptotic activity of the CD80-pFasL chimera. Panel A: membrane expression of Fas and CD28 on the two cell lines. The cells were stained with the indicated antibodies (empty histograms), or with an isotype-matched negative control antibody (shaded histograms) then analysed by flow cytometry. Panel B: The pFasL and CD80-pFasL chimeras were used at a non-saturating concentration that triggers a suboptimal cell death. The U266 and RPMI8226 cell lines were pre-incubated without (no antibody) or with an isotype-matched control antibody at 10 μg/mL or with the CD28.2 clone of anti-CD28 blocking antibody at 10, 3 or 1 μg/mL. Cell death was measured using the MTT cell viability assay. Mean and sd from three distinct experiments.

FIG. 16: Improvement of production of the CD80-pFasL chimera by concomitant expression of the non apoptotic sfFasL. Panel A: supernatant production of CD80-pFasL as estimated by the CD80/FasL sandwich ELISA, following transfection of 30 μg of the CD80-pFasL plasmid alone or in the presence of the indicated percentage (w/w) of the sFasL-encoding plasmid. Panel B: presence of the sFasL protein into the complexes of the CD80-pFasL chimera, following co-transfection of the CD80-pFasL plasmid (30 μg) together with the indicated proportion (w/w) of the sFasL encoding plasmid. The cell culture supernatant was immunoprecipitated (IP) with the indicated antibody, followed by an immunoblot analysis with the anti-FasL antibody.

TABLE 1

Association/dissociation constants of the soluble FasL chimeras.

| Ligand | Kon (1/Ms) | Koff (Vs) | KD (M) | Chit |
|---|---|---|---|---|
| DlIgD2FasL | $1.3 \times 10^5$ | $3.3 \times 10^{-3}$ | $2.56 \times 10^{-8}$ | 8.34 |
| D2FasL | $1.6 \times 10^5$ | $6.0 \times 10^{-3}$ | $3.85 \times 10^{-8}$ | 3.37 |
| IgFasL | $2.5 \times 10^4$ | $4.1 \times 10^{-4}$ | $1.16 \times 10^{-8}$ | 2.75 |
| cFasL | $8.4 \times 10^4$ | $5.9 \times 10^{-3}$ | $6.94 \times 10^{-8}$ | 16 |

TABLE 2

IgFasL does not induce liver damage.
Mice were injected with the indicated ligands as described in Materials and Methods. Blood samples were harvested at the indicated time points and the levels of alanine amino transferase (ALAT) and aspartate amino transferase (ASAT) were measured in the serum.

| | GOT (IU/ml) | | GPT (IU/ml) | |
|---|---|---|---|---|
| Fas trigger | 6 hours | 30 hours | 6 hours | 30 hours |
| Control (no PBS) | 66 | 48 | 43 | 27 |
| Control (PBS) | 84 | 61 | 49 | 58 |
| Anti-Fas (JO2) | 12 383 | ND[1] | 876 | ND[1] |
| Anti-Fas (JO2) | 1 419 | 1 650 | 27 | 6 197 |
| IgFasL | 81 | 63 | 55 | 37 |
| IgFasL | 80 | 205 | 31 | 50 |
| IgFasL | 69 | 82 | 96 | 58 |

[1]not determined

TABLE 3

Main characteristics of the FasL-derived proteins used in the present study, in terms of production, size and cytotoxic activity.

| Proteins | Molecular weight (kDa) | Polymeric structure | EC50 (ng/mL) | EC50 (pM) | n[1] |
|---|---|---|---|---|---|
| sFasL | 27-30 | Trimer | >3000 | — | 5 |
| sfFasL | 29-32 | Trimer | >3000 | — | 5 |
| sfFasL + anti-Flag | — | ≥Hexamer | 3 +/− 1.3 | 98 +/− 43 | 5 |
| pfFasL | 37-40 | Hexamer Dodecamer | 0.6 +/− 0.4 | 15.5 +/− 11.5 | 8 |
| TCR-pfFasL | 79 | Tetramer ≥Hexamer | 3.7 +/− 1.3 | 46.7 +/− 16.2 | 10 |
| HLA-pfFasL | 85 | Tetramer ≥Hexamer | 1.6 +/− 0.4 | 19.8 +/− 5.1. | 11 |

[1]number of experiments conducted from different transfection supernatants used for the determination of the cytotoxicity EC50 values on the Jurkat cell line.

EXAMPLES

Example I

Preparation of Functional Ig-FasL Polymers

The general aims of the inventors were to develop new isoforms of functional FasL which do not require any crosslinking agent to become cytotoxic, to use them for deciphering the functional requirements leading to Fas activation, and to test them for in vivo anti-tumor activity. To reach the first goal, the inventors fused the ectodomain of FasL to the modules of the extracellular domain of the Leukemia Inhibitory Factor (LIF) cytokine receptor gp190 (9) which display a propensity to self-associate (10, 11). The gp190 belongs to the family of the hematopoietin receptors, characterized by the extracellular consensus cytokine binding domain (CBD). The gp190 harbors two CBDs (D1 and D2) separated by an immunoglobulin-like (Ig) module. Therefore, the trimeric structure of the sFasL moiety, combined to the propensity of the gp190 modules to self-associate, could lead to differently aggregated sFasL chimeras with distinct apoptotic abilities.

To reach the second goal, the inventors hypothesized that the distinct sizes of the gp190 modules (i.e. around 20, 40 and 100 kDa for Ig, D2 and D1IgD2 respectively), could exert different steric effects, distinctly impinging on the ability to trigger a productive apoptotic signal independently of the polymerization of FasL. In addition, given that Fas activation requires oligomers beyond the trimeric stage, the inventors reasoned that either aggregation of the trimers, or a particular conformational change within a single trimer triggered by a polymeric ligand, or both, is mandatory. Therefore, the inventors wondered whether anti-Fas antibody, naturally occurring sFasL and the chimeras, would be able to stimulate a chimeric Fas receptor which would only require dimerization to transmit a signal, and whether or not this property would correlate with the ability to trigger cell apoptosis. To explore this possibility, the inventors used the gp130 signal transducing cytokine receptor, another member of the hematopoietin receptors, which is pre-assembled as dimers (12) and requires a ligand-induced conformational change to become activated. Gp130 triggers cytokine-dependent proliferation of various cell lines via the Jak-STAT pathway (13). The inventors fused transmembrane and intracellular regions of gp130 to the extracellular region of Fas, generating the Fas-gp130 receptor, and expressed it in the BA/F3 cell line.

To reach the third goal, in vivo toxicity in normal mouse, and ability to counteract tumor development in a model of human solid tumor transplanted into immunodeficient mice were explored for the determined most efficient sFasL chimera.

Materials and Methods
Antibodies and Reagents

Anti-FasL mAb 14C2 and 10F2 used for the FasL ELISA (14), IgG anti-human Fas mAb 5D7 (14), isotype-matched negative controls 1F10 (IgG) and 10C9 (IgM) mAbs (15) were all generated in the laboratory. Chimeric Fas-Fc receptor was produced in the laboratory and was affinity-purified on protein A. Anti-FasL mAb (G247) used for immunoblots and anti-human Fas non agonistic mAb DX2 were purchased from BD Biosciences (Le-Pont-De-Claix, France). Recombinant sFasL (recFasL) was purchased from Alexis Corporation (Coger, Paris, France), and used with its cross-linking "enhancer" reagent, as recommended by the manufacturer. Anti-human Fas agonistic mAb 7C11 (IgM) was from Immunotech (Marseille, France). Anti-murine Fas agonistic mAb (JO2) was from Bender MedSystems (Vienna, Austria).

Construction of the FasL Chimeras

The isolation of the gp190 receptor modules Ig, D2 and D1IgD2 was described previously (10). They were fused to the extracellular domain of hFasL (amino acids 108 to 281) isolated by PCR. To generate the Fas-gp130 chimera, the Fas extracellular region and the transmembrane and intracellular domains of gp130 were isolated by site-directed mutagenesis and fused together.

Cell Lines and Transfections

The cells were grown in a 5% CO2 incubator at 37° C. without antibiotics in medium supplemented with 8% FCS (Sigma, Saint-Quentin-Fallavier, France). Culture medium was RPMI for the human Jurkat T-lymphoma and the BA/F3 pro-B-lymphocytic murine cell lines, and DMEM for the human skin carcinoma A431 and the simian epithelial COS cell lines.

COS cells were transiently transfected using the DEAE-dextran method, with 5 µg of plasmid DNA, and supernatants were harvested 5 days later. Large scale production of IgFasL was performed in serum-free Opti-MEM medium (Invitrogen).

The BA/F3 culture medium was supplemented with 10% WEHI cell-conditioned medium as a source of murine interleukin-3. BA/F3 cells ($5 \cdot 10^6$ cells in 300 µl) were electroporated (BTM 830 electroporator, BTX Instruments, Holliston, Mass.). G418 at 1 µg/ml (Invitrogen) was added at day 1. The G418-resistant cells were cloned by limiting dilution in the presence of murine IL-3. Stable transfectants were selected for membrane expression of the Fas-gp130 molecule by flow cytometry with the anti-Fas antibody 5D7. BA/F3 cell proliferation was estimated using the MTT proliferation assay, as described previously (10), after three washes of the cells to remove IL-3. The maximum value and the blank value were obtained with a saturating concentration of IL-3 or without IL3, respectively.

The BA/F3, Jurkat, COS and A431 cell lines were obtained respectively in 1991, 1995, 1992 and 2004 from Drs D'Andrea (16), Anderson (17), Kaufman (18) and Nagata (19). They are mycoplasma-tested every 6 months by PCR (20) and Hoechst 33258 staining (21). Absence of cross-contamination is verified almost daily by morphology check for all the cell lines, and by growth curve analysis in the presence and absence of IL-3 for the BA/F3 cell line.

ELISA for sFasL

FasL was quantified in cell culture supernatants using a conformation-dependent home made sandwich ELISA based on mAb 14C2 (10 µg/ml) as a capture antibody and biotinylated mAb 10F2 (1 µg/ml) as a tracer. All steps were performed exactly as reported for our anti-human LIF ELISA (22).

Western Blot Analysis

Supernatants from transfected cells were harvested and debris were removed by centrifugation. FasL was quantified and 100 ng of the FasL protein were resuspended in 5× Laemmli buffer and separated by SDS-PAGE on 12% gels. Proteins were transferred to a polyvinyldifluoride membrane (Amersham, Buckinghamshire, England) and immunoblots were performed as previously described (23). The anti-FasL mAb G247 (1 µg/ml) was incubated overnight at 4° C. BN-PAGE was carried out as described by Schägger (24) with the following modifications. A separating 4-18% w/v acrylamide linear gradient was used. Before loading, 1 µL of sample buffer (500 mM 6-amino-n-caproic acid, 5% w/v Serva Blue G) was added to the sample. The gel was run overnight at 4° C. with 1 W. Thyroglobulin (669 kDa) and BSA (66 kDa) were used as size standards (Sigma).

Surface Plasmon Resonance Analysis of the FasL Chimeras Binding to Fas

The experiments were carried out on a BIAcore 3000 optical biosensor (GE healthcare, Chalfont, UK). The FasL chimeras were produced as COS supernatants in Opti-MEM medium, concentrated 100 times, dialyzed against PBS and sterilized by filtration. Recombinant Fas-Fc (R&Dsystems, Minneapolis, Minn.) was covalently coupled to a carboxymethyl dextran flow cell (CM5, BIAcore) following the manufacturer's recommendations. The level of immobilization was 2,000 resonance units (RU). Binding of the FasL chimeras was assayed at concentrations ranging from 0.2 to 100 nM for IgFasL, 0.2 to 44 nM for cFasL, 0.2 to 37.5 nM for D2FasL, and 0.25 to 8 nM for D1IgD2FasL, in Hepes-buffered saline, at a 30 µl/min flow rate. Association was monitored for 5 min before initiating the dissociation phase for another 11 min with Hepes-buffered saline. The flow cell was regenerated with 4M MgCl2. The sensorgrams were analyzed using the BIAeval 4.1 software (BIAcore). The background of the Opti-MEM medium was at 30 RU.

Cell Cytotoxicity Assays

The cytotoxic activity of the FasL chimeras was measured using the MTT viability assay as previously described (14). The percent of specific cytotoxic activity of FasL was calculated as follows: 100−(experimental absorbance−background absorbance)/(control absorbance−background absorbance)×100.

Immunoprecipitation Experiments

For $^{35}$S metabolic labelling experiments, COS cells were transfected and the radioactive substrate ($^{35}$S-Translabel, ICN Pharmaceuticals, Orsay) was added at day 3 for an overnight incubation. The supernatants (500 µl) were incubated with 5 Ug of anti-FasL mAb 14C2 or 5 µg of purified Fas-Fc for 2 h before 40 µl of protein G beads (Sigma) were added for 1 h at 4° C. The beads were pelleted and washed 3 times with 1 ml of washing buffer (50 mM Tris, 1 mM EDTA, 150 mM sodium chloride, 0.2% Nonidet P-40, pH 8), and then resuspended in 40 µl of 5× Laemmli's buffer, boiled 5 min and the proteins were separated by SDS-PAGE using 12% gels.

Gel Filtration Experiments

The molecular size of the FasL constructs was determined using the size exclusion S-200-HR and S-300-HR Sephacryl columns (Amersham Pharmacia, Orsay, France). COS supernatants were concentrated with Centricon-30 (Millipore, Saint-Quentin-en-Yvelines, France) to reach 2 µg/ml for each sFasL form. One microgram was loaded onto a column and eluted in PBS at 0.3 ml/min. Fractions were analyzed for the presence of FasL protein by ELISA and for cytotoxicity using the MTT assay.

FasL Purification and Mice Injection

Experiments with normal Balb/cByJCr1 mice used immunoaffinity purified IgFasL. Supernatant from transfected COS cells (500 mL) was immunoprecipitated using 1 ml of anti-FasL mAb (14C2)-coupled NHS-activated sepharose beads (Amersham), overnight at 4° C. Beads were pelleted and washed in PBS, and IgFasL was eluted at pH 2 (50 mM glycine, 1 M NaCl). The eluate was immediately neutralized by adding 0.25 volume of 1 M Tris-HCl buffer at pH 8. After overnight dialysis against PBS, FasL was quantified by ELISA. Male BALB/cByJCr1 mice (8 wk old) were injected intraperitoneally with 500 µl PBS containing 10 µg of IgFasL, or of anti-Fas agonistic mAb JO2, or with PBS alone. Blood was collected at 6 and 30 h for liver enzymes measurement. The mice were euthanasied at 30 h post-injection.

For tumor experiments, COS cells were transfected with IgFasL or empty vector as a control, and grown in Opti-MEM medium. Supernatants were harvested at day 5, centrifuged, concentrated 60 times against polyethylene glycol flakes, adjusted to 100 µg/ml and sterilized by filtration. Immunodeficient Rag$^{-/-}$γc$^{-/-}$ mice, a gift from Dr Di Santo (25), were used at 7-10 weeks of age, and housed in appropriate animal facility under pathogen-free conditions. At day 0, mice received $10^5$ A431 cells in 0.1 ml of culture medium subcutaneously into the right flank. Injections of IgFasL (10 µg in 0.1 ml) or control were performed after tumor implantation, either subcutaneously at days 2 and 7, or intraperitoneally everyday between days 0 and 7, then at days 9, 11 and 14. Tumor growth was monitored by measuring maximal and minimal diameters with a calliper, three times a week, and tumor volume was estimated with the formula: tumor volume (mm$^3$)=length (mm)×width$^2$ (mm).

Statistical Analysis of Tumor Growth

The Mann Whitney test was used for the comparison between the two groups in the experiment with subcutaneous injection of IgFasL. The Kaplan-Meier analysis was used to establish the survival curves without cancer, and comparison between the two groups was made using the log-rank test. Analyses were performed with Statview Software (Abacus Concepts, Berkeley, Calif.). For all experiments, a p≤0.05 was considered significant.

Results

Generation and Production of Soluble Potentially Multimeric FasL/Gp190 Chimeras

The inventors fused the Ig, D2 and D1IgD2 modules of gp190 to the FasL extracellular region (FIGS. 1A and 1B). The constructs were expressed in COS cells and the secreted molecules were quantified using a FasL-specific ELISA. To measure their ability to trigger cell death, the inventors incubated serial dilutions of the supernatants from chimeric FasL, control mock-transfected and wild-type FasL transfected cells with Fas-sensitive Jurkat cells. A commercially available FasL (recFasL) was also tested as a highly active reference. IgFasL was the strongest death inducer among our chimeras and was as powerful as recFasL (FIG. 1C). D2FasL and D1IgD2FasL were respectively 12.5 and 125 times less potent than IgFasL. As already known, spontaneously cleaved membrane FasL had almost no activity (6, 7). The concentration of the anti-Fas agonistic IgM antibody 7C11 required to kill 50% of the Jurkat cells was at 2 ng/ml (results not shown) (14, 23, 26).

Biochemical Characterization of the FasL/Gp190 Chimeras

Identical amounts of the $^{35}$S-labeled FasL constructs were separated by SDS-PAGE (FIG. 2A, left panel) and the molecular mass of each chimera was determined under reducing conditions (FIG. 2D). The inventors also performed native gel electrophoresis (BN-PAGE) in non-reducing conditions (FIG. 2A, right panel), and observed that IgFasL, D2FasL and D1IgD2FasL all displayed much higher molecular weights than expected from the SDS-PAGE analysis (FIG. 2D). The three chimeras were also analyzed by gel filtration chromatography (FIG. 2B). Elution fractions were analyzed for the presence of FasL by ELISA (FIG. 2B, upper panel) and for cytotoxic activity against the Jurkat cell line (FIG. 2B, lower panel). The inventors confirmed that the metalloprotease-cleaved FasL is a non cytotoxic homotrimer, whereas D2FasL and D1 IgD2FasL behaved as hexamers. In contrast to D2FasL, D1 IgD2FasL did not kill the Jurkat cells, probably because it was not concentrated enough in this assay, as it is ten times less efficient than D2FasL (see also FIG. 1C). IgFasL existed under two distinct forms corresponding to a high molecular weight dodecamer and to a smaller hexameric form. Both were cytotoxic, which is consistent with previously published results for soluble FasL in the case of the hexamer (8).

The affinity of the FasL chimeras for Fas was measured using the surface plasmon resonance Biacore® method, against recombinant Fas-Fc immobilized on a chip. IgFasL, D2FasL, D1IgD2FasL and sFasL as a control, were produced as supernatants in COS cells cultured in serum-free medium, concentrated 100 times, and dialysed against PBS. The sensorgrams are depicted in FIG. 2C and the association and dissociation constants are presented in Table 1. The Kd for the three chimeras were very close to each other, ranging from 11.6 nM for IgFasL, to 25.6 nM for D1IgD2FasL and to 38.5 nM for D2FasL. They were inversely correlated with the degree of polymerisation of the construct, and two to six times higher than for non-chimeric cFasL (Kd=69.4 nM). Therefore, the small differences between the chimeras did not significantly alter the ability of the FasL moiety to bind to Fas, nor did it explain the strong discrepancies in their abilities to trigger apoptosis.

FasL Chimeras and Agonistic Antibody Differentially Act on Fas Conformation.

To determine whether a conformational change in the Fas receptor is required to produce the apoptotic signal, the inventors generated a fusion protein between the extracellular region of Fas and the transmembrane and intracellular region of the gp130 hematopoietin receptor (FIG. 3A) which we expressed in the IL-3 dependent BA/F3 murine cell line. This cell line relies on exogenously added cytokines to survive and proliferate, and also lacks membrane expression of murine Fas as shown by flow cytometry staining with the JO2 antibody (FIG. 3B, upper panel). In the presence of FasL, stable expression of the chimera was expected to keep the cells proliferating through the activation of the gp130 pathway. The membrane expression of the Fas-gp130 chimera was verified using flow cytometry, and the absence of murine Fas on the transfectants was confirmed (see FIG. 3B, lower panel, for the representative clone used in the proliferation experiments). In the absence of IL-3, the BA/F3 Fas-gp130 cells did not proliferate, demonstrating that the Fas-gp130 chimera by itself was not able to sustain cell growth (FIG. 3C).

The inventors then analyzed the effect on cell survival and proliferation of serial dilutions of the 7C11 agonistic anti-Fas antibody, of the FasL chimeras, and of spontaneously cleaved FasL (cFasL) (FIG. 3C). Cell viability was expressed as the percentage of the maximal proliferation triggered by a saturating concentration of IL-3. We observed that the strongly apoptotic 7C11 mAb was not able to sustain cell proliferation. In contrast, the pro-apoptotic IgFasL and D2FasL triggered a strong and quantitatively comparable proliferative signal, although D2FasL was 12.5 times less efficient than IgFasL for killing the Jurkat cells (see FIG. 1C). D1IgD2-FasL, which is hexameric like D2FasL but only weakly triggers cell death (see FIG. 1C), was unable to sustain cell proliferation. Cleaved FasL, which as a non apoptotic homotrimer is unable to aggregate the pre-associated Fas homotrimers, nevertheless triggered a proliferative signal comparable to that of D2FasL and IgD2FasL. The discrepancy between the polymeric apoptotic antibody 7C11 and the non apoptotic trimeric cFasL demonstrated that the proliferative signal did not require aggregation of Fas, and suggested that the triggering of Fas may also include a ligand-induced conformational change of the receptor itself.

Anti-Tumor Activity of IgFasL

The IgFasL chimera exerted its cytotoxic activity against various human tumor cells from distinct origins, both hematopoietic (OEM and H9 T-lymphoma cells, SKW6.4 and JY B-lymphoma cells, with C50 ranging from 0.01 to 0.1 µg/ml), and non-hematopoietic (A431 melanoma cells, with C50=0.15 µg/ml) (results not shown).

To determine the hepatotoxicity of IgFasL, the inventors injected the ligand in mice and we analyzed in peripheral blood the markers of liver injury aspartate amino transferase (ASAT) and alanine amino transferase (ALAT). Mice were injected intraperitoneally with 10 µg (0.7 µg/g) of affinity-purified IgFasL diluted in PBS. As controls, one mouse was injected with an identical volume of PBS and another one was left untreated. As a positive control, two mice were injected intraperitoneally with 10 µg of the agonistic anti-murine Fas antibody JO2 in the same volume of PBS. One of these mice developed a fulminant hepatitis and was sacrificed 6 hours after antibody injection. The anti-Fas JO2 mAb triggered a rapid and considerable increase of both serum amino transferases, whereas sera from the negative control mice and mice injected with the purified IgFasL did not show any sign of liver cytolysis (Table 2).

The anti-tumor activity of IgFasL was estimated in a mouse model, using human A431 cells transplanted subcutaneously to $Rag^{-/-}\gamma c^{-/-}$ immunodeficient mice. In a first experiment (FIG. 4A), the inventors analyzed whether IgFasL injected locally would control tumor growth. For that, $10^5$ A431 cells were injected to two groups of 6 mice. Then the mice received two local subcutaneous injections of either IgFasL (a non toxic amount of 10 µg in the form of a serum-free concentrated supernatant) or IgFasL-free control, at days 2 and 7 after tumor implantation. Tumor growth was regularly measured until day 21, and the evolution of tumor volumes is depicted in FIG. 4A. The local administration of IgFasL significantly reduced tumor growth, in comparison to the mice injected with the control without IgFasL, but the effect vanished when the injections were stopped. The inventors next analyzed whether injection of IgFasL at a distance from the tumor site would have a similar effect. For that, $10^5$ A431 cells were injected to two groups of 10 mice, and two independent experiments were performed. The mice received intraperitoneal injections of either IgFasL (10 µg) or IgFasL-free control, everyday from day 0 to day 7, and thereafter at days 9, 11 and 14 only. Tumor size was measured regularly until day 35. The survival of the mice without detectable tumor is presented in FIG. 4B, and shows that IgFasL is able to significantly (p=0.02) lower tumor growth and improve animal survival, as 25% of the mice having received IgFasL remain tumor-free at a time where the control mice having received medium alone are all dead from tumor overgrowth. Therefore, these in vivo experiments demonstrate that the in vitro biological properties of IgFasL are conserved in vivo.

Discussion

Our IgFasL, D2FasL and D11gD2FasL chimeras allowed us to analyze the structure-function relationships enabling FasL to activate Fas. The cytotoxic activity strongly depended on both the polymerization level of the chimera and the size of its constitutive monomers, more than on the affinity for Fas, which was very close for all three. Indeed, the most efficient construct was IgFasL, the most polymeric (dodecameric) but also the shortest one at the monomeric level. However, it is noteworthy that hexameric D1IgD2FasL was 10 times less cytotoxic than hexameric D2FasL, suggesting that the polymerization degree is not the only parameter to be important. In line with this, the IgM agonistic antibody 7C11 displays ten potential binding sites for Fas, and therefore should behave closely to the dodecameric IgFasL. However, the inventors recently demonstrated that FasL can trigger apoptosis in cells harboring a mutation in the Fas death domain at the hemizygous state, which were completely insensitive to the agonistic antibody (23). Therefore, the results of the inventors confirmed that the extent of FasL oligomerization is essential but not sufficient for triggering the apoptotic signal. The inventors therefore hypothesized that a Fas conformational change might be required as well.

The inventors explored this possibility with the cellular assay using the Fas-gp130 chimeric receptor. Trimeric cFasL, IgFasL and hexameric D2FasL efficiently triggered proliferation, but hexameric D1IgD2-FasL did not. It is possible that the voluminous D1IgD2 domain impairs the conformational change in the gp130 domain while maintaining Fas binding. This could similarly explain why it lacks cytotoxicity towards wild-type Fas. The agonistic anti-Fas antibody is also unable to trigger cell proliferation through Fas-gp130, although it efficiently triggers apoptosis (14, 26). As for D1IgD2FasL, this could be explained by structural constraints due to the IgM isotype. The apoptotic effect of the IgM mAb would then result from a large aggregation of Fas trimers, leading to caspase activation. In line with this, the non apoptotic cFasL is expected to trigger strong cell proliferation, as it is Fas natural ligand and as such must display the best fit for this receptor. As IgFasL is capable of triggering the adequate Fas conformational change and is also polymeric, this would therefore explain why it can kill cells which normally resist to the agonistic antibodies (23). These results overall confirm the inventors' reported finding that FasL and antibodies do not stimulate identically the Fas signalling machinery (26), and confirm the requirement of minimal Fas aggregation by a multimeric ligand trigger (8).

The IgFasL chimera demonstrated a very potent apoptotic activity, in the absence of any cross-linking enhancing agent. Using experiments in mouse, the inventors detected no liver damage after intravenous injection. Although these findings seem in contradiction with data showing that Fas engagement in mice induce an acute liver injury, it is noteworthy that these reports used in fact the anti-Fas JO2 agonistic antibody and not FasL (3, 27-30). The liver destruction observed following injection of anti-Fas antibodies may simply be the consequence of an antibody-dependent cell-mediated cytotoxicity reaction, as the production of inflammatory cytokines by Fc receptor-bearing Kupffer cells has been observed (31). In addition, the inventors' results confirm another report, which showed that injection of a polymeric leucine-zipper chimeric FasL in rats only triggered a mild liver damage (32). Therefore, the inventors predict that all forms of polymeric FasL which would depend on antibody-mediated cross-linking will be toxic. Using a transplanted human tumor mouse model, we then demonstrated an anti-tumor effect of a non-toxic dose of IgFasL, administered several times, locally or intraperitoneally at a distance from the tumor site. Therefore, IgFasL also demonstrated in vivo activity, by reducing tumor development. Although more experiments and higher doses are still required to better describe IgFasL toxicity and activity, it appears that for a future therapeutic use in cancer treatment, the design of soluble FasL forms spontaneously reaching a high degree of polymerization should also consider their ability to trigger the adequate Fas receptor conformational adaptation.

Example II

Preparation of Polymeric Ig-FasL (pFasL) Based Chimeras Containing a Cell-Targeting Entity Consisting of Extracellular Portions of the HLA-A2 Molecule or of a Human Gamma-Delta TCR: Cell-Targeting Chimeras.

In the following pFasL designation is used to describe polymeric Ig-FasL as defined in the present application and in particular in example I.

In Example I, report was provided of the generation of a soluble FasL chimera by fusing the immunoglobulin-like domain of the Leukemia Inhibitory Factor receptor gp190 to the extracellular region of human FasL, which enabled spontaneous homotypic polymerization of FasL in particular dodecamers production. This polymeric FasL (pFasL) displayed anti-tumoral activity in vitro and in vivo without systemic cytotoxicity in mouse. Following this work, the inventors focused on the improvement of pFasL, with two complementary objectives. Firstly, they developed more complex pFasL-based chimeras that contained a cell-targeting module. Secondly, they attempted to improve the level of production and/or the specific activity of pFasL and of the cell-targeting chimeras. Two chimeras were thus designed by fusing to pFasL the extracellular portions of the HLA-A2 molecule or of a human gamma-delta TCR, and analyzed the consequences of co-expressing these molecules or pFasL together with sFasL on their heterotopic cell production. This strategy allowed to significantly enhance the production of pFasL and of the two chimeras, as well as the cytotoxic activity of the two chimeras but not of pFasL. These results provide the proof of concept for an optimization of FasL-based chimeric proteins for a therapeutical purpose.

Two chimeras, called HLA-pfFasL and TCR-pfFasL were constructed, in which a Flag-tagged form of pFasL was respectively C-terminally linked to a beta-2 microglobulin/HLA-A*02:01 fusion molecule or to the extracellular portions of a Vγ4Vδ5 gamma-delta TCR able to recognize the cellular Endothelial Protein C receptor (EPCR). These targeting modules were selected as possible strategies to eliminate by Fas-mediated apoptosis respectively HLA-alloreactive T-lymphocytes in a transplantation setting, or carcinoma cells as EPCR is a stress self antigen over-expressed in various cancer cell types and recognized by the Vγ4Vδ5 TCR [33]. To verify their hypothesis, the inventors co-expressed with the cDNA encoding pFasL or the chimera, the one encoding the very weakly apoptotic sFasL, expecting it to be incorporated into the secreted chimeric polymer and therefore able to improve overall structure of the complex while maintaining its activity. The biochemical and functional characteristics of the complexes generated are reported here.

Materials and Methods

Cell Lines, Chemicals and Antibodies

The human Fc receptor CD32 transfected mouse fibroblastic L-cells [34], the simian epithelial COS-7 [35] and the human epithelial HEK 293T [36] cell lines were maintained in culture with DMEM (Invitrogen Gibco, Fisher Scientific, Illkirch, France). The human T-lymphoma Jurkat cells [37] were cultivated in RPMI 1640 (Invitrogen Gibco). Culture media were supplemented with 8% heat-inactivated FCS (GeHealthcare, Buckinghamshire, UK) and 2 mM L-glutamine (Sigma, Saint-Louis, USA). The PE-labelled anti-CD32 and anti-mouse IgG mAbs used for cell staining were from Immunotech Beckman Coulter (Marseille, France).

The anti-mouse Fas (clone JO-2) and the anti-human FasL (clone G247-4) mAbs were from BD Biosciences (Pont de Claix, France). The purified anti-Flag (clone M2), anti-β2 microglobulin (clone B2M-01) and anti-CD32 (clone AT10) mAbs were from Sigma, Pierce technology (Rockford, USA) and Abcam, (Cambridge, USA), respectively. The mouse anti-human FasL clones 10F2 (neutralizing) and 14C2 (non-neutralizing) mAbs were home-made [14]. The remaining chemical reagents were purchased from Sigma unless otherwise specified.

Plasmid Constructs

All the constructs were subcloned into the 5370 bp pEDr mammalian expression vector [38]. The soluble FasL (sFasL) and the soluble polymeric FasL (pFasL) constructs were described [Example I]. Regarding the TCR-pFasL, two constructs were generated by fusing the extracellular regions of the gamma4 TCR chain (aa 20 to 295) or of the delta5 TCR chain (aa 27 to 272) to the pFasL coding sequence as follows. The portion encoding the extracellular domain of the gamma4 TCR chain or of the delta5 TCR chain [33] were obtained by PCR using 5'-AATCTAGACAGCAAGT-TAAGCAAAATTC-3' (SEQ ID No:19) and 5'-AAACTAGTTGTGAGGGACATCATGTTC-3' (SEQ ID No:20) primers for the δ5 chain or 5'AATCTAGAAACT-TGGAAGGGAGAACG 3' (SEQ ID No:21) and 5'-AAACTAGTCAGGAGGAGGTACATGTA-3' (SEQ ID No:22) primers for the γ4 chain. The PCR fragments were digested by XbaI and SpeI enzymes and ligated into the pEDR-pFasL vector into the SpeI cloning site. For the HLA-pFasL construct, the extracellular domain of the HLA-A*02:01 sequence fused 3'-terminally to the beta2-microglobulin whole coding sequence kindly provided by Dr Jar-How Lee (One Lambda, Canoga Park, Calif.), was subcloned into the pFasL plasmid as follows. The fragment encompassing the signal peptide and extracellular portion of this chimera (aa 1 to 386) were isolated by PCR using 5'-AGATCTAAGGAGATATAGATATGTCTCGCTC-CGTGGCC-3' (SEQ ID No:23) and 5'-ACTAGTACTAC-CGGCACCTCCCAGGGGAGGGGCTTGGG-3' (SEQ ID No:24) primers. A 15 bp linker (GGAGGTGCCGGTAGT) (SEQ ID No:25) was added to the 3' overhang by PCR. The whole PCR fragment was ligated into the pEDr-pFasL vector between the BglII and SpeI cloning sites. A 21-bp Flag tag sequence containing 5'XbaI and 3'SpeI overhangs was added between the TCR or HLA modules and the pFasL portion by direct ligation into a SpeI site, generating the TCR-pFasL constructs. Similarly, a pfFasL and a sfFasL were obtained. All the constructs were verified by sequencing (Beckman Coulter Genomics, Takeley, UK). The final plasmids encoding sFasL, sfFasL, pfFasL, TCR-pfFasL and HLA-pfFasL displayed a nucleotide length in the range of 6000, 6000, 6300, 7100 and 7400 base pairs. For the transfection experiments using mixed plasmids, the percentage of added sFasL plasmid was determined on a molar basis.

Production of the Soluble Chimeras by Calcium Phosphate Transient Transfection

The human sFasL, sfFasL, pfFasL and HLA-pfFasL recombinant proteins were produced by transient expression in COS-7 cells whereas TCR-pfFasL was expressed in HEK 293T cells as higher amounts were produced in this cell line, according to the protocol optimized by Jordan et al [39]. One day before transfection, $1.5 \cdot 10^6$ cells were seeded in a 10 cm Petri dish in complete medium. The medium was replaced 3 to 4 hours prior to transfection. The plasmid DNA (7.6 pmol, corresponding to 30 μg in the case the sfFasL encoding plasmid) was diluted to the indicated concentration with ultrapure water and 2 M calcium chloride (70 μL/dish) to a final volume of 0.5 mL. After adding one volume of 2×HBS buffer (pH 7.05; 1.5 mM $Na_2HPO_4$, 55 mM HEPES, 274 mM NaCl) the mix was allowed to precipitate for 10 min at room temperature and added dropwise onto the plated cells. The supernatants containing targeted soluble chimeras were collected 4 days after the transfection and centrifuged 20 min at 4000 rpm at 4° C. and the pelleted debris were removed. For the TCR-pfFasL, the plasmids containing the TCR γ4 chain and the TCR δ5 chain were co-transfected in equal amounts (w/w).

Protein Quantification

The concentration of the chimeras was quantified in cell culture using specific sandwich ELISA assays. The anti-FasL 14C2 or the anti-Flag mAbs were pre-coated overnight onto 96 well ELISA plates (Maxisorp Nunc, Thermo Scientific, Rochester, USA) respectively at 1 μg or 0.25 μg/well in hydrogenocarbonate coating buffer (pH=9.6). The plate was washed 3 times with PBS containing 0.05% Tween 20 and saturated with PBS containing 1% BSA. Known quantities of sfFasL or untagged pFasL were used as standards, respectively. After a 2-hour incubation with 100 μL/well of the chimeras to be measured, the plate was washed and incubated 1 h with biotinylated anti-human FasL mAb 10F2 at 0.1 μg/well in 100 μL diluted in PBS with 1% BSA. After 3 washes, the plate was incubated for 1 h with peroxidase-labelled streptavidin (GEHealthcare) diluted 1/2000 in PBS with 1% BSA. After a 1 h incubation and a final wash step, the tetramethylbenzidine substrate (60 μg/ml in pH 5.5 citrate buffer) was added (100 μL/well). The reaction was stopped after 15 min with 1 M sulfuric acid (50 μL/well) and the plate was read at 450 nm on a spectrophotometer.

Cytotoxicity Assays

The cytotoxic activity of the chimeras was evaluated on Jurkat cells using the MTT viability assay. Cells ($3 \cdot 10^4$/well) were seeded in duplicate in flat-bottomed 96 well-plates and incubated overnight with the chimeras in a final volume of 100 μL. Then, cells were incubated for 4 h at 37° C. with the tetrazolium salt [3-(4,5-dimethyl thiazol-2yl)]-2,5-diphenyl tetrazolium bromide (Sigma), 15 μL/well at 5 mg/mL in PBS. After addition of 105 μL/well of 5% formic acid in isopropanol to solubilise the formazan precipitate, optical density was measured at 570 nm. The percentage of specific cytotoxicity of the chimera on the cells was then calculated as follows: 100−[(experimental absorbance−background absorbance Jurkat cells alone)/(control absorbance−background absorbance)]×100.

The enhancing effect of the chimera-targeting module was analyzed on L-cells stably expressing human CD32 using a propidium iodide cytotoxicity assay as follows. The HLA-pfFasL chimera was incubated during 1 h at room temperature with an anti-β2 microglobulin at 0.12 μg/ml, the anti-Flag mAb at 0.04 μg/ml or an IgG1 isotype-matched negative control at 0.12 μg/ml, to a final volume of 50 μL. These concentrations provided the optimal cross-linking effect in dose-response experiments with the L-cells. Then, 20000 L-cells were added to a final volume of 0.1 mL. Regarding the blocking experiments, L-cells were pre-incubated 30 min at RT with anti-CD32 (clone AT10) or with anti-FasL (clone 10F2) blocking mAbs at 5 μg/ml, respectively. The plates were incubated at 37° C. during 36 h. Cells and apoptotic bodies were centrifugated 10 min at 4000 rpm and resuspended with propidium iodide solution (50 μg/mL) (Sigma) diluted in hypotonic solution (0.1% trisodium citrate, 0.1% triton X100) and the percentage of cells in sub-G1 was analyzed by flow cytometry (Fortessa, BD Biosciences).

Immunoprecipitation and Immunoblot Experiments

Chimera immunoprecipitations were performed using Pansorbin® from *S. aureus* cells (EMD Millipore, Darmstadt, Germany). Pansorbin® (4 µL/condition) pre-saturated with PBS containing 3% BSA was incubated overnight at 4° C. with 3 µg of purified anti-Flag or anti-FasL 10F2 mAbs in a total volume of 1 mL. The excess of unbound mAb was removed by adding 1 mL of washing buffer (25 mM HEPES pH 7.4, 40 mM $Na_4P_2O_7$, 100 mM NaF, 40 mM $Na_3VO_4$, protease cocktail inhibitor, Triton 0.5%), followed by centrifugation (5500 rpm, 5 min, 4° C.). A fixed concentration of the chimera quantitated with the Flag/FasL ELISA was then added to the pellet to a final volume of 0.7 mL. After 4 h incubation at 4° C., the pellet was centrifuged and washed 4 times with the washing buffer. The proteins were released by heating (95° C., 5 min) in reducing loading buffer before SDS-PAGE separation.

For the immunoblot experiments, either supernatant or immunoprecipitated proteins were electrophoretically separated by SDS-PAGE on 10 or 15% gels in reducing conditions, and transferred onto nitrocellulose membrane (Biotrace NT, VWR, Fontenay-sous-bois, France) by semi-dry transfer. The membranes were stained with Ponceau red and saturated with 2.5% BSA in TBST buffer (192 mM Glycine, 25 mM Tris, 0.1% SDS, 0.05% Tween 20, pH 7.9). Immunoblots were performed with the mouse anti-human FasL G247-4 antibody at 1 µg/mL in TBST and with an IRDye@ 800CW labelled anti-mouse IgG antibody (LI-COR® ScienceTech, Courtaboeuf, France) at a 1/10000 dilution in TBST. Then, the luminescence signal were visualized and quantified by densitometry with the Odyssey® Infrared Imaging system (LICOR®).

Size Exclusion Liquid Chromatography

The apparent molecular size of the chimeras was evaluated using the Superose 6 column (GeHealthcare). The pfFasL protein was first concentrated using ammonium sulfate precipitation (47.8 g/100 ml) then dialysed overnight against PBS. The chimera was loaded in a volume of 0.2 mL onto the columns, and eluted in equilibration buffer (50 mM HEPES, 200 mM NaCl, 0.1 mM EDTA, 10% glycerol) at 0.4 mL/min. Fractions of 0.25 mL were collected. The elution profile of the recombinant proteins was evaluated by the ELISA FasL using the 14C2 and 10F2 mAbs as described above.

Statistical Analysis

Statistics were calculated with the t test using Statview (SAS Institute Corporation, Version 5.0, Cary, N.C.) software.

Results

Description of the FasL-Based Proteins

The 6 FasL-derived recombinant proteins used are depicted in FIG. 7. Besides soluble FasL (sFasL) and its Flag-tagged sfFasL counterpart, the inventors also modified pFasL to incorporate the Flag tag (leading to pfFasL). They also generated three constructs associating a cell-targeting module N-terminally to pfFasL, consisting in the extracellular regions of the HLA-A*02:01 allele fused to the beta-2 microglobulin coding sequence and of a Vγ4Vδ5 TCR, leading to the HLA-pfFasL, the γ4-pfFasL and the δ5-pfFasL molecules.

The recombinant proteins were all secreted as soluble forms in the supernatant of transfected mammalian cells. The TCR being a heterodimeric protein, the TCR-pfFasL protein was produced upon co-transfection of equal amounts of the plasmids encoding γ4-pfFasL and δ5-pfFasL. As expected, the pfFasL, TCR-pfFasL and HLA-pfFasL chimeras were polymeric, and under reducing conditions displayed apparent sizes of 37-40, 79 and 85 kDa respectively (result not shown). The low molecular weight sFasL, sfFasL and pfFasL monomers appeared as two distinct forms traducing different levels of glycosylation, as previously reported [40] and FIG. 8B]. The inventors observed that the larger chimeric proteins HLA-pfFasL and TCR-pfFasL were produced at much lower levels than sfFasL, i.e. at 36±18 ng/mL and 133±46 ng/mL respectively, versus 17±8.5 µg/ml for sfFasL, whereas the pfFasL was secreted at an intermediate level (3.3±2.9 µg/mL). Globally, increasing the complexity and the size of the chimeras deeply and negatively altered the amount of protein secreted in the culture supernatants. The size and biological activity characteristics of the FasL proteins are summarized in Table 3. Especially, the inventors observed that sFasL and sfFasL were extremely poorly cytotoxic on their own, as they were at least 5000 less active than pfFasL (C50 measured at >3000 vs 0.6+/−0.4 ng/ml, respectively). This was caused by an insufficient degree of polymerization of the soluble forms of FasL, as demonstrated by cross-linking of sfFasL with the anti-Flag antibody which allowed to recover an activity close to that of pfFasL (3+/−1.3 vs 0.6+/−0.4 ng/ml).

Enhancement of FasL-Derived Chimera Production in the Presence of sFasL

In order to improve the production of our FasL chimeras, the inventors hypothesised that decreasing the size of the polymer could enhance its release in the supernatant. To answer this point, the sFasL encoding plasmid was co-transfected together with the one encoding the Flag-tagged chimera (FIG. 8A).

First the effect on pfFasL and sfFasL production, of the co-transfection of increasing amounts of the sFasL encoding construct together a fixed amount of these plasmids was tested (FIG. 8A). Total FasL protein was measured using an ELISA with two antibodies recognizing distinct epitopes of FasL, whereas sfFasL and pfFasL were discriminated from sFasL with an ELISA using anti-Flag and anti-FasL antibodies for the capture and detection steps, respectively. The inventors observed a dose-dependent effect of the amount of the sFasL plasmid used at the transfection step, on the production of the pfFasL protein in the supernatant. In these experiments, the optimal ratio between both cDNA species was reached with 50% of the sFasL plasmid, leading to a 10-fold enhancement of the supernatant concentration of pfFasL, while the total amount of FasL-containing proteins increased concomitantly. In contrast, for the sfFasL construct, it was not possible to demonstrate any enhancing effect of sFasL on the level of Flag-tagged FasL protein produced and the total amount of FasL containing protein increased only weakly.

The higher molecular weight chimeras TCR-pfFasL and HLA-pfFasL were also examined. A significant enhancing effect of sFasL was obtained on the production of both Flag-tagged constructs, with a maximum for 12.5% and 12.5 to 25% of the amount of the TCR-pfFasL and HLA-pfFasL, respectively. This allowed to increase the amount of the chimeras by 2 and 5 fold above the plateau of production when transfected alone. In addition, as observed for pfFasL, the total amount of FasL containing protein increased with the amount of plasmid transfected, but the quantity of the Flag-tagged chimera produced significantly decreased for amounts of sFasL plasmid above the plateau value. The apparent increase in Flag-tagged protein production in the presence of sFasL, as measured with ELISA, was verified by directly immunoblotting with the anti-FasL antibody the cell culture supernatant obtained at the optimal condition of plasmid ratio. As shown in FIG. 8B for pfFasL, the cotransfection drastically increased the production of pfFasL (MW 37-40 kDa) and that sFasL was also produced (MW 27-30 kDa).

Direct Incorporation of sFasL into the pfFasL-Containing Aggregates

The inventors then assayed whether the observed increased production of the pfFasL-derived ligands in the presence of co-expressed sFasL was coincided with its incorporation into the polymeric chimera. For this purpose, the pfFasL construct was used as the prototypic example (FIG. 9A).

At first, immunoprecipitation experiments were carried out with anti-FasL or anti-Flag antibodies, followed by immunoblotting with an anti-FasL antibody. The untagged sFasL produced alone as a control was immunoprecipitated with the anti-FasL but not with the anti-Flag antibody. No sFasL was detected in the anti-FasL immunoprecipitates of the pfFasL expressed alone, and as expected it was detected after co-transfection of both plasmids. The anti-Flag antibody immunoprecipitated pfFasL when it was expressed alone or with the sFasL plasmid, and co-precipitated sFasL after co-expression of both constructs, thereby confirming our hypothesis. A densitometric analysis of the immunoblot showed that incorporation of sFasL increased with the amount of plasmid co-transfected into the cells, for an identical amount of immunoprecipitated pfFasL as quantitated with the ELISA specific for Flag-tagged FasL (FIG. 9B).

Secondly, the inventors wondered whether the presence of sFasL into the aggregates of the pfFasL chimera would modify its polymeric state and/or size. They analysed by gel filtration the protein complexes produced in the absence and in the presence of 25 or 50% of the sFasL plasmid. Total FasL was then measured in the elution fractions with the ELISA specific for FasL (FIG. 10). The inventors observed that concomitantly to the increase in proportion of the sFasL plasmid, the high molecular weight polymers were progressively lost to the benefit of smaller compounds, as expected from the inability of sFasL to trigger aggregation above the trimeric stage.

Enhancement of the Cytotoxic Activity of the FasL-Derived Chimeras in the Presence of sFasL The effect of sFasL addition within the Flag-tagged FasL complexes, on their capacity to induce apoptosis was assessed on the Fas-sensitive Jurkat cell line (FIG. 11). For this purpose, the inventors chose a concentration of the Flag-tagged proteins produced in the absence of added sFasL, which triggered a weak cytotoxicity, in the 20 to 30% range of cell death. An identical concentration of the Flag-tagged proteins, as estimated with the ELISA specific for the Flag-tagged constructs, was incubated with the target cells for each of the various sFasL plasmid ratios assayed. Differences in cell cytotoxicity would therefore reflect a higher or lower intrinsic ability of the co-expressed proteins to trigger cell death. Similarly to sFasL, which is known to barely induce apoptosis, sfFasL did not trigger cell death on its own. Cross-linking of sfFasL with an anti-Flag antibody revealed the cytotoxic potential of the protein. The presence of the sFasL protein did not modify the ability of the anti-Flag antibody cross-linked sfFasL to kill Jurkat cells, whichever the ratio between the two proteins was achieved at the transfection step. No detrimental influence of the presence of sFasL on the spontaneously cytotoxic pfFasL complexes was noticed. In contrast, the TCR-pfFasL and HLA-pfFasL both displayed a 5 to 6 fold improved cytotoxicity in the presence of sFasL plasmid at the optimal ratio of 50%, on the basis of the calculated EC50 (results not shown), when compared to the chimeric proteins expressed alone (Table 3). At higher ratios of sFasL plasmid, the gain in cytotoxic activity tended to decrease for TCR-pfFasL and HLA-pfFasL, an effect which was not observed for pfFasL.

Incorporation of sFasL does not Hinder Cell Targeting of the FasL Chimera

The apparent size decrease of the pfFasL protein complexes observed upon co-expression with sFasL, reflecting its dilution with short sFasL within the complexes, might as a corollary also diminish the cell targeting potential of the chimeras. To investigate this possibility, we analysed the ability of the HLA-pfFasL chimeric protein to target Fas-sensitive cells in a specific manner. For that purpose, we used murine fibroblastic L-cells stably expressing the human IgG Fc receptor CD32 and murine Fas (FIG. 12A) and which are sensitive to apoptosis induced by the agonistic anti-murine Fas JO-2 antibody and human FasL (FIG. 12B). The chimera complexes, by themselves exerted a cytotoxic effect on L-cells, which was enhanced by the presence of sFasL into the complexes, similarly to what was observed with the Jurkat target cells (see FIG. 11). To mimick the targeting effect mediated by the chimera, the HLA-pfFasL chimera was pre-incubated with an anti-Flag or an anti-beta-2 microglobulin, to generate immune complexes, or with an isotype-matched irrelevant monoclonal antibody as a control. The inventors used concentrations of the HLA-pfFasL chimera in the presence or absence of sFasL that triggered 15 to 25% of cell death, as measured with the ELISA specific for the Flag-tagged molecule (FIG. 12C). The targeting mediated through the anti-beta-2 microglobulin or anti-Flag antibodies via CD32 significantly enhanced by 2.5 fold the cytotoxic activity of the chimeric molecule expressed alone. In the presence of sFasL, the CD32 targeting was fully maintained, as the gain in activity was identical to what was obtained with the chimera expressed without sFasL. The dependency of the cytotoxic effect measured on the L-cells toward Fas and CD32 was verified by its abrogation in the presence of neutralising anti-FasL or a blocking anti-CD32 antibodies (FIG. 12D).

Discussion

In this report, an approach was described to improve the design of polymeric FasL-based chimeric proteins, toward a better heterotopic cellular production, and a better biological activity. This was achieved by co-expressing the chimeric protein of interest together with sFasL leading to the secretion of heteromeric complexes. At first glance, this may appear as highly counter-intuitive, as sFasL is known to display a very weak cytotoxic activity, which was confirmed in the experiments as it was at least 5000 times less active than pfFasL. However, the inventors observed that the presence of sFasL into the FasL-derived chimeras increased both their recovery in the culture supernatant and their proapoptotic functional activity.

The gain in net production relied on the complexity and/or the size of the FasL-based unit constituting the polymer, which by itself already greatly influenced the level of production that could be spontaneously reached. No effect was observed of coexpressed sFasL on the net production of the trimeric sfFasL, which is already produced at saturating levels when expressed alone in the optimized experimental conditions used. For pfFasL, which is polymeric and consists mainly of hexamers and dodecamers, the production of this chimera was enhanced by up to 10 fold in the presence of sFasL, allowing to reach an optimal production level close to that obtained for sFasL at its maximum. For more complex FasL-based units, such as HLA-pfFasL and TCR-pfFasL, the production was also improved although to a lower 2 to 5-fold extent. As these chimeras were secreted at much lower levels than the smaller forms, the inventors concluded that significantly improving their production is indeed possible but that intrinsic constraints, such as are e.g. the size of the monomer, of the final polymer or of both, will nevertheless auto-limit the capacity of the cell to produce and/or release them. The phenomenon described in the present report did not appear to be limited neither to a specific chimeric construct, as it was successfully observed it with three different ones, nor to be dependent on a cell production system, as the TCR and HLA chimeras were produced in HEK and COS cells, respectively. In experiments not shown, similar results were obtained for the pfFasL alone or in combination with sFasL in a very different context, i.e. a stable production system following transduction of HEK cells with two retroviral constructs each encoding one FasL-derived molecule. The obtained results also showed that the gain in protein production reached a maximum before decreasing when the proportion of sFasL becomes too important, as was observed for sfFasL, pfFasL, HLA-pfFasL and TCR-pfFasL. This could suggest that an overwhelming production of sFasL tends to divert the cellular machinery from the manufacturing of the HLA-pfFasL and TCR-pfFasL chimeras.

The gain in function observed was also dependent on the complexity of the FasL-based unit composing the polymer, with some differences when compared to the improvement in production. For sfFasL, no cytotoxic function appeared whichever the proportion of non-tagged sFasL was present, consistent with the fact that sFasL is not expected to be able to alter the polymerisation level of sfFasL, which by itself is trimeric as sFasL is [41]. No gain in function was noticed either in the presence of the cross-linking anti-Flag antibody, suggesting that the spatial intrinsic organisation of the sfFasL +anti-Flag antibody is close to its functional optimum, and therefore can not be improved further with sFasL. This is confirmed with the pfFasL chimera, as no improvement in cytotoxic efficiency was observed in the presence of sFasL, although we reported a strong increase in the amount of protein produced. This discrepancy between these two criteria also suggests that the spatial organisation of the pfFasL chimera is already optimal in the absence of sFasL, and that only its intracellular processing or release can be optimized. For the HLA-pfFasL and TCR-pfFasL species, which were produced to much lower amounts, the cytotoxic activity was significantly enhanced, in addition to an improvement in cell production, in the presence of sFasL. Therefore, the gain occurs at both steps. However, although the overall raise might be considered as modest at each step, this may be explained by the nature of the chimeras that were produced. Indeed, a γ4δ5 TCR is a non covalently-linked heterodimeric protein with a natural propensity for the two chains to interact with each other into a stable dimer. In experiments not shown, it was noticed that none of the two chimeric chains was produced alone, in the absence of the co-transfection of its partner, suggesting that the pre-association of the TCR chains is a pre-requisite to the release of the TCR-pfFasL chimera. Therefore, such a polymeric chimera is intrinsically complex in terms of structure, which may explain why the spontaneous production level is low, and also why it cannot drastically be improved. An alternative would be to generate a single chain construct, on the model of what has been done for a TCR of the alpha-beta type. In the case of HLA-pfFasL, the construct used consisted in a first single chain beta-2 microgulin HLA fusion, secondly attached to the FasL moiety, so it was also in itself a complex molecule. In addition, HLA stability is highly dependent on the presence of a peptide into the peptide-binding groove, which may also impinge on the overall 30 stability of the chimera. Results obtained also showed that the gain in cytotoxic activity for HLA-pfFasL and TCR-pfFasL reached a maximum before decreasing in the presence of higher proportions of sFasL. This could reflect a decrease in the overall size of the chimeric proteins, below the minimal degree of polymerization required for a biologically active molecule.

The gel filtration experiments which were conducted showed a progressive decrease in the average size of the pfFasL chimera as the amount of sFasL increased: the high molecular weight compound disappeared at the benefit of smaller forms. This would explain both the increase in production due to the handling by the cell machinery of smaller complexes, and the enhancement of the activity if assuming that the most polymeric complexes are not the most efficient ones. However, and as observed for the production of the chimeras, the gain in activity may also be followed by a significant loss when the proportion of sFasL becomes too important, as it was indeed observed for HLA-pfFasL and TCR-pfFasL. This suggests that an overwhelming production of sFasL leads to the decrease in the proportion of chimera polymers of a size compatible with a biological activity.

The present work demonstrates that the production and/or apoptotic activity of FasL-derived chimeras can be enhanced by incorporating the almost non cytotoxic ligand sFasL, thereby improving the obtention of more complex chimeric proteins equipped with a cell targeting module. The results suggest that this design could improve the efficacy of cell type-selective chimeras, as the inventors describe that the cytotoxicity of the HLA-pfFasL towards Fas-sensitive cells is indeed specifically improved in a cellular model where the chimera is tethered onto the surface of a presenting cell via an anti-beta2 microgulin or an anti-Flag antibody. Then, the approach described here suggests that the design of FasL-derived chimeras associating two different cell-targeting modules is possible, with possibly a synergy as the coexpression of two different monomers could lead to a copolymer with a higher activity than each constitutive compound.

Example III

Preparation of Polymeric Ig-FasL (pFasL) Based Chimeras Containing a Cell-Targeting Entity Consisting of CD80 Extracellular Domain In the present work, a CD80-pFasL chimera to target human myeloma cells was designed, because, 1) they are known to express the CD80 receptor CD28 and 2) the expression level of CD28 is correlated with rapid disease progression and worse prognostic. Using the T-lymphoblast Jurkat and myeloma cell lines, the inventors demonstrated that the CD80-pFasL chimera was cytotoxic in a Fas-dependent manner and that its activity was significantly enhanced by the CD80/CD28 interaction. The CD28 synergistic activity was independent of any signalling through the CD28 intracellular domain, and was correlated with the expression level of CD28 on the target cell. The co-expression of soluble FasL (sFasL) together with the chimera increased its cytotoxic activity without impairing its ability to target the CD28-expressing cells. These results suggest that the CD28 tumor-enhancing receptor is a potential target for immunotherapy in myeloma.

The inventors constructed the CD80-pFasL (also designated CD80-IgFasL polymeric chimera), with the objective to eliminate in a selective manner the tumoral plasmocytes in the multiple myeloma disease. Myeloma cells express CD80, the CD80 receptor, and the expression level of CD28 is correlated with rapid disease progression and a worse prognostic. CD28 is known to participate in cell survival and proliferation, via the activation of the NF-kB pathway. CD28 is expressed on normal plasmocytes as well, but is absent from the surface of other cells of the B-lymphocyte lineage. CD28 is also expressed on normal resting and activated T-lymphocytes, and for these cells is a prototypic co-stimulator, which is required for naïve T-cells to be activated into effector lymphocytes, in conjunction to the signal triggered by interaction between the cognate peptide-HLA complex and the T-cell antigen receptor (TCR). In the present report, the biochemical and functional characteristics of the CD80-pFasL molecule are described, focusing on its ability to trigger apoptosis of myeloma cell lines.

Materials and Methods

Cell Lines, Chemicals and Antibodies

The human epithelial HEK 293T (36) cell line was maintained in culture with DMEM (Invitrogen Gibco, Fisher Scientific, Illkirch, France). The human T-lymphoma Jurkat cells (37) and the human myeloma cell lines RPMI8226 and U266 were cultivated in RPMI 1640 (Invitrogen Gibco). Culture media were supplemented with 8% heat-inactivated FCS (GeHealthcare, Buckinghamshire, UK) and 2 mM L-glutamine (Sigma, Saint-Louis, USA). The PE-labelled anti-Fas, anti-CD80, anti-CD28 (clone CD28.2) and anti-mouse IgG mAbs were from Immunotech Beckman Coulter (Marseille, France). The anti-mouse Fas (clone JO-2) and the anti-human FasL (clone G247-4) mAbs were from BD Biosciences (Pont de Claix, France). The purified anti-Flag (clone M2) mAb was from Sigma. The mouse anti-human FasL clones 10F2 (neutralizing) and 14C2 (non-neutralizing) mAbs were home-made (14). The remaining chemical reagents were purchased from Sigma unless otherwise specified.

Plasmid Constructs

All the constructs were subcloned into the 5370 bp pEDr mammalian expression vector (38). The soluble FasL (sFasL) and the soluble polymeric FasL (pFasL) constructs were described above (Example I). The CD80-pFasL was obtained by subcloning the 720 bp fragment encoding the extracellular region of human CD80, upstream the immunoglobulin-like module of the pFasL construct, done for the reported pFasL chimers (in Example II). The CD80-pFasL construct was verified by sequencing (Beckman Coulter Genomics, Takeley, UK).

Production of the Soluble Chimeras by Calcium Phosphate Transient Transfection

The human sFasL, pFasL and CD80-pFasL recombinant proteins were produced by transient expression in HEK 293T cells according to the protocol optimized by Jordan et al (39). One day before transfection, $1.5 \cdot 10^6$ cells were seeded in a 10 cm Petri dish in complete medium. The medium was replaced 3 to 4 hours prior to transfection. The plasmid DNA (30 µg) was diluted with ultrapure water and 2 M calcium chloride (70 µL/dish) to a final volume of 0.5 mL. After adding one volume of 2×HBS buffer (pH 7.05; 1.5 mM $Na_2HPO_4$, 55 mM HEPES, 274 mM NaCl) the mix was allowed to precipitate for 10 min at room temperature and added dropwise onto the plated cells. The supernatants were collected 4 days after the transfection and centrifuged 20 min at 4000 rpm at 4° C. and the pelleted debris were removed. For experiments using the co-transfection of two different plasmids, 30 µg of the CD80-encoding plasmid was used, to which was added the indicated amount of the second plasmid.

Protein Quantification

The concentration of the chimeras was quantified in cell culture using specific sandwich ELISA assays. The anti-FasL 14C2 or the anti-Flag mAbs were pre-coated overnight onto 96 well ELISA plates (Maxisorp Nunc, Thermo Scientific, Rochester, USA) respectively at 1 µg or 0.25 µg/well in hydrogenocarbonate coating buffer (pH=9.6). The plate was washed 3 times with PBS containing 0.05% Tween 20 and saturated with PBS containing 1% BSA. Known quantities of sfFasL or untagged pFasL were used as standards, respectively. After a 2-hour incubation with 100 µL/well of the chimeras to be measured, the plate was washed and incubated 1 h with biotinylated anti-human FasL mAb 10F2 at 0.1 µg/well in 100 µL diluted in PBS with 1% BSA. After 3 washes, the plate was incubated for 1 h with peroxidase-labelled streptavidin (GEHealthcare) diluted 1/2000 in PBS with 1% BSA. After a 1 h incubation and a final wash step, the tetramethylbenzidine substrate (60 µg/ml in pH 5.5 citrate buffer) was added (100 µL/well). The reaction was stopped after 15 min with 1 M sulfuric acid (50 µL/well) and the plate was read at 450 nm on a spectrophotometer.

ELISA for CD80-pFasL

The sandwich ELISA used to quantitate the CD80-pFasL molecule was performed using as the capture antibody the anti-CD80 (5 µg/mL) and as the tracing antibody the biotinylated 14C2 anti-FasL mAb. The ELISA procedure was performed exactly as described for the other ELISA assays we reported to quantitate our FasL-derived chimeras (Example II).

Cytotoxicity Assays

The cytotoxic activity of the chimeras was evaluated on the indicated cells using the MTT viability assay. Cells ($3 \cdot 10^4$/well) were seeded in duplicate in flat-bottomed 96 well-plates and incubated overnight with the chimeras in a final volume of 100 µL. Then, cells were incubated for 4 h at 37° C. with the tetrazolium salt [3-(4,5-dimethyl thiazol-2yl)]-2,5-diphenyl tetrazolium bromide (Sigma), 15 µL/well at 5 mg/mL in PBS. After addition of 105 µL/well of 5% formic acid in isopropanol to solubilise the formazan precipitate, optical density was measured at 570 nm. The percentage of specific cytotoxicity of the chimera on the cells was then calculated as follows: 100−[(experimental absorbance−background absorbance of cells alone)/(control absorbance−background absorbance)]×100.

The enhancing effect of the CD80 module was analyzed on the indicated target cells as follows. The cells or the chimera were incubated during 30 min at 37° C. or at room temperature, respectively, with the indicated antibody at the indicated concentration in a total volume of 50 µl. Then, 20000 L-cells were added to a final volume of 0.1 mL, and the plates were incubated at 37° C. for 24 h, before measuring cell viability with the MTT assay.

Immunoprecipitation and Immunoblot Experiments

Chimera immunoprecipitations were performed using Pansorbin® from *S. aureus* cells (EMD Millipore, Darmstadt, Germany). Pansorbin® (4 µL/condition) pre-saturated with PBS containing 3% BSA was incubated overnight at 4° C. with 3 µg of purified anti-CD28 mAb in a total volume of 1 mL. The excess of unbound mAb was removed by adding 1 mL of washing buffer (25 mM HEPES pH 7.4, 40 mM $Na_4P_2O_7$, 100 mM NaF, 40 mM $Na_3VO_4$, protease cocktail inhibitor, Triton 0.5%), followed by centrifugation (5500 rpm, 5 min, 4° C.). A fixed concentration of the chimera quantitated with the CD80/FasL ELISA was then added to the pellet to a final volume of 0.7 mL. After 4 h incubation at 4° C., the pellet was centrifuged and washed 4 times with the washing buffer. The proteins were released by heating (95° C., 5 min) in reducing loading buffer before SDS-PAGE separation.

For the immunoblot experiments, either supernatant or immunoprecipitated proteins were electrophoretically separated by SDS-PAGE on 10 or 15% gels in reducing conditions, and transferred onto nitrocellulose membrane (Biotrace NT, VWR, Fontenay-sous-bois, France) by semi-dry transfer. The membranes were stained with Ponceau red and saturated with 2.5% BSA in TBST buffer (192 mM Glycine, 25 mM Tris, 0.1% SDS, 0.05% Tween 20, pH 7.9). Immunoblots were performed with the mouse anti-human FasL G247-4 antibody at 1 µg/mL in TBST and with an IRDye® 800CW labelled anti-mouse IgG antibody (LI-COR® ScienceTech, Courtaboeuf, France) at a 1/10000 dilution in TBST. Then, the luminescence signal were visualized and quantified by densitometry with the Odyssey® Infrared Imaging system (LICOR®).

Statistical Analysis

Statistics were calculated with the t test using Statview (SAS Institute Corporation, Version 5.0, Cary, N.C.) software.

Results and Discussion

Description of the FasL-Based Proteins

The FasL-derived recombinant proteins used are depicted in FIG. 13, panel A. The pFasL was modified by fusing 5-terminally, the extracellular module of CD80, leading to CD80-pFasL. The sFasL, pFasL and CD80-pFasL recombinant proteins were all secreted as soluble forms in the supernatant of transfected mammalian cells. The CD80-pFasL was polymeric, and under reducing conditions displayed an apparent size of 80 kDa (FIG. 13, panel B). The inventors observed that the larger chimeric protein CD80-pFasL was produced comparably to pFasL (1.8±0.7 µg/mL versus 3.3±2.9 µg/mL, respectively), but to a much lower amount than sFasL (17±8.5 µg/ml) (result not shown).

Involvement of CD28 Binding but not Signalling in Apoptosis Induced by CD80-pfFasL To analyse the cytotoxic activity of the CD80-pFasL chimera, the T-lymphoblastic cell line Jurkat, which is highly sensitive to Fas-mediated cell death, and also expresses CD28 was used (FIG. 14, panel A). A Jurkat cell clone selected from the Jurkat parent cell line, for its very low expression of CD28 (clone CD28low), and a clone derived from the CD28low one which stably expressed upon transfection, a truncated form of CD28 where the entire cytoplasmic region of CD28 had been removed (clone CD28delta) were also used. Both expressed Fas at a level comparable to the parent cell line (FIG. 14, panel A) and have been described previously (43).

In terms of apoptotic activity (FIG. 14, panel B), the CD80-pFasL was efficient towards the JKCD28low cell line, but displayed a weaker efficiency than the pFasL chimera (C50 of 7 vs 0.4 ng/mL, respectively, i.e. a 17 fold decrease), whereas sFasL was not active. The CD80-pFasL chimera was highly cytotoxic on its own towards the JK parent (i.e. the JKCD28high) cell line (FIG. 14, panel B), and closely to pFasL (C50 of 3 versus 1.2 ng/ml, respectively, i.e. a 2.5 fold decrease), and more efficient towards the JKCD28delta cell line than the pFasL construct (C50 of 0.2 vs 2 ng/mL, respectively, i.e. a 10 fold increase). These results showed that the CD80 module did not abrogate the capability of the chimera to trigger apoptosis via its FasL module. However, as the C50 of CD80-pFasL was increased when compared to pFasL, this suggested that it could indeed decrease the efficiency of the death signal through Fas, either because a non optimal spatial conformation due for example to a steric hindrance conferred by the CD80 module, or to an inhibition of the death signalling pathway because of the triggering of the CD28 signalling cascade through CD28, or both. Of note, the CD80-pFasL chimera was found to be more active towards the CD28delta cell line than the pFasL construct. Although this could suggest the participation of the CD28 intracellular region to an inhibition of the apoptotic Fas-dependent signal, the strongly divergent levels of membrane expression of CD28 between these two cell lines does not allow to conclude, as the ability to bind the chimera through CD28 should modulate its efficiency to kill the targeted cells via the FasL module, independently of any action of the CD28 receptor.

To analyse this possibility, the inventors conducted experiments where CD28 was blocked using a neutralising antibody. The blocking of CD28 led to a partial inhibition of cell death on the JKCD28high cell line, whereas no effect was evidenced on the JKCD28low cell line, which expresses almost no CD28 on the cell surface. This demonstrated that the CD80 module indeed bound to CD28 to trigger cell death via the FasL module. In addition, because the blocking of this interaction strongly impaired cell killing, this suggests that the binding through CD28 did not diminish the efficiency of the chimeric protein, as the killing would have increased in the presence of the blocking anti-CD28 antibody (FIG. 14, panel C).

Effect of CD80-pFasL on Human Myeloma Cell Lines

The human myeloma cell lines RPMI8226 and U266 coexpress Fas and CD28 on the cell surface (FIG. 15, panel A). The pFasL and CD80-pFasL chimera were tested against these two cell lines (FIG. 15, panel B). Both were sensitive to pFasL and to CD80-pFasL, although 10 to 100 less than the Jurkat cell line (results not shown). To demonstrate the involvement of the CD80 module into the cytotoxic activity of the chimera, the inventors performed inhibition experiments in the presence of the anti-CD28 blocking antibody. As observed for the JK cell lines, the blocking of CD28 led to a strong decrease of the cytotoxic activity of the CD80-pFasL chimera but not of pFasL, thereby demonstrating the involvement of the CD28 receptor in the activity of the chimeric protein.

Improvement of CD80-pfFasL in the Presence of sFasL

As demonstrated (Example II) with two different pFasL-derived chimeric proteins, the inventors observed that the cell supernatant production of CD80-pFasL was enhanced upon co-expression together with sFasL, with a maximal effect in the presence of 1.5 to 50% of the sFasL plasmid (FIG. 16, panel A). Immunoprecipitation with the anti-CD80 antibody followed by immunoblotting with the anti-FasL antibody demonstrated the presence of sFasL into the chimera polymers only after the co-transfection of both plasmids (FIG. 16, panel B). CD80-pFasL chimera produced in the presence of sFasL have also been produced and their cytotoxic activity is under assay, in order to determine the gain of activity due to the incorporation of sFasL into the chimera polymer.

REFERENCES

1. Bodmer, J. L., Schneider, P., and Tschopp, J. The molecular architecture of the TNF superfamily. Trends Biochem Sci, 27: 19-26, 2002.
2. Krueger, A., Fas, S. C., Baumann, S., and Krammer, P. H. The role of CD95 in the regulation of peripheral T-cell apoptosis. Immunol Rev, 193: 58-69, 2003.

3. Ogasawara, J., Watanabe-Fukunaga, R., Adachi, M., Matsuzawa, A., Kasugai, T., Kitamura, Y., Itoh, N., Suda, T., and Nagata, S. Lethal effect of the anti-Fas antibody in mice. Nature, 364: 806-809, 1993.
4. Kayagaki, N., Kawasaki, A., Ebata, T., Ohmoto, H., Ikeda, S., Inoue, S., Yoshino, K., Okumura, K., and Yagita, H. Metalloproteinase-mediated release of human Fas ligand. J Exp Med, 182: 1777-1783, 1995.
5. Mariani, S. M., Matiba, B., Baumler, C., and Krammer, P. H. Regulation of cell surface APO-1/Fas (CD95) ligand expression by metalloproteases. Eur J Immunol, 25: 2303-2307, 1995.
6. Suda, T., Hashimoto, H., Tanaka, M., Ochi, T., and Nagata, S. Membrane Fas ligand kills human peripheral blood T lymphocytes, and soluble Fas ligand blocks the killing. J Exp Med, 186: 2045-2050, 1997.
7. Schneider, P., Holler, N., Bodmer, J. L., Hahne, M., Frei, K., Fontana, A., and Tschopp, J. Conversion of membrane-bound Fas(CD95) ligand to its soluble form is associated with downregulation of its proapoptotic activity and loss of liver toxicity. J Exp Med, 187: 1205-1213, 1998.
8. Holler, N., Tardivel, A., Kovacsovics-Bankowski, M., Hertig, S., Gaide, O., Martinon, F., Tinel, A., Deperthes, D., Calderara, S., Schulthess, T., Engel, J., Schneider, P., and Tschopp, J. Two adjacent trimeric Fas ligands are required for Fas signaling and formation of a death-inducing signaling complex. Mol Cell Biol, 23: 1428-1440, 2003.
9. Gearing, D. P., Thut, C. J., VandeBos, T., Gimpel, S. D., Delaney, P. B., King, J., Price, V., Cosman, D., and Beckmann, M. P. Leukemia inhibitory factor receptor is structurally related to the IL-6 signal transducer, gp130. Embo J, 10: 2839-2848, 1991.
10. Taupin, J. L., Miossec, V., Pitard, V., Blanchard, F., Daburon, S., Raher, S., Jacques, Y., Godard, A., and Moreau, J. F. Binding of leukemia inhibitory factor (LIF) to mutants of its low affinity receptor, gp190, reveals a LIF binding site outside and interactions between the two cytokine binding domains. J Biol Chem, 274: 14482-14489, 1999.
11. Voisin, M. B., Bitard, J., Daburon, S., Moreau, J. F., and Taupin, J. L. Separate functions for the two modules of the membrane-proximal cytokine binding domain of glycoprotein 190, the leukemia inhibitory factor low affinity receptor, in ligand binding and receptor activation. J Biol Chem, 277: 13682-13692, 2002.
12. Tenhumberg, S., Schuster, B., Zhu, L., Kovaleva, M., Scheller, J., Kallen, K. J., and Rose-John, S. gp130 dimerization in the absence of ligand: preformed cytokine receptor complexes. Biochem Biophys Res Commun, 346: 649-657, 2006.
13. Boulanger, M. J. and Garcia, K. C. Shared cytokine signaling receptors: structural insights from the gp130 system. Adv Protein Chem, 68: 107-146, 2004.
14. Legembre, P., Moreau, P., Daburon, S., Moreau, J. F., and Taupin, J. L. Potentiation of Fas-mediated apoptosis by an engineered glycosylphosphatidylinositol-linked Fas. Cell Death Differ, 9: 329-339, 2002.
15. Taupin, J. L., Acres, B., Dott, K., Schmitt, D., Kieny, M. P., Gualde, N., and Moreau, J. F. Immunogenicity of HILDA/LIF either in a soluble or in a membrane anchored form expressed in vivo by recombinant vaccinia viruses. Scand J Immunol, 38: 293-301, 1993.
16. D'Andrea, A. D., Yoshimura, A., Youssoufian, H., Zon, L. I., Koo, J. W., and Lodish, H. F. The cytoplasmic region of the erythropoietin receptor contains nonoverlapping positive and negative growth-regulatory domains. Mol Cell Biol, 11: 1980-1987, 1991.
17. Tian, Q., Taupin, J., Elledge, S., Robertson, M., and Anderson, P. Fas-activated serine/threonine kinase (FAST) phosphorylates TIA-1 during Fas-mediated apoptosis. J Exp Med, 182: 865-874, 1995.
18. Messier, T. L., Pittman, D. D., Long, G. L., Kaufman, R. J., and Church, W. R. Cloning and expression in COS-1 cells of a full-length cDNA encoding human coagulation factor X. Gene, 99: 291-294, 1991.
19. Nagata, S., Onda, M., Numata, Y., Santora, K., Beers, R., Kreitman, R. J., and Pastan, I. Novel anti-CD30 recombinant immunotoxins containing disulfide-stabilized Fv fragments. Clin Cancer Res, 8: 2345-2355, 2002.
20. Uphoff, C. C. and Drexler, H. G. Detection of mycoplasma contaminations. Methods Mol Biol, 290: 13-23, 2005.
21. Chen, T. R. In situ detection of mycoplasma contamination in cell cultures by fluorescent Hoechst 33258 stain. Exp Cell Res, 104: 255-262, 1977.
22. Taupin, J. L., Gualde, N., and Moreau, J. F. A monoclonal antibody based elisa for quantitation of human leukaemia inhibitory factor. Cytokine, 9: 112-118, 1997.
23. Beneteau, M., Daburon, S., Moreau, J. F., Taupin, J. L., and Legembre, P. Dominant-negative Fas mutation is reversed by down-expression of c-FLIP. Cancer Res, 67: 108-115, 2007.
24. Schagger, H. Respiratory chain supercomplexes of mitochondria and bacteria. Biochim Biophys Acta, 1555: 154-159, 2002.
25. Goldman, J. P., Blundell, M. P., Lopes, L., Kinnon, C., Di Santo, J. P., and Thrasher, A. J. Enhanced human cell engraftment in mice deficient in RAG2 and the common cytokine receptor gamma chain. Br J Haematol, 103: 335-342, 1998.
26. Legembre, P., Beneteau, M., Daburon, S., Moreau, J. F., and Taupin, J. L. Cutting edge: SDS-stable Fas microaggregates: an early event of Fas activation occurring with agonistic anti-Fas antibody but not with Fas ligand. J Immunol, 171: 5659-5662, 2003.
27. Chida, Y., Sudo, N., Takaki, A., and Kubo, C. The hepatic sympathetic nerve plays a critical role in preventing Fas induced liver injury in mice. Gut, 54: 994-1002, 2005.
28. Descamps, D., Vigant, F., Esselin, S., Connault, E., Opolon, P., Perricaudet, M., and Benihoud, K. Expression of non-signaling membrane-anchored death receptors protects murine livers in different models of hepatitis. Hepatology, 44: 399-409, 2006.
29. Krautwald, S., Ziegler, E., Tiede, K., Pust, R., and Kunzendorf, U. Transduction of the TAT-FLIP fusion protein results in transient resistance to Fas-induced apoptosis in vivo. J Biol Chem, 279: 44005-44011, 2004.
30. Song, E., Lee, S. K., Wang, J., Ince, N., Ouyang, N., Min, J., Chen, J., Shankar, P., and Lieberman, J. RNA interference targeting Fas protects mice from fulminant hepatitis. Nat Med, 9: 347-351, 2003.
31. Matsuda, Y., Toda, M., Kato, T., Kuribayashi, K., and Kakimi, K. Fulminant liver failure triggered by therapeutic antibody treatment in a mouse model. Int J Oncol, 29: 1119-1125, 2006.
32. Shiraishi, T., Suzuyama, K., Okamoto, H., Mineta, T., Tabuchi, K., Nakayama, K., Shimizu, Y., Tohma, J., Ogihara, T., Naba, H., Mochizuki, H., and Nagata, S. Increased cytotoxicity of soluble Fas ligand by fusing isoleucine zipper motif. Biochem Biophys Res Commun, 322: 197-202, 2004.

33. Willcox C, Pitard V, Netzer S, Couzi L, Salim M, et al. (2012) Cytomegalovirus and tumor stress-surveillance by human γδ T cell receptor binding to Endothelial Protein C Receptor. Nat Immunol 13: 872-879.
34. Banchereau J, de Paoli P, Valle A, Garcia E, Rousset F (1991) Long-term human B cell lines dependent on interleukin-4 and antibody to CD40. Science 251: 70-72.
35. Gluzman Y (1981) SV40-transformed simian cells support the replication of early SV40 mutants. Cell 23: 175-182.
36. Sena-Esteves M, Saeki Y, Camp S M, Chiocca E A, Breakefield X O (1999) Single-step conversion of cells to retrovirus vector producers with herpes simplex virus-Epstein-Barr virus hybrid amplicons. J Virol 73: 10426-10439.
37. Vivier E, Rochet N, Ackerly M, Petrini J, Levine H, et al. (1992) Signaling function of reconstituted CD16: zeta: gamma receptor complex isoforms. Int Immunol 4: 1313-1323.
38. Kaufman R J, Davies M V, Wasley L C, Michnick D (1991) Improved vectors for stable expression of foreign genes in mammalian cells by use of the untranslated leader sequence from EMC virus. Nucleic Acids Res 19: 4485-4490.
39. Jordan M, Wurm F (2004) Transfection of adherent and suspended cells by calcium phosphate. Methods 33: 136-143.
40. Schneider P, Bodmer J L, Holler N, Mattmann C, Scuderi P, et al. (1997) Characterization of Fas (Apo-1, CD95)-Fas ligand interaction. J Biol Chem 272: 18827-18833.
41. Holler N, Tardivel A, Kovacsovics-Bankowski M, Hertig S, Gaide O, et al. (2003) Two adjacent trimeric Fas ligands are required for Fas signaling and formation of a death-inducing signaling complex. Mol Cell Biol 23: 1428-1440.
42. Belmont H J, Price-Schiavi S, Liu B, Card K F, Lee H I, et al. (2006) Potent antitumor activity of a tumor-specific soluble TCR/IL-2 fusion protein. Clin Immunol 121: 29-39.
43. Legembre P, Daburon S, Moreau P, Moreau J F, Taupin J L. Modulation of Fas-mediated apoptosis by lipid rafts in T lymphocytes. *J Immunol* 2006 Jan. 15; 176 (2): 716-720.

The invention claimed is:

1. A chimeric molecule comprising a monomeric structure (IgFasL), the monomeric structure consisting of, from the N-terminal end to the C-terminal end, the following domains directly fused to each other in that order:
   a) an Ig-like domain of the human Leukemia Inhibitory Factor (LIF) receptor gp190 consisting of the amino acid sequence of SEQ ID NO: 4;
   b) a peptide linker consisting of the amino acid sequence of SEQ ID NO: 6; and
   c) an extracellular domain of the human FasL protein consisting of the amino acid sequence of SEQ ID NO: 8;
   wherein the chimeric molecule is a polymer of at least 6 repeats of said monomeric structure, said polymer being able to bind to and/or activate the Fas transmembrane receptor on Fas expressing cells, said polymer having a cytotoxic activity toward Fas expressing cells.

2. The chimeric molecule according to claim 1, which comprises a homohexameric structure of the extracellular domain of said FasL protein or comprises a homododecameric structure of the extracellular domain of said FasL protein.

3. The chimeric molecule according to claim 1, wherein the molecule binds the Fas receptor expressed on cells and triggers a conformational change of said Fas receptor.

4. The chimeric molecule according to claim 3, wherein the cells are human cells.

5. The chimeric molecule according to claim 1, further comprising a heterologous polypeptidic domain suitable for targeting specific cells or for targeting receptors on specific cells, said heterologous polypeptidic domain consisting of the extracellular domain of the human CD80 ligand consisting of the amino acid sequence of SEQ ID NO: 16.

6. The chimeric molecule according to claim 5, comprising the amino acid sequence of SEQ ID NO: 18.

7. The chimeric molecule according to claim 5, wherein the heterologous polypeptidic domain is suitable for targeting tumor antigens on specific cells.

8. The chimeric molecule according to claim 1, wherein the molecule is a heteropolymer chimeric molecule comprising
   monomers consisting of said IgFasL, and
   monomers of soluble human FasL (sFasL),
   wherein the proportion of sFasL with respect to said IgFasL is less than 50%.

9. The chimeric molecule according to claim 8, wherein the proportion of sFasL with respect to said IgFasL is from 10% to 20%.

10. The chimeric molecule according to claim 1, wherein the polymer is a homopolymer.

11. The chimeric molecule according to claim 1, wherein the monomeric structure consists of the amino acid sequence of SEQ ID NO: 12.

12. The chimeric molecule according to claim 1, comprising a signal peptide before said IgFasL monomer for production in cells and secretion from the cells, the signal peptide comprising the amino acid sequence of SEQ ID NO: 10.

13. The chimeric molecule according to claim 12, comprising the amino acid sequence of SEQ ID NO: 2.

14. A nucleic acid molecule which encodes the chimeric molecule of claim 1.

15. The nucleic acid molecule according to claim 14, which comprises the following functional domains directly fused to each other and organized as follows from its 5' to its 3' end:
   (i) optionally a nucleotide sequence encoding a signal peptide for production in cells and secretion, and consisting of the sequence of SEQ ID NO: 9;
   (ii) optionally a nucleotide sequence encoding the extracellular domain of the human CD80 ligand suitable for targeting cells and consisting of the sequence of SEQ ID NO: 15;
   (iii) a nucleotide sequence encoding an Ig-like domain of the Leukemia Inhibitory Factor receptor gp190 and consisting of the sequence of SEQ ID NO: 3;
   (iv) a nucleotide sequence encoding a peptide linker and consisting of the sequence of SEQ ID NO: 5;
   (v) a nucleotide sequence encoding an extracellar domain of the human FasL protein and consisting of the sequence of SEQ ID NO: 7.

16. The nucleic acid molecule according to claim 14, comprising at least one of the nucleotide sequences selected from the group consisting of SEQ ID NO: 1, SEQ ID NO: 11, and SEQ ID NO: 17.

17. An expression vector comprising the nucleic acid molecule of claim 14.

18. The expression vector according to claim 17, which is a plasmid or a viral or a lentiviral vector.

19. An isolated or cultured cell which is transfected or transduced with the nucleic acid molecule of claim 14.

20. An anti-tumor therapeutic composition which comprises, as an active ingredient against tumor development, the chimeric molecule according to claim 1,
   and a pharmaceutical excipient suitable for administration by injection to a human patient.

21. A method for treating a human patient diagnosed with transformed cells or with uncontrolled proliferative cells or for treating a human patient diagnosed for infection, wherein said transformed, proliferative or infected cells express the Fas cellular receptor, the method comprising administering to said human patient an effective amount of the chimeric molecule according to claim 1 as a cytotoxic agent.

22. A method for inducing cellular apoptosis in a human patient, comprising administering to said human patient an effective amount of the chimeric molecule according to claim 1.

23. A method for treating cancer, comprising administering to a subject in need thereof an effective amount of the chimeric molecule according to claim 1.

* * * * *